US009492404B2

(12) United States Patent
Watson et al.

(10) Patent No.: US 9,492,404 B2
(45) Date of Patent: Nov. 15, 2016

(54) COMPOSITIONS AND METHODS FOR TREATMENT OF TAUPATHY

(75) Inventors: Richard L. Watson, McPherson, KS (US); Anthony B. Wood, Dallas, TX (US); Gregory J. Archambeau, Puyallup, WA (US)

(73) Assignee: Revalesio Corporation, Tacoma, WA (US)

( * ) Notice: Subject to any disclaimer, the term of this patent is extended or adjusted under 35 U.S.C. 154(b) by 0 days.

(21) Appl. No.: 13/209,201

(22) Filed: Aug. 12, 2011

(65) Prior Publication Data

US 2012/0039958 A1 Feb. 16, 2012

Related U.S. Application Data

(60) Provisional application No. 61/373,223, filed on Aug. 12, 2010.

(51) Int. Cl.

| | |
|---|---|
| A61K 38/21 | (2006.01) |
| A61P 25/28 | (2006.01) |
| A61K 9/00 | (2006.01) |
| A61K 31/46 | (2006.01) |
| A61K 31/47 | (2006.01) |
| A61K 31/137 | (2006.01) |
| A61P 29/00 | (2006.01) |
| A61K 31/58 | (2006.01) |
| A61K 31/56 | (2006.01) |
| A61K 31/167 | (2006.01) |
| A61K 31/44 | (2006.01) |
| A61K 31/436 | (2006.01) |
| A61K 31/136 | (2006.01) |
| A61P 25/00 | (2006.01) |
| A61K 39/395 | (2006.01) |
| A61K 38/13 | (2006.01) |
| A61K 41/00 | (2006.01) |

(52) U.S. Cl.
CPC ........... *A61K 31/136* (2013.01); *A61K 31/137* (2013.01); *A61K 31/167* (2013.01); *A61K 31/436* (2013.01); *A61K 31/44* (2013.01); *A61K 31/46* (2013.01); *A61K 31/47* (2013.01); *A61K 31/56* (2013.01); *A61K 31/58* (2013.01); *A61K 38/13* (2013.01); *A61K 38/21* (2013.01); *A61K 41/0004* (2013.01)

(58) Field of Classification Search
None
See application file for complete search history.

(56) References Cited

U.S. PATENT DOCUMENTS

| | | | |
|---|---|---|---|
| 1,627,161 A | 5/1927 | Edwards | |
| 1,650,561 A | 11/1927 | Williams | |
| 1,650,612 A | 11/1927 | Deniston | |
| 1,711,154 A | 4/1929 | Michal | |
| 2,115,123 A | 4/1938 | Russell | |
| 2,159,670 A | 5/1939 | Neitzke | |
| 2,278,051 A | 3/1942 | Ambrose | |
| 2,591,966 A | 4/1952 | Rider | |
| 2,606,502 A | 8/1952 | Carlson | |
| 2,639,901 A | 5/1953 | Teale | |
| 2,688,470 A | 9/1954 | Marco | |
| 2,734,728 A | 2/1956 | Myers | |
| 2,798,698 A | 7/1957 | Dooley | |
| 2,960,318 A | 11/1960 | Caillaud | |
| 2,969,960 A | 1/1961 | Gurley | |
| 2,970,817 A | 2/1961 | Gurley, Jr. | |
| 2,995,346 A | 8/1961 | Samples | |
| 3,174,185 A | 3/1965 | Gerber | |
| 3,182,975 A | 5/1965 | Stewart | |
| 3,194,540 A | 7/1965 | Hager | |
| 3,332,631 A | 7/1967 | Wood | |

(Continued)

FOREIGN PATENT DOCUMENTS

| | | |
|---|---|---|
| CN | 1399559 | 2/2003 |
| CN | 1499977 | 5/2004 |

(Continued)

OTHER PUBLICATIONS

Lee et al. "Tau phosphorylation in Alzheimer's disease: pathogen or protector?", Trends in Molecular Medicine, 11(4), 2005, pp. 164-169.*

(Continued)

*Primary Examiner* — Bethany Barham
*Assistant Examiner* — Melissa Javier
(74) *Attorney, Agent, or Firm* — Barry L. Davison; Davis Wright Tremaine LLP

(57) ABSTRACT

Provided are electrokinetically-altered fluids (e.g., electrokinetically-altered gas-enriched fluids and solutions) comprising an ionic aqueous solution of charge-stabilized oxygen-containing nanostructures in an amount sufficient for treating an inflammatory neurodegenerative condition or disease (e.g., a taupathy) or at least one symptom thereof. The electrokinetically-altered fluids or therapeutic compositions and methods include electrokinetically-altered ionic aqueous fluids optionally in combination with other therapeutic agents. Particular aspects provide for modulating phosphorylation of tau protein. Particular aspects provide for regulating or modulating intracellular signal transduction associated with said inflammatory responses by modulation of at least one of cellular membrane potential and/or conductance, membrane proteins such as membrane receptors, including but not limited to G-Protein Coupled Receptors (GPCR), and intercellular junctions (e.g., tight junctions, gap junctions, zona adherins and desmasomes). Other embodiments include particular routes of administration or formulations for the electrokinetically-altered fluids and therapeutic compositions.

13 Claims, 25 Drawing Sheets

(56) References Cited

U.S. PATENT DOCUMENTS

| | | |
|---|---|---|
| 3,333,771 A | 8/1967 | Graham |
| 3,333,828 A | 8/1967 | Boehme |
| 3,471,131 A | 10/1969 | Fritzweiler |
| 3,514,079 A | 5/1970 | Little, Jr. |
| 3,630,498 A | 12/1971 | Bielinski |
| 3,653,637 A | 4/1972 | Eckhardt |
| 3,660,933 A | 5/1972 | Wong, Jr. |
| 3,744,763 A | 7/1973 | Schnoring |
| 3,791,349 A | 2/1974 | Schaefer |
| 3,925,243 A | 12/1975 | Brogli |
| 3,937,445 A | 2/1976 | Agosta |
| 3,938,783 A | 2/1976 | Porter |
| 3,939,073 A | 2/1976 | Bats |
| 3,980,280 A | 9/1976 | Benson |
| 3,986,709 A | 10/1976 | Vermeulen |
| 3,996,012 A | 12/1976 | Zucker |
| 3,998,433 A | 12/1976 | Iwako |
| 4,004,553 A | 1/1977 | Stenstrom |
| 4,011,027 A | 3/1977 | Selder |
| 4,014,526 A | 3/1977 | Cramer |
| 4,049,240 A | 9/1977 | Walters |
| 4,051,204 A | 9/1977 | Muller |
| 4,057,223 A | 11/1977 | Rosenberger |
| 4,057,933 A | 11/1977 | Enyeart |
| 4,069,147 A | 1/1978 | Abrams |
| 4,071,225 A | 1/1978 | Holl |
| 4,089,507 A | 5/1978 | Arai |
| 4,097,026 A | 6/1978 | Haindl |
| 4,116,164 A | 9/1978 | Shabi |
| 4,117,550 A | 9/1978 | Folland |
| 4,127,332 A | 11/1978 | Thiruvengadam |
| 4,128,342 A | 12/1978 | Renk |
| 4,136,971 A | 1/1979 | Varlamov |
| 4,143,639 A | 3/1979 | Frenette |
| 4,144,167 A | 3/1979 | Burkett |
| 4,159,944 A | 7/1979 | Erickson |
| 4,162,153 A | 7/1979 | Spector |
| 4,163,712 A | 8/1979 | Smith |
| 4,172,668 A | 10/1979 | Thompson |
| 4,175,873 A | 11/1979 | Iwako |
| 4,183,681 A | 1/1980 | Li |
| 4,201,487 A | 5/1980 | Backhaus |
| 4,213,712 A | 7/1980 | Aanonsen |
| 4,261,521 A | 4/1981 | Ashbrook |
| 4,263,003 A | 4/1981 | Vork |
| 4,284,623 A | 8/1981 | Beck |
| 4,289,733 A | 9/1981 | Saito |
| 4,294,549 A | 10/1981 | Thompson |
| 4,316,673 A | 2/1982 | Speer |
| 4,318,429 A | 3/1982 | Gouttebessis |
| 4,332,486 A | 6/1982 | Mutalibov |
| 4,361,414 A | 11/1982 | Nemes |
| 4,368,986 A | 1/1983 | Fischer |
| 4,383,767 A | 5/1983 | Jido |
| 4,388,915 A | 6/1983 | Shafran |
| 4,393,017 A | 7/1983 | Kim |
| 4,394,966 A | 7/1983 | Snyder |
| 4,408,890 A | 10/1983 | Beckmann |
| 4,416,548 A | 11/1983 | Carre |
| 4,424,797 A | 1/1984 | Perkins |
| 4,436,430 A | 3/1984 | Mayer |
| 4,441,823 A | 4/1984 | Power |
| 4,444,510 A | 4/1984 | Janssen |
| 4,469,595 A | 9/1984 | Napadow |
| 4,474,479 A | 10/1984 | Redelman |
| 4,477,338 A | 10/1984 | Hellmann |
| 4,507,285 A | 3/1985 | Kuhne |
| 4,509,861 A | 4/1985 | Sjonell |
| 4,533,254 A | 8/1985 | Cook |
| 4,539,139 A | 9/1985 | Ichikawa |
| 4,550,022 A | 10/1985 | Garabedian et al. |
| 4,594,228 A | 6/1986 | Lambert |
| 4,619,072 A | 10/1986 | Privett |
| 4,633,909 A | 1/1987 | Louboutin |
| 4,634,675 A | 1/1987 | Freedman |
| 4,645,606 A | 2/1987 | Ashbrook |
| 4,661,243 A | 4/1987 | Hotz |
| 4,663,055 A | 5/1987 | Ling |
| 4,664,680 A | 5/1987 | Weber |
| 4,684,614 A | 8/1987 | Krovak |
| 4,687,579 A | 8/1987 | Bergman |
| 4,696,283 A | 9/1987 | Kohlmetz |
| 4,715,274 A | 12/1987 | Paoletti |
| 4,733,972 A | 3/1988 | Weis |
| 4,735,133 A | 4/1988 | Paoletti |
| 4,749,493 A | 6/1988 | Hicks |
| 4,753,535 A | 6/1988 | King |
| 4,764,283 A | 8/1988 | Ashbrook |
| 4,765,807 A | 8/1988 | Henriksen |
| 4,778,336 A | 10/1988 | Husain |
| 4,793,247 A | 12/1988 | Verweij |
| 4,798,176 A | 1/1989 | Perkins |
| 4,808,007 A | 2/1989 | King |
| 4,820,381 A | 4/1989 | Brown |
| 4,834,545 A | 5/1989 | Inoue |
| 4,838,699 A | 6/1989 | Jour |
| 4,880,445 A | 11/1989 | Watten |
| 4,884,892 A | 12/1989 | Gust |
| 4,886,368 A | 12/1989 | King |
| 4,906,574 A | 3/1990 | Erdei |
| 4,908,101 A | 3/1990 | Frisk |
| 4,937,004 A | 6/1990 | Mandrin |
| 4,957,626 A | 9/1990 | Ashbrook |
| 4,972,801 A | 11/1990 | Hunt |
| 4,973,168 A | 11/1990 | Chan |
| 4,976,547 A | 12/1990 | Hisanaga |
| 4,999,015 A | 3/1991 | Demaris |
| 5,005,982 A | 4/1991 | Kistner |
| 5,006,352 A | 4/1991 | Zelenak nee Zoltai et al. |
| 5,011,372 A | 4/1991 | Nigrelli et al. |
| 5,024,647 A | 6/1991 | Jubin |
| 5,052,813 A | 10/1991 | Latto |
| 5,075,234 A | 12/1991 | Tunac |
| 5,141,328 A | 8/1992 | Dilley |
| 5,152,212 A | 10/1992 | Chauveau |
| 5,176,447 A | 1/1993 | Bata |
| 5,185,081 A | 2/1993 | Nyman |
| 5,188,090 A | 2/1993 | Griggs |
| 5,205,647 A | 4/1993 | Ricciardi |
| 5,263,774 A | 11/1993 | Delcourt |
| 5,275,486 A | 1/1994 | Fissenko |
| 5,279,262 A | 1/1994 | Muehleck |
| 5,279,463 A | 1/1994 | Holl |
| 5,281,341 A | 1/1994 | Reimers |
| 5,304,001 A | 4/1994 | Kuo |
| 5,318,702 A | 6/1994 | Ashbrook |
| 5,326,484 A | 7/1994 | Nakashima |
| 5,341,692 A | 8/1994 | Sher et al. |
| 5,341,768 A | 8/1994 | Pope |
| 5,366,288 A | 11/1994 | Dahllof |
| 5,370,824 A | 12/1994 | Nagano |
| 5,372,424 A | 12/1994 | Lecouturier |
| 5,372,824 A | 12/1994 | Record et al. |
| 5,378,321 A | 1/1995 | Delcourt |
| 5,380,089 A | 1/1995 | Karasawa |
| 5,380,471 A | 1/1995 | Ban |
| 5,403,089 A | 4/1995 | Kuo |
| 5,407,637 A | 4/1995 | Gibboney |
| 5,419,306 A | 5/1995 | Huffman |
| 5,435,913 A | 7/1995 | Ashbrook |
| 5,450,368 A | 9/1995 | Kubota |
| 5,470,153 A | 11/1995 | De Naeghel |
| 5,474,380 A | 12/1995 | Sukup |
| 5,482,369 A | 1/1996 | Verstallen |
| 5,496,108 A | 3/1996 | Sukup |
| 5,511,877 A | 4/1996 | King |
| 5,538,191 A | 7/1996 | Holl |
| 5,538,343 A | 7/1996 | Tynan |
| 5,551,859 A | 9/1996 | Cantrill |
| 5,552,133 A | 9/1996 | Lambert |
| 5,556,765 A | 9/1996 | Dedolph |
| 5,560,710 A | 10/1996 | Klocke |
| 5,561,944 A | 10/1996 | Ismail |
| 5,563,189 A | 10/1996 | Hosokawa |

(56) References Cited

U.S. PATENT DOCUMENTS

| | | |
|---|---|---|
| 5,569,416 A | 10/1996 | Cross |
| 5,575,559 A | 11/1996 | Roll |
| 5,590,961 A | 1/1997 | Rasmussen |
| 5,616,304 A | 4/1997 | Stormo |
| 5,630,909 A | 5/1997 | LaRiviere |
| 5,658,380 A | 8/1997 | Dillenbeck |
| 5,665,228 A | 9/1997 | Leaverton et al. |
| 5,671,664 A | 9/1997 | Jacobson |
| 5,674,312 A | 10/1997 | Mazzei |
| 5,697,187 A | 12/1997 | Persinger |
| 5,711,887 A | 1/1998 | Gastman et al. |
| 5,711,950 A | 1/1998 | Lorenzen |
| 5,720,551 A | 2/1998 | Shechter |
| 5,744,105 A | 4/1998 | Stormo |
| 5,766,490 A | 6/1998 | Taylor |
| 5,770,062 A | 6/1998 | Isbell |
| 5,779,996 A | 7/1998 | Stormo |
| 5,782,556 A | 7/1998 | Chu |
| 5,791,778 A | 8/1998 | Manninen |
| 5,810,052 A | 9/1998 | Kozyuk |
| 5,810,474 A | 9/1998 | Hidalgo |
| 5,813,758 A | 9/1998 | Delcourt |
| 5,814,222 A | 9/1998 | Zelenak |
| 5,823,671 A | 10/1998 | Mitchell |
| 5,845,993 A | 12/1998 | Shirtum |
| 5,851,068 A | 12/1998 | Rumph |
| 5,863,120 A | 1/1999 | Gallagher et al. |
| 5,865,537 A | 2/1999 | Streiff |
| 5,868,495 A | 2/1999 | Hidalgo |
| 5,868,944 A | 2/1999 | Wright |
| 5,885,467 A | 3/1999 | Zelenak |
| 5,887,383 A | 3/1999 | Soeda |
| 5,893,337 A | 4/1999 | Sevic |
| 5,902,042 A | 5/1999 | Imaizumi |
| 5,904,851 A | 5/1999 | Taylor |
| 5,918,976 A | 7/1999 | Hashimoto |
| 5,921,678 A | 7/1999 | Desai |
| 5,921,679 A | 7/1999 | Muzzio |
| 5,925,292 A | 7/1999 | Ziesenis |
| 5,931,771 A | 8/1999 | Kozyuk |
| 5,938,581 A | 8/1999 | Bibette |
| 5,948,326 A | 9/1999 | Pate |
| 5,951,922 A | 9/1999 | Mazzei |
| 5,957,122 A | 9/1999 | Griggs |
| 5,971,601 A | 10/1999 | Kozyuk |
| 5,993,752 A | 11/1999 | Kobayashi |
| 5,997,717 A | 12/1999 | Miyashita et al. |
| 6,000,840 A | 12/1999 | Paterson |
| 6,017,447 A | 1/2000 | Wright |
| 6,019,499 A | 2/2000 | Selivanov |
| 6,042,792 A | 3/2000 | Shefer |
| 6,086,243 A | 7/2000 | Paul |
| 6,092,921 A | 7/2000 | Wentinck |
| 6,096,221 A | 8/2000 | Kerchouche |
| 6,110,353 A | 8/2000 | Hough |
| 6,120,008 A | 9/2000 | Littman |
| 6,120,668 A | 9/2000 | Kim |
| 6,135,628 A | 10/2000 | DeStefano |
| 6,153,607 A | 11/2000 | Pflugfelder et al. |
| 6,173,526 B1 | 1/2001 | Mazzei |
| 6,180,059 B1 | 1/2001 | Divino |
| 6,190,549 B1 | 2/2001 | Schwartz |
| 6,193,786 B1 | 2/2001 | Henderson |
| 6,210,030 B1 | 4/2001 | Ibar |
| 6,228,259 B1 | 5/2001 | Schwartz |
| 6,234,206 B1 | 5/2001 | Malmberg |
| 6,238,645 B1 | 5/2001 | Spears |
| 6,238,706 B1 | 5/2001 | Sonnenschein |
| 6,241,802 B1 | 6/2001 | Spears |
| 6,250,609 B1 | 6/2001 | Cheng |
| 6,257,754 B1 | 7/2001 | Sondergaard |
| 6,276,825 B2 | 8/2001 | Running |
| 6,279,611 B2 | 8/2001 | Uematsu |
| 6,279,882 B1 | 8/2001 | Littman |
| 6,284,293 B1 | 9/2001 | Crandall |
| 6,290,857 B1 | 9/2001 | Brahmbhatt |
| 6,294,212 B1 | 9/2001 | Huber |
| 6,299,343 B1 | 10/2001 | Pekerman |
| 6,312,647 B1 | 11/2001 | Spears |
| 6,315,942 B1 | 11/2001 | Spears |
| 6,332,706 B1 | 12/2001 | Hall |
| 6,338,569 B1 | 1/2002 | McGill |
| 6,344,489 B1 | 2/2002 | Spears |
| 6,366,751 B1 | 4/2002 | Shakuto et al. |
| 6,367,783 B1 | 4/2002 | Raftis |
| 6,380,264 B1 | 4/2002 | Jameson |
| 6,382,601 B1 | 5/2002 | Ohnari |
| 6,386,751 B1 | 5/2002 | Wootan et al. |
| 6,398,402 B1 | 6/2002 | Thomas |
| 6,402,361 B1 | 6/2002 | Reinemuth |
| 6,412,714 B1 | 7/2002 | Witsken |
| 6,413,418 B2 | 7/2002 | Brahmbhatt |
| 6,431,742 B2 | 8/2002 | Mori |
| 6,443,610 B1 | 9/2002 | Shechter |
| 6,451,328 B1 | 9/2002 | Ionita-Manzatu et al. |
| 6,454,997 B1 | 9/2002 | Divino |
| 6,458,071 B1 | 10/2002 | Jacobson |
| 6,474,264 B1 | 11/2002 | Grimberg |
| 6,474,862 B2 | 11/2002 | Farrell |
| 6,481,649 B1 | 11/2002 | Schmidt |
| 6,485,003 B2 | 11/2002 | Speece |
| 6,488,401 B1 | 12/2002 | Seaman |
| 6,488,765 B1 | 12/2002 | Tseng |
| 6,494,055 B1 | 12/2002 | Meserole |
| 6,499,671 B1 | 12/2002 | Sands et al. |
| 6,521,248 B1 | 2/2003 | Holloway |
| 6,524,475 B1 | 2/2003 | Herrington |
| 6,530,895 B1 | 3/2003 | Keirn |
| 6,538,041 B1 | 3/2003 | Marelli |
| 6,540,436 B2 | 4/2003 | Ogi |
| 6,551,492 B2 | 4/2003 | Hanaoka |
| 6,557,492 B1 | 5/2003 | Robohm |
| 6,576,130 B2 | 6/2003 | Wallace |
| 6,582,387 B2 | 6/2003 | Derek |
| 6,586,441 B2 | 7/2003 | Borroni et al. |
| 6,596,235 B2 | 7/2003 | Divino |
| 6,602,468 B2 | 8/2003 | Patterson |
| 6,613,280 B2 | 9/2003 | Myrick |
| 6,619,399 B1 | 9/2003 | Chatterji |
| 6,627,784 B2 | 9/2003 | Hudson et al. |
| 6,632,014 B2 | 10/2003 | Steinberg |
| 6,649,145 B2 | 11/2003 | McGrath |
| 6,655,830 B1 | 12/2003 | Seaman |
| 6,669,966 B1 | 12/2003 | Antelman |
| 6,676,900 B1 | 1/2004 | Divino |
| 6,682,215 B2 | 1/2004 | Kinsley |
| 6,682,732 B1 | 1/2004 | Blake et al. |
| 6,688,883 B2 | 2/2004 | Tseng |
| 6,689,262 B2 | 2/2004 | Senkiw |
| 6,702,949 B2 | 3/2004 | Wood |
| 6,705,755 B1 | 3/2004 | Innings |
| 6,730,211 B2 | 5/2004 | Hanaoka |
| 6,733,172 B2 | 5/2004 | Lee |
| 6,749,329 B2 | 6/2004 | Shechter |
| 6,752,529 B2 | 6/2004 | Holl |
| 6,764,213 B2 | 7/2004 | Shechter |
| 6,782,924 B2 | 8/2004 | Daoud |
| 6,796,702 B2 | 9/2004 | Wire |
| 6,821,438 B2 | 11/2004 | Hadley |
| 6,837,986 B2 | 1/2005 | Hanaoka |
| 6,857,774 B2 | 2/2005 | Kozyuk |
| 6,869,212 B2 | 3/2005 | Uesugi |
| 6,905,523 B2 | 6/2005 | Vainshelboim |
| 6,910,448 B2 | 6/2005 | Thoma |
| 6,935,768 B2 | 8/2005 | Lowe |
| 6,935,770 B2 | 8/2005 | Schueler |
| 6,936,179 B2 | 8/2005 | DeWald |
| 6,936,221 B1 | 8/2005 | Divino |
| 6,955,713 B2 | 10/2005 | Rittner |
| 6,958,163 B2 | 10/2005 | Ionita-Manzatu et al. |
| 6,959,669 B2 | 11/2005 | Thoma |
| 6,974,546 B2 | 12/2005 | Wood |
| 7,008,535 B1 | 3/2006 | Spears |
| 7,037,842 B2 | 5/2006 | Verhaverbeke |

(56) References Cited

U.S. PATENT DOCUMENTS

| | | |
|---|---|---|
| 7,069,073 B2 | 6/2006 | Henley et al. |
| 7,089,886 B2 | 8/2006 | Thoma |
| 7,090,753 B2 | 8/2006 | Sumita |
| 7,121,714 B2 | 10/2006 | Parker Metcalfe, III et al. |
| 7,128,278 B2 | 10/2006 | Archambeau et al. |
| 7,137,620 B2 | 11/2006 | Thomas |
| 7,137,621 B1 | 11/2006 | Bagley |
| 7,179,375 B2 | 2/2007 | Wood |
| 7,198,254 B2 | 4/2007 | Holloway et al. |
| 7,201,225 B2 | 4/2007 | Smith |
| 7,223,246 B2 | 5/2007 | Don |
| 7,237,943 B2 | 7/2007 | Brown |
| 7,241,723 B2 | 7/2007 | Zhang |
| 7,243,910 B2 | 7/2007 | Bagley |
| 7,255,881 B2 | 8/2007 | Gillis et al. |
| 7,316,501 B2 | 1/2008 | Thoma |
| 7,334,781 B2 | 2/2008 | Donnelly |
| 7,347,944 B2 | 3/2008 | Bagley |
| 7,360,755 B2 | 4/2008 | Hudson |
| 7,387,262 B2 | 6/2008 | Thoma |
| 7,396,441 B2 | 7/2008 | Senkiw |
| 7,544,365 B2 | 6/2009 | Dosch et al. |
| 7,654,728 B2 | 2/2010 | Wood et al. |
| 7,690,833 B2 | 4/2010 | Metcalfe |
| 7,731,953 B2 | 6/2010 | Leonard |
| 7,749,692 B2 | 7/2010 | Mano |
| 7,770,814 B2 | 8/2010 | Archambeau |
| 7,806,584 B2 | 10/2010 | Wood et al. |
| 7,832,920 B2 | 11/2010 | Wood et al. |
| 7,887,698 B2 | 2/2011 | Wood |
| 7,919,534 B2 | 4/2011 | Wood et al. |
| 8,349,191 B2 | 1/2013 | Wood |
| 8,410,182 B2 | 4/2013 | Wood et al. |
| 8,445,546 B2 | 5/2013 | Wood et al. |
| 8,449,172 B2 | 5/2013 | Wood et al. |
| 8,470,893 B2 | 6/2013 | Wood et al. |
| 2001/0003291 A1 | 6/2001 | Uematsu et al. |
| 2001/0022755 A1 | 9/2001 | Holtzapple |
| 2001/0031740 A1 | 10/2001 | Unger et al. |
| 2001/0040134 A1 | 11/2001 | Brahmbhatt et al. |
| 2002/0045742 A1 | 4/2002 | Jones et al. |
| 2002/0136662 A1 | 9/2002 | Myrick et al. |
| 2002/0138034 A1 | 9/2002 | Derek et al. |
| 2002/0164379 A1 | 11/2002 | Nishihara |
| 2002/0184820 A1 | 12/2002 | Mauney |
| 2002/0187203 A1 | 12/2002 | Cioca et al. |
| 2002/0196702 A1 | 12/2002 | Shechter |
| 2003/0017001 A1 | 1/2003 | Ogi |
| 2003/0022288 A1 | 1/2003 | Zuker et al. |
| 2003/0042174 A1 | 3/2003 | Austin |
| 2003/0056805 A1 | 3/2003 | Sumita |
| 2003/0057163 A1 | 3/2003 | Wood |
| 2003/0072212 A1 | 4/2003 | Wood et al. |
| 2003/0083610 A1 | 5/2003 | McGrath et al. |
| 2003/0147303 A1 | 8/2003 | Schueler |
| 2003/0188740 A1 | 10/2003 | Tribelsky |
| 2003/0199089 A1 | 10/2003 | Surber et al. |
| 2003/0232114 A1 | 12/2003 | Dekleva |
| 2004/0004042 A1 | 1/2004 | Hadley et al. |
| 2004/0019319 A1 | 1/2004 | Derek et al. |
| 2004/0022122 A1 | 2/2004 | Kozyuk |
| 2004/0027915 A1 | 2/2004 | Lowe |
| 2004/0058010 A1 | 3/2004 | Holloway et al. |
| 2004/0060446 A1 | 4/2004 | Rittner |
| 2004/0089746 A1 | 5/2004 | Archambeau |
| 2004/0090862 A1 | 5/2004 | Uesugi |
| 2004/0118701 A1 | 6/2004 | Senkiw |
| 2004/0126468 A1 | 7/2004 | Holloway et al. |
| 2004/0129112 A1 | 7/2004 | Gillis et al. |
| 2004/0142377 A1 | 7/2004 | Unett et al. |
| 2004/0166171 A1 | 8/2004 | McGrath et al. |
| 2004/0222106 A1 | 11/2004 | Hough |
| 2004/0235732 A1 | 11/2004 | Zhou et al. |
| 2004/0241154 A1 | 12/2004 | Davis et al. |
| 2004/0245186 A1 | 12/2004 | Wood |
| 2004/0248909 A1 | 12/2004 | Sun et al. |
| 2004/0258687 A1 | 12/2004 | Waldman et al. |
| 2004/0266693 A1 | 12/2004 | Ruben et al. |
| 2005/0047270 A1 | 3/2005 | Wood et al. |
| 2005/0048034 A1 | 3/2005 | Fraser et al. |
| 2005/0096458 A1 | 5/2005 | Dumas Milne Edwards et al. |
| 2005/0139808 A1 | 6/2005 | Alimi |
| 2005/0142157 A1 | 6/2005 | Alimi |
| 2005/0196370 A1 | 9/2005 | Yu et al. |
| 2005/0196462 A1 | 9/2005 | Alimi |
| 2005/0249712 A1 | 11/2005 | Leonard et al. |
| 2005/0259510 A1 | 11/2005 | Thoma |
| 2005/0263607 A1 | 12/2005 | Thoma |
| 2005/0273018 A1 | 12/2005 | Don |
| 2006/0030900 A1 | 2/2006 | Eckert |
| 2006/0039902 A1 | 2/2006 | Young et al. |
| 2006/0039910 A1 | 2/2006 | Comeau et al. |
| 2006/0045796 A1 | 3/2006 | Anderle et al. |
| 2006/0054205 A1 | 3/2006 | Yabe et al. |
| 2006/0098528 A1 | 5/2006 | Wood |
| 2006/0116419 A1 | 6/2006 | Callahan et al. |
| 2006/0135585 A1 | 6/2006 | Day et al. |
| 2006/0146644 A1 | 7/2006 | Holloway et al. |
| 2006/0150491 A1 | 7/2006 | Senkiw |
| 2006/0198822 A1 | 9/2006 | Booth et al. |
| 2006/0198901 A9 | 9/2006 | Holloway, Jr. |
| 2006/0204458 A1 | 9/2006 | Holloway, Jr. et al. |
| 2006/0210613 A1 | 9/2006 | Carliss |
| 2006/0216360 A1 | 9/2006 | Upadhyay et al. |
| 2006/0235350 A1 | 10/2006 | Alimi |
| 2006/0241546 A1 | 10/2006 | Alimi |
| 2006/0253060 A1 | 11/2006 | Alimi |
| 2006/0272947 A1 | 12/2006 | Bagley |
| 2006/0272954 A1 | 12/2006 | Sumita |
| 2006/0273018 A1 | 12/2006 | Bagley |
| 2006/0273021 A1 | 12/2006 | Bagley |
| 2006/0273029 A1 | 12/2006 | Bagley |
| 2006/0273281 A1 | 12/2006 | Bagley |
| 2006/0273282 A1 | 12/2006 | Bagley |
| 2006/0273475 A1 | 12/2006 | Bagley |
| 2006/0275423 A1 | 12/2006 | Bagley |
| 2006/0292240 A1 | 12/2006 | Bagley |
| 2006/0292241 A1 | 12/2006 | Bagley |
| 2007/0003497 A1 | 1/2007 | Holloway, Jr. et al. |
| 2007/0021331 A1 | 1/2007 | Fraser et al. |
| 2007/0077553 A1 | 4/2007 | Bentwich |
| 2007/0141163 A1 | 6/2007 | Vitaliano et al. |
| 2007/0173460 A1 | 7/2007 | Alimi |
| 2007/0173755 A1 | 7/2007 | Alimi |
| 2007/0189972 A1 | 8/2007 | Chiba et al. |
| 2007/0196357 A1 | 8/2007 | Alimi |
| 2007/0196434 A1 | 8/2007 | Alimi |
| 2007/0205161 A1 | 9/2007 | Chiba et al. |
| 2007/0210180 A1 | 9/2007 | Archambeau et al. |
| 2007/0237787 A1 | 10/2007 | Leonard et al. |
| 2007/0259032 A1 | 11/2007 | Bright et al. |
| 2007/0286795 A1 | 12/2007 | Chiba et al. |
| 2007/0287917 A1 | 12/2007 | Takahashi et al. |
| 2008/0050452 A1 | 2/2008 | Chen et al. |
| 2008/0057486 A1 | 3/2008 | Mano et al. |
| 2008/0063720 A1 | 3/2008 | Gounko et al. |
| 2008/0139674 A1 | 6/2008 | Archambeau et al. |
| 2008/0146679 A1 | 6/2008 | Archambeau et al. |
| 2008/0153795 A1 | 6/2008 | Occleston |
| 2008/0161541 A1 | 7/2008 | Lazar et al. |
| 2008/0206356 A1 | 8/2008 | Guinovart Cirera et al. |
| 2008/0219088 A1 | 9/2008 | Wood et al. |
| 2008/0220089 A1 | 9/2008 | Hojo et al. |
| 2008/0241098 A1 | 10/2008 | Young et al. |
| 2008/0281001 A1 | 11/2008 | Wood et al. |
| 2009/0082264 A1 | 3/2009 | Fischer et al. |
| 2009/0208473 A1 | 8/2009 | Weisleder et al. |
| 2009/0227018 A1 | 9/2009 | Watson et al. |
| 2009/0247458 A1 | 10/2009 | Watson et al. |
| 2009/0263495 A1 | 10/2009 | Watson et al. |
| 2009/0274730 A1 | 11/2009 | Watson et al. |
| 2009/0274771 A1 | 11/2009 | Watson et al. |
| 2010/0003333 A1 | 1/2010 | Watson et al. |
| 2010/0004189 A1 | 1/2010 | Watson et al. |

(56) References Cited

U.S. PATENT DOCUMENTS

| | | |
|---|---|---|
| 2010/0008997 A1 | 1/2010 | Watson et al. |
| 2010/0009008 A1 | 1/2010 | Watson et al. |
| 2010/0015235 A1 | 1/2010 | Watson et al. |
| 2010/0021464 A1 | 1/2010 | Archambeau et al. |
| 2010/0028441 A1 | 2/2010 | Watson et al. |
| 2010/0028442 A1 | 2/2010 | Archambeau et al. |
| 2010/0028443 A1 | 2/2010 | Watson et al. |
| 2010/0029764 A1 | 2/2010 | Watson et al. |
| 2010/0038244 A1 | 2/2010 | Wood et al. |
| 2010/0098659 A1 | 4/2010 | Watson |
| 2010/0098687 A1 | 4/2010 | Watson |
| 2010/0166784 A1 | 7/2010 | Murphy et al. |
| 2010/0186680 A1 | 7/2010 | Matsumura et al. |
| 2010/0252492 A1 | 10/2010 | Wood |
| 2010/0297193 A1 | 11/2010 | Archambeau et al. |
| 2010/0303871 A1 | 12/2010 | Watson et al. |
| 2010/0303917 A1 | 12/2010 | Watson et al. |
| 2010/0303918 A1 | 12/2010 | Watson et al. |
| 2010/0310609 A1 | 12/2010 | Watson et al. |
| 2010/0310664 A1 | 12/2010 | Watson |
| 2010/0310665 A1 | 12/2010 | Watson |
| 2010/0311167 A1 | 12/2010 | Wood et al. |
| 2010/0316723 A1 | 12/2010 | Watson et al. |
| 2010/0323383 A1 | 12/2010 | Manel et al. |
| 2011/0008462 A1 | 1/2011 | Wood et al. |
| 2011/0075507 A1 | 3/2011 | Wootan et al. |
| 2011/0081384 A1 | 4/2011 | Archambeau et al. |
| 2011/0104804 A1 | 5/2011 | Wood et al. |
| 2011/0165172 A1 | 7/2011 | Yarranton |
| 2011/0245107 A1 | 10/2011 | Kuchroo et al. |
| 2012/0015083 A1 | 1/2012 | Wood |
| 2012/0034696 A1 | 2/2012 | Wood |
| 2012/0039884 A1 | 2/2012 | Watson |
| 2012/0039951 A1 | 2/2012 | Watson |
| 2012/0039958 A1 | 2/2012 | Watson |
| 2012/0114702 A1 | 5/2012 | Watson |
| 2012/0121656 A1 | 5/2012 | Watson |
| 2012/0263764 A1 | 10/2012 | Watson |
| 2013/0092368 A1 | 4/2013 | Wood |
| 2013/0252323 A1 | 9/2013 | Wood et al. |
| 2013/0260462 A1 | 10/2013 | Wood et al. |
| 2013/0270478 A1 | 10/2013 | Wood et al. |
| 2013/0295144 A1 | 11/2013 | Wood et al. |

FOREIGN PATENT DOCUMENTS

| | | |
|---|---|---|
| CN | 1845877 A | 10/2006 |
| CN | 101237875 | 8/2008 |
| DE | 1557171 | 7/1970 |
| DE | 3123743 | 3/1982 |
| DE | 3436049 | 4/1986 |
| DE | 4008676 | 9/1991 |
| DE | 4317078 | 11/1994 |
| DE | 10105118 | 8/2002 |
| DE | 10227818 | 8/2004 |
| EP | 0363009 | 4/1990 |
| EP | 0555498 | 8/1993 |
| EP | 0682000 | 11/1995 |
| EP | 0880993 | 12/1998 |
| EP | 1201296 | 10/2001 |
| EP | 1797869 | 6/2007 |
| GB | 1279736 | 6/1972 |
| JP | 53-146264 | 12/1978 |
| JP | 56-161893 | 12/1981 |
| JP | 2001171627 | 7/1989 |
| JP | 2003169332 | 7/1991 |
| JP | 2004290531 | 10/1992 |
| JP | 5096470 | 4/1993 |
| JP | 6114254 | 4/1994 |
| JP | 06262050 | 9/1994 |
| JP | 07-327547 | 12/1995 |
| JP | 8198969 | 8/1996 |
| JP | 9122465 | 5/1997 |
| JP | 11507874 | 7/1999 |
| JP | 2000271590 | 10/2000 |
| JP | 2003-144887 | 5/2003 |
| JP | 2003-520820 | 7/2003 |
| JP | 2003340938 | 9/2003 |
| JP | 2003334548 | 11/2003 |
| JP | 2004074131 | 3/2004 |
| JP | 2004121962 | 4/2004 |
| JP | 2004529090 | 9/2004 |
| JP | 2005110552 | 4/2005 |
| JP | 2005-523147 | 8/2005 |
| JP | 2005523147 | 8/2005 |
| JP | 2005245817 | 9/2005 |
| JP | 2005246293 | 9/2005 |
| JP | 2005246294 | 9/2005 |
| JP | 2006223239 | 8/2006 |
| JP | 2006521811 | 9/2006 |
| JP | 2006-273730 | 10/2006 |
| JP | 2007275089 | 10/2007 |
| JP | 2008063258 | 3/2008 |
| JP | 2008093611 | 4/2008 |
| JP | 2008093612 | 4/2008 |
| JP | 2008156320 | 7/2008 |
| JP | 2008237950 | 10/2008 |
| JP | 2008259456 | 10/2008 |
| JP | 2009039600 | 2/2009 |
| JP | 2010508088 | 3/2010 |
| NO | 152733 | 8/1985 |
| RU | 1768269 | 10/1992 |
| RU | 1773469 | 11/1992 |
| RU | 1820861 | 6/1993 |
| RU | 2091151 | 9/1997 |
| RU | 2131761 | 6/1999 |
| RU | 2165787 | 4/2001 |
| RU | 2166987 | 5/2001 |
| RU | 2284853 | 4/2005 |
| SU | 127999 | 1/1960 |
| SU | 162461 | 12/1961 |
| SU | 280441 | 11/1970 |
| SU | 495099 | 12/1975 |
| SU | 495862 | 12/1976 |
| SU | 889078 | 12/1981 |
| SU | 921611 | 4/1982 |
| SU | 1281290 | 1/1987 |
| SU | 1337098 | 9/1987 |
| SU | 1584990 | 8/1990 |
| SU | 1706683 | 1/1992 |
| WO | WO 92/05792 | 4/1992 |
| WO | WO92/05972 | 4/1992 |
| WO | WO95/35501 | 12/1995 |
| WO | WO96/23977 | 8/1996 |
| WO | WO97/27146 | 7/1997 |
| WO | WO98/30319 | 7/1998 |
| WO | WO99/16539 | 4/1999 |
| WO | WO00/02651 | 1/2000 |
| WO | WO00/20109 | 4/2000 |
| WO | WO 01/54704 | 8/2001 |
| WO | WO01/87471 | 11/2001 |
| WO | WO02/24222 | 3/2002 |
| WO | WO02/35234 | 5/2002 |
| WO | WO02/38510 | 5/2002 |
| WO | WO02/060458 | 8/2002 |
| WO | WO02/062455 | 8/2002 |
| WO | WO03/044430 | 5/2003 |
| WO | WO03/089123 | 11/2003 |
| WO | WO2004/013049 | 2/2004 |
| WO | WO2004/016344 | 2/2004 |
| WO | WO2004/022098 | 3/2004 |
| WO | WO2004/084807 | 10/2004 |
| WO | WO 2004/112649 | 12/2004 |
| WO | WO2005/007142 | 1/2005 |
| WO | WO2005/030649 | 4/2005 |
| WO | WO2005/032243 | 4/2005 |
| WO | WO2005/084718 | 9/2005 |
| WO | WO2005/084786 | 9/2005 |
| WO | WO2005/085141 | 9/2005 |
| WO | WO2005/113026 | 12/2005 |
| WO | WO2006/029385 | 3/2006 |
| WO | WO 2006/088210 | 8/2006 |
| WO | WO2006/133113 | 12/2006 |
| WO | WO2007/096149 | 8/2007 |

(56) References Cited

FOREIGN PATENT DOCUMENTS

| WO | WO2008/018932 | | 2/2008 |
|---|---|---|---|
| WO | WO2008/052143 | | 5/2008 |
| WO | WO2008/052145 | | 5/2008 |
| WO | WO2008/115290 | | 9/2008 |
| WO | WO2009/055614 | | 4/2009 |
| WO | WO2009/055620 | | 4/2009 |
| WO | WO2009/055729 | * | 4/2009 |
| WO | WO2009/055824 | | 4/2009 |
| WO | WO2009/062260 | | 5/2009 |
| WO | WO2009/134728 | | 11/2009 |
| WO | WO2010/048425 | | 4/2010 |
| WO | WO2010/048455 | | 4/2010 |
| WO | 2010126908 A1 | | 11/2010 |
| WO | 2011137317 A1 | | 11/2011 |

OTHER PUBLICATIONS

Sjogren et al. "Increased intrathecal inflammatory activity in frontotemporal dementia: pathophysiological implications", J. Neurol Neurosurg Psychiatry, 2004, 75, pp. 1107-1111.*

Baker at al. "Mutations in progranulin cause tau-negative frontotemporal dementia linked to chromosome 17", Nature, 442(24), 2006, pp. 916-919.*

Hardy et al. "The Amyloid Hypothesis of Alzheimer's Disease: Progress and Problems on the Road to Therapeutics", Science, 297, 2002, pp. 353-356.*

Progressive Supranuclear Palsy Fact Sheet, http://www.ninds.nih.gov/disorders/psp/detail_psp.htm, accessed Jan. 9, 2015.*

NINDS Corticobasal Degeneration Information Page, http://www.ninds.nih.gov/disorders/corticobasal_degeneration/corticobasal_degeneration.htm, accessed Jan. 9, 2015.*

Zozulya, Alla L. and Heinz Wiendl, "The role of regulatory T cells in multiple sclerosis," Nature Clinical Practice (Neurology) 1-15, Jun. 24, 2008.

Valmori, Danila et al., "Human ROR•t+ TH17 cells preferentially differentiate from naive FOXP3+Treg in the presence of lineage-specific polarizing factors," Proc. Natl. Acad. Sci. 107(45) 19402-19407, Nov. 9, 2010.

Vignali et al., "How regulatory T cells work," Nature Review—Immunology, Jul. 2008, 8:523-532.

Auclair et al., "Revisiting the Mechanism of P450 Enzymes with the Radical Clocks Norcarane and Spiro[2,5]octane," Journal of the American Chemical Society 124(21):6020-6027, 2002.

Austin et al., "The Non-Heme Diiron Alkane Monooxygenase of Pseudomonas oleovorans (AlkB) Hydroxylates via a Substrate Radical Intermediate," Journal of the American Chemical Society 122: 11747-11748, 2000.

Austin et al., "Xylene monooxygenase, a membrane-spanning non-heme diiron enzyme that hydroxylates hydrocarbons via a substrate radical intermediate," Journal of Inorganic Chemistry, 8:733-740, 2003.

Barnes et al., "How Do Corticosteroids Work in Asthma?" Ann. Intern. Med. 139, pp. 359-370, 2003.

Billington et al., "Signaling and regulation of G Protein-coupled receptors in airway smooth muscle," Respiratory Research 4(2): 1-23, 2003.

Boedker et al., Budesonide epimer R, LAU-8080 and phenyl butyl nitrone synergistically repress cyclooxygenase-2 induction in [IL-1β+Aβ42]-stressed human neural cells, Neuroscience Letters 380: 176-180, 2005.

Bonanno, "Corneal Metabolic Activity in Humans: Corneal Oxygen Consumption," Indiana University School of Optometry Faculty Research, http://www.opt.indiana.edu/people/faculty/bonanno/oxygen.htm, 4 pages, Apr. 9, 2003.

Bragg et al., "Hydrated Electron Dynamics: From Clusters to Bulk," Science Magazine 360(5696):669-671, Sep. 16, 2004.

Brazeau et al., "Intermediate Q from Soluble Methane Monooxygenase Hydroxylates the Mechanistic Substrate Probe Norcarane: Evidence for a Stepwise Reaction," Journal of the American Chemical Society, 123(48): 11831-11837, Dec. 5, 2001.

Bucy et al., "Initial increase in blood CD4+ lymphocytes after HIV antiretroviral therapy reflects redistribution from lymphoid tissues," The Journal of Clinical Investigation 103(10): 1391-1398, 1999.

Bunkin et al., "Existence of charged submicrobubble clusters in polar liquids as revealed by correlation between optical cavitation and electrical conductivity," Colloids and Surfaces A: Physiochemical and Engineering Aspects 110:207-212, 1996.

Campbell et al., "Redox Modulation of L-type Calcium Channels in Ferret Ventricular Myocytes," J. Gen. Physiol, 108:277-293, Abstract, Oct. 1996.

Celli et al., "Standards for the diagnosis and treatment of patients with COPD: a summary of the ATS/ERS position paper," Eur. Respir. J. 23:932-946, 2004.

Chaplin, "Declustered Water, Anomalous Water and Crystals," London South Bank University, http://lsbu.ac.uk/water/anmlous.html, 4 pages, retrieved Jul. 10, 2006.

De Angelis et al., "Electronic Structure and Reactivity of Isomeric Oxo-Mn(V) Porphyrins: Effects of Spin-State Crossing and pKa Modulation," Inorganic Chemistry 45(10):4268-4276, Feb. 22, 2006.

English translation of SU 495099, published Dec. 15, 1975.

Faul, "Sonochemistry—General Overview," Pollution Research Group, http://www.und.ac.za/prg/sonochem/ultragen.html (2 pages), Nov. 21, 2002.

Finkel, "Redox-dependent signal transduction," FEBS Letters 476:52-54, 2000.

Fletcher et al., "T cells in multiple sclerosis and experimental autoimmune encephalomyelitis," Clinical and Experimental Immunology 162:1-11, 2010.

Florusse et al., "Stable Low-Pressure Hydrogen Clusters Stored in a Binary Clathrate Hydrate," Science Magazine 306:469-471, Oct. 15, 2004.

Forney et al., "Fast Competitive Reactions in Tyalor-Couette Flow," Ind. Eng. Chem. Res. 44(19):7306-7312, 2005.

Frauenfelder et al., "The role of structure, energy landscape, dynamics, and allostery in the enzymatic function of myoglobin," Proceedings of the National Academy of Sciences 98(5):2370-2374, Feb. 27, 2001.

Gill S et. al., "Nanoparticles: Characteristics, mechanisms of action, and toxicity in pulmonary drug delivery—a review," Journal of Biomedical Nanotechnology 3(2):107-119, 2007.

Godoy et al., "Central and systemic IL-I exacerbates neurodegeneration and motor symptoms in a model of Parkinson's disease," Brain 131:1880-1894, 2008.

Gomes et al., "Calcium Channel Blocker Prevents T Helper Type 2 Cell-mediated Airway Inflammation," American Journal Respir Crit Care Med. 75(11): 1117-1124, 2007.

Gosens et al., "Muscarinic receptor signaling in the pathophysiology of asthma and COPD," Respiratory Research 7(73):1-15, May 9, 2006.

Groves, "High-valent iron in chemical and biological oxidations," Journal of Inorganic Biochemistry 100:434-447, Jan. 14, 2006.

Groves, "Reactivity and mechanisms of metalloporphyrin-catalyzed oxidations," Journal of Porphyrins and Phthalocyanines 4:350-352, 2002.

Guerra et al., "The Effect of Oxygen Free Radicals on Calcium Current and Dihydropyridine Binding Sites in Guinea-pig Ventricular Myocytes," British Journal of Pharmacology 118:1278-1284, 1996.

Hammer et al., "How Do Small Water Clusters Bind an Excess Electron," Science Magazine 306(5696):675-679, Sep. 16, 2004.

Harvitt et al., "Corneal Oxygen Availability and Metabolism with Contact Lens Wear and Re-evaluation of the Oxygen Diffsion Model for Predicting Minimum Contact Lens Dk/t Values Needed to Avoid Corneal Anoxia," http://vision.berkeley.edu/sarver/mdsl_harvitt_research.html (abstracts only) (2 pages), retrieved Apr. 9, 2003.

Headrick et al., "Spectral Signatures of Hydrated Proton Vibrations in Water Clusters," Science Magazine 308:1765-1770, Jun. 17, 2005.

(56) References Cited

OTHER PUBLICATIONS

Hogaboam et al., "Collagen Deposition in a Non-Fibrotic Lung," Am J. Pathol 153(6):1861-1872; abstract, Dec. 1998.
In re Robertson, 169 F.3d 743, Feb. 25, 1999.
Jia et al., "Atomic-Resolution of Oxygen Concentration in Oxide Materials," Science Magazine 303:2001-2004, Mar. 26, 2004.
Jin et al., "Unusual Kinetic Stability of a Ground-State Singlet Oxomanganese(V) Porphyrin. Evidence for a Spin State Crossing Effect," Journal of the American Chemical Society, 121:2923-2924, 1999.
Knobloch et al., "Dendritic spine loss and synaptic alterations in Alzheimer's disease," Mol. Neurobiol. 37:73-82, 2008.
Lassmann, "Hypoxia-like tissue injury as a component of multiple sclerosis lesions," J. Neurol. Sci. 206(2):187-191, abstract; p. 190, para 3, Feb. 15, 2003.
Life 02 International (Asia) Co., Ltd—Medical Industry, www.lifeo2asia.com/medical.htm (1 page), retrieved Jun. 3, 2003.
Liu, Yong-Jun, "Thymic stromal lymphopoietin: master switch for allergic inflammation," J. Experimental Medicine 203(2):269-273, 2006.
Ljunggren et al., "The Lifetime of a Colloid-Sized Gas Bubble in Water and the Cause of the Hydrophobic Attraction," Colloids and Surfaces A: Physicochemical and Engineering Aspects 129-130:151-155, 1997.
Lowenstein et al., "Nitric Oxide: A Physiologic Messenger," Annals of Internal Medicine 120(3):227-237, Abstract, Feb. 1, 1994.
Lower, "The BunkHouse: Water pseudoscience gallery, Gallery of water-related pseudoscience, Junk science in the marketplace," http://chem1.com/CO/gallery.html (18 pages), retrieved Jul. 25, 2006.
Luo et al., "Mycobactin-mediated iron acquisition within macrophages," Nature Chemical Biology 1(3):149-153, Aug. 2005.
Miyazaki et al., "Infrared Spectroscopic Evidence for Protonated Water Clusters Forming Nanoscale Cages," Science Magazine, 304:1134-1137, Apr. 29, 2004.
Moe et al., "Remarkable Aliphatic Hydroxylation by the Diiron Enzyme Toluene 4-Monooxygenase in reactions with Radical or Cation Diagnostic Probes Norcarane, 1,1-Dimethylcyclopropane, and 1,1-Diethylcyclopropane," American Chemical Society, 43:15688-15701, Jul. 1, 2004.
Morris, "The physiological causes of contact lens complications," Optometry Today, pp. 28-33, Dec. 3, 1999.
Murga et al, "Activation of Akt/Protein Kinase B by G Protein-coupled Receptors," The Journal of Biological Chemistry vol. 273(30):19080-19085, especially abstract p. 19085, col. 1, paragraph 3, 1998.
Murray et al. (May 17, 2011) "Exacerbation of CNS inflammation and neurodegeneration by systemic LPS treatment is independent of circulating IL-1$\beta$ and II-6"; Journal of Neuroinflammation; vol. 8; p. 50.
Neuman, et al., "Optical Trapping," Review of Scientific Instruments 75(9):2787-2809, Sep. 2004.
Nguyen et al., "Neuroprotection by NGF and BDGF Against Neurotoxin-Exerted Apoptotic Death in Neural Stem Cells Are Mediated Through Trk Receptors, Activating PI3-Kinase and MAPK Pathways," Neurochemical Research 34(5):942-951, especially abstract, p. 943, col. 1, paragraph 2-3, 2009.
Nozaki et al., "New enhancers for the chemiluminescent peroxidase catalyzed chemiluminescent oxidation of pyrogallol and purpurogallin," Journal of Biolumin Chemilumin 10:151-156, 1995.
Ohgaki et al., "Physiochemical approach to nanobubble solutions," Chemical Engineering Science 65:1296-1300, 2010.
Paik et al., "Electrons in Finite-Sized Water Cavities: Hydration Dynamics Observed in Real Time," Science Express, 306(5696):672-675, Sep. 16, 2004.
Pan et al., "Role of the Rho GTPas in Bradykinin-Stimulated Nuclear Factor-kB Activation and IL-1B Gene Expression in Cultured Human Epithelial Cells," J. Immunol. 160:3038-3045, The Scripps Researh Institue. La Jolla, 1998.

Park, et al., "Nitric oxide regulates nitric oxide synthase-2 gene expression by inhibiting NF-KB binding to DNA," Biochem J. 322:609-613, abstract, 1997.
Patent Office of the Russian Federation, Official Action, Application No. 2004133560/15(036500), original in Russian plus English translation (6 pages), Jan. 27, 2006.
Pronated Water Clusters in Nature, "Protonated Water Clusters in Interstellar Clouds, the Upper Atmosphere and Biomolecules," http://pro3.chem.pitt.edu/richard/prot_clust_nature.html (1 page), retrieved Oct. 29, 2004.
Rutgeerts et al., "Review article: the limitations of corticosteroid therapy in Crohn's disease," Aliment Pharmacol. Ther. 15(10):1515-1525, abstract, Oct. 2001.
Salzman et al., "Nitric oxide dilates tight junctions and depletes ATP in cultured Caco-2BBe intestinal epithelial monolayers," AJP-Gastrointestinal and Liver Physiology 268(2):361-G373, Abstract, 1995.
Sanchez-Pernaute et al., "Selective COX-2 inhibition prevents progressive dopamine neuron degeneration in a rat model of Parkinson's disease," Journal of Neuroinflammation 1(6):1-11, 2004.
Schmidt et al., "A role for Rho in receptor- and G protein-stimulated phospholipase C. Reduction in phosphatidylinositol 4,5-bisophosphate by Clostridium difficile toxin B.," Naunyn Schmiedebergs Arch Pharmacol 354(2):87-94, abstract only, Jul. 1996.
Science Week (1) Chemistry: On Protonated Water Clusters, points made by Zwier-Science (2004) 204:1119; (2) On Water Structure, points made by Head-Gordon et al.—Chem. Rev (2002) 102:2651; (3) Liquid Water: Current Research Problems, points made by Keutsch et al.—Proc. Nat. Acad. Sci. (2001) 98:10533.
Shin et al., "Infrared Signature of Structures Associated with the H+(H2O)n (n=6 to 27) Clusters, Science Magazine," 304:1137-1140, May 21, 2004.
Stoll et al., "Inflammation and Atherosclerosis Novel Insights into Plaque Formation and Destabilization," American Stroke Association through the American Journal of Heart Association 37:1923-1932, Jul. 2006.
Suslick, "Sonochemistry," Science Magazine 247:1439-1445, Mar. 23, 1990.
Torr, "Conversion between Torr and atm," http://antoine.frostburg.edu/chem/senese/101/solutions/faq/predicting-DO.shtml, downloaded Dec. 12, 2013.
Torre, "Is Alzheimer's disease a neurodegenerative or a vascular disorder? Data, dogma, and dialectics," Neurology 3:184-190, Mar. 2004.
Tristani-Firouzi et al., "Oxygen-induced constriction of rabbit ductus arteriosus via inhibition of a 4-aminopyridine-, voltage-sensitive potassium channel," J. Clin Invest 98:1959-1965, 1996.
Van Winsen et al., "Sensitivity to glucocorticoids is decreased in relapsing remitting multiple sclerosis," J. Clin. Endocrinol. Metab. 90(2):734-740, abstract, Feb. 2005.
Wang, "Radical Clocks: Molecular Stopwatches for timing Radical Reactions," pp. 65-72, Apr. 27, 2006.
Watson, U.S. Appl. No. 13/097,565, filed Apr. 29, 2011.
Watson, U.S. Appl. No. 13/126,117, filed Jul. 19, 2011.
Wojciak-Stothard et al., "Rac and Rho play opposing roles in the regulation of hypoxia/reoxygenation-induced permeability changes in pulmonary artery endothelial cells," Am J of Lung Cell Mol Physiol 288:L749-L760, 2005.
Wood et al., U.S. Appl. No. 12/861,179, filed Aug. 23, 2010.
Wood et al., U.S. Appl. No. 13/016,659, filed Jan. 28, 2011.
Wronski et al., "Interfacial area in a reactor with helicoidal flow for the twophase gas-liquid system," Chemical Engineering Journal 105:71-79, 2005.
(1) Wunderlich et al. "In vivo observation of oxygen-supersaturated water in the human mouth and stomach", Magnetic Resonance Imaging, 22(4): 551-556, 2004; (2) Divino et al. "Injection of highly supersaturated oxygen solutions without nucleation", Journal of Biomechanical Engineering, 124(6): 676-683, 2002; (3) 02 Canada Water, Product Information from 02 Canada Water, Inc., http://www.ocanadawater.com/BeverageDiffusion.html; (4) FBC Technologies "O2 x-Box (R)Super Oxygenation Process", http://www.fbctech.com/oxbox.htm, http://www.lsbu.ac.uk/water/anmlous.

(56) References Cited

OTHER PUBLICATIONS html; (5) Wayne State University Press Researcher Discovers Potential Approach to Hyperoxygenate Blood, Wayne State University Press Release, Apr. 4, 2006 (4 pages).
Ziegler et al., "Thymic stromal lymphopoietin in normal and pathogenic T cell development and function," Nature Immunology 7(7):709-714, Jul. 2006.
Ziegler, "The role of thymic stromal lymphopoietin (TSLP) in allergic disorders," Current Opinion in Immunology 22(6):795-799, Dec. 2010.
Ziegler, "Thymic stromal lymphopoietin (TSLP) and allergic disease," J. Allergy Clin. Immunol. 130(4): 845-852, Oct. 2012.
Zwier, "The structure of protonated water clusters," Science Magazine 304(5674):1119-1120, Apr. 29, 2004.
Akbar, "Expression of the TRPV1 receptor differs in quiescent inflammatory bowel disease with or without abdominal pain," Gut 59:767-774 (doi:10.1136/gut.2009.194449), 2010.
Aqueous Fluid (definition), Retrieved from http://www.thefreedictionary.com/aqueous and http://www.habazar.com/opticaldirectory/a2z.htm, Aug. 29, 2013.
Bates et al., "The use and misuse of Penh in animal models of lung disease," American Journal of Respiratory Cell and Molecular Biology 31(3):373-4, Sep. 2004.
Berger et al., "Antimyelin Antibodies as a Predicator of Clinically Definite Multiple Sclerosis after a First Demyelinating Event," The New England Journal of Medicine 349(2):139-145, Jul. 10, 2003.
Boyle, "Adult Cystic Fibrosis," Journal of the American Medical Association (JAMA) 296(13):1787-1793, Oct. 17, 2001.
Breitner et al., "Extended results of the Alzheimer's disease anti-inflammatory prevention trial (ADAPT)," Alzheimers Dement. 7(4):402-411, published Jul. 2011.
Bulakbasi et al., "Massive Lower Gastrointestinal Hemorrhage from the Surgical Anastomosis in Patients with Multiorgan Trauma: Treatment by Subselective Embolization with Polyvinyl Alcohol Particles," CardioVascular and Interventional Radiology 22:461-467, 1999.
Caro et al., "Healing and Relapse Rates in Gastroesophageal Reflux Disease Treated with the Newer Proton-Pump Inhibitors Lansoprazole, Rabeprazole, and Pantoprazole Compared with Omeprazole, Ranitidine, and Placebo: Evidence from Randomized Clinical Trials," Clinical Therapeutics 23(7):998-1017, 2001.
Cavitation Generator, English Translation of SU495099, published Dec. 15, 1975, 5 pages.
Cheng et al., HCl-acativated neural and epithelial vanilloid receptors (TRPV1) in cat esophageal mucosa, American Journal Physiol Gastrointest Liver Physiol 297:G135-G143, 2009.
Chu et al., "Urokinase-type plasminogen activator, receptor, and inhibitor correlating with gelatinase-B (MMP-9) contribute to inflammation in gouty arthritis of the knee," The Journal of Rhuematology 33(2):311-317, Feb. 2006.
Corrigan, "Eotaxin and asthma: some answers, more questions," Clin. Exp. Immunol. 1999 116:1-3.
Cross, "Can Probiotics Help GERD?" http://www.livestrong.com/article/474546-can-probiotics-help-gerd/, Apr. 5, 2012.
*Ex Parte Kubin,* No. 2007-0819 (B.P.A.I. May 31, 2007) ("Board Decision"), pp. 1-18 (in particular, pp. 10, 14 and 15).
Glass et al., "Mechanism Underlying Inflammation on Neurodegeneration," Cell 140(6):918-934, Mar. 19, 2010.
Guarino et al., "Increased TRPV1 gene expression in esophageal mucosa of patients with non-erosive and erosive reflux disease," Neurogastroenterol Motil 22:746-e219, 2010.
Harari et al., "NF-kB and innate immunity in ischemic stroke," National Institute of Health Public Access Author Manuscript, published in final edited form as Ann New York Academy of Science 1207: 32-40, Oct. 2010.
Hedbom et al., "Molecular aspects of pathogenesis in osteoarthritis: the role of inflammation," Cellular and Molecular Life Sciences 59(1):45-53, Jan. 2002.
Hong-Qi et al., "Current advances in the treatment of Alzheimer's disease: focused on considerations targeting AB and tau," Translational Neurodegeneration 1:21 (http://www.translationalneurodegeneration.com/content/1/1/21), 12 pages, Oct. 30, 2012.
Kemp et al., "Once-daily budesonide inhalation suspension for the treatment of persistent asthma in infants and young children," Annals of Allergy, Asthma, & Immunology, Sep. 1999, 83(3):231-239.
Lambertsen et al., "Inflammatory cytokines in experimental and human stroke," Journal of Cerebral Blood Flow & Metabolism 32:1677-1698, 2012.
Licalzi et al., "Effect of hemorrhagic hypotension and hypoventilation on lower esophageal sphincter pressure," Annals of Surgery 192(1):53-57, p. 55, para 6-p. 56, para 1, (Document entitled "Licalzi PubMed" included to establish publication date.), Jul. 1980.
Lundblad et al., "A reevaluation of the validity of unrestrained plethysmography in mice," J. Appl. Physiol. 93:1198-1207, 2002.
Martin et al., "Cognitive Function Over Time in the Alzheimer's Disease Anti-inflammatory Prevention Trial (ADAPT)," Arch Neurol. 65(7):896-905, Jul. 14, 2008.
Masters et al., "Anti-inflammatory drugs fall short in Alzheimer's disease," Nature Medicine Community Corner 14(9):916, Sep. 2008.
Modi et al., "A Physically-Modified Saline Suppresses Neuronal Apoptosis, Attenuates Tau Phosphorylation and Protects Memory in an Animal Model of Alzheimer's Disease," PLOS ONE, www.plosone.org, Aug. 2014: 9(8):e103606, 16 pages.
NIH (National Institute of Health, National Heart, Lung and Blood Institute), "What are the Signs and Symptoms of Cystic Fibrosis?," http://www.nhlbi.nih.gov/health/health-topics/topics/cf/signs.html, retrieved on Jan. 1, 2014.
NIH (National Institute of Health, National Heart, Lung and Blood Institute), "What is Atherosclerosis?" http://www.nhlbi.nih.gov/health/health-topics/topics/atherosclerosis, published Jul. 1, 2011, retrieved on Dec. 18, 2013.
Partridge, "Bacteria 'cause Asthma'," BBC News Health 2001, from internet on May 28, 2014, http://news.bbc.co.uk/2/hi/health/1372007.stm, 3 pages.
Peles et al., "Differential Effects of TRPV1 Antagonists in Acid-induced Excitation of Esophageal Vagal Afferent Fibers of Rats," Neuroscience 2009 161(2):515-525 (doi:10.1016/j.neuroscience.2009.03.040).
Planas et al., "Signalling pathways mediating inflammatory responses in brain ischaemia," International Symposium on Neurodegeneration and Neuroprotection, Biochemical Society Transactions 34(6):1267-1270, 2006.
Present et al., "Infliximab for the Treatment of Fistulas in Patients with Crohn's Disease," The New England Journal of Medicine 340(18):1398-1405, May 6, 1999.
Rivera et al., "Current Concepts in Antimicrobial Therapy Against Select Gram-Positive Organisms: Methicillin-Resistant *Staphylococcus aureus*, Penicillin-Resistant Pneumococci, and Vancomycin-Resistant Enterococci," Symposium on Antimicrobial Therapy, Mayo Clinic Proceedings 86(12):1230-1243, published Dec. 2011.
Sagel et al., "Induced sputum matrix metalloproteinase-9 correlates with lung function and airway inflammation in children with cystic fibrosis," Pediatr. Pulmon. 39(3):224-232, Mar. 2005.
Singh et al., "Benzimidazolone Activators of Chloride Secretion: Potential Therapeutics for Cystic Fibrosis and Chronic Obstructive Pulmonary Disease," J. Pharmacol. and Experimental Therapeutics 296(2):600-611, 2001.
Taylor, "Regulation of intestinal epithelial gene expression in hypoxia," Kidney Int. 66(2):528-531, abstract; p. 530, paragraph 3 (Document entitled "Taylor Ingenta" included to establish publication date), Aug. 2004.
Teronen et al., Annals of the New York Academy of Sciences 878:453-465, Jun. 1999.
Venken et al., Disturbed regulatory T cell homeostasis in multiple sclerosis, Trends in Molecular Medicine, 16(2):58-68, Feb. 2010.
Viviani et al., "Cytokines and neuronal channels: A molecular basis for age-related decline of neuronal function?," Experimental Gerontology 46:199-206, 2011.

(56) References Cited

OTHER PUBLICATIONS

Warheit et al., "Development of a respiratory Allergy model in male Brown Norway rats," Pulmonary immune and gene expression studies, Ann. Occup. Hyg., 46:362-364, 2002.

Whittaker et al., "Matrix Metalloproteinases and their Inhibitors—Current Status and Future Challenges," Celltransmissions 7(1):3-12, 2001.

Zhao et al., "Expression of Matrix Metalloproteinase-9 mRNA in Osteoporotic Bone Tissues," Journal of Tongii Medical University 17(1):28-31, Mar. 1997.

Andrews, "Determination of minimum inhibitory concentrations," Journal of Antimicrobial Chemotherapy vol. 48 (suppl. S1), pp. 5-16, 2001.

Baird et al., "Creatine-Kinase- and Exercise-Related Muscle Damage Implications for Muscle Performance and Recovery," Journal of Nutrition and Metabolism, 2012:1-13, Sep. 28, 2011.

Boulbou et al., "Diabetes mellitus and Lung Function," Medical Principles and Practice 2003, 12:87-91.

Boundless, "Lung Capacity and Volume," Boundless Anatomy and Physiology, Boundless, from https://www.boundless.com/physiology/textbooks/boundless-anatomy-and-physiology-textbook/the-respiratory-system-22/lung-volumes-and-capacities-209/lung-capacity-and-volume-1029-9200, downloaded Jun. 22, 2015.

Cotman et al., "Exercise builds brain health: key roles of growth factor cascades and inflammation," Trends in Neurosciences, 30(9):464-472, published online Aug. 31, 2007.

Gabbey, "What are Anaerobic Infections?," Anaerobic Infections/Definition and Patient Education, published Jun. 18, 2013, downloaded on Nov. 29, 2014, from http://www.healthline.com/health/anaerobic-infections, 3 pages.

Herz, "Overview: The Long and Winding Road to Understanding Alzheimer's Disease," Neuron, Feb. 15, 2007, 53: 477-479.

Holub et al, "Cytokines and Chemokines as Biomarkers of Community-Acquired Bacterial Infection," Mediators of Inflammation, vol. 2013, Article ID 190145, published after Mar. 26, 2013, by Hindawi publishing production, 7 pages.

Hubbard et al., "Cell signalling diversity of the Gqalpha family of heterotrimeric G proteins," Cellular Signalling 18(2):135-150, Sep. 22, 2005.

Khasnavis et al., "Protection of Dopaminergic Neurons in a Mouse Model of Parkinson's Disease by a Physically-Modified Saline Containing Charge-Stabilized Nanobubbles," The Journal of Neuroimmune Pharmacology, Oct. 11, 2013, 15 pages.

Khasnavis et al., "Suppression of Nuclear Factor-KB Activation and Inflammation in Microglia by Physically Modified Saline," The Journal of BioloQical Chemistry, Aug. 24, 2012, 287(35):29529-29542.

Kroeze et al., "G-protein-coupled receptors at a glance," Journal of Cell Science at a Glance, 114:4867-4869, 2003.

Merriam-Webster, "Electrokinetic" word definition extracted from online dictionary http://www.merriam-webster.com/dictionary/electrokinetic, Sep. 23, 2014, 1 page.

Lanka et al., "Therapy development for ALS: Lessons learned and path forward," Amyotrophic Lateral Sclerosis, 2008; 9: 131-140.

Minnesota Pollution Control Agency, "Low Dissolved Oxygen in Water," Water Quality/Impaired Waters 3.24, published Feb. 2009, 2 pages.

Mondal et al., "Protection of Tregs, Suppression of Th1 and Th17 Cells, and Amelioration of Experimental Allergic Encephalomyelitis by a Physically-Modified Saline," PloS One, Dec. 2012, 7(12)e51869, 18 pages.

Nagase et al., "Matrix Metalloproteinases," The Journal of Biological Chemistry, 274(31):21491-21494, Jul. 30, 1999.

Nickols et al., "Development of allosteric modulators of GPCRs for treatment of CNS disorders," Neurobiology of Disease 61:55-71, available online Sep. 27, 2013.

Ostrowski et al., "Pro- and anti-inflammatory cytokine balance in strenuous exercise in humans," The Journal of Physiology, Feb. 15, 1999, 515(1):287-291.

Pedersen et al., "Nasal inhalation of the glucocorticoid budesonide from a spacer for the treatment of patients with pollen rhinitis and asthma," Allergy 1990 (abstract), 45(6), 2 pages.

Petersen et al., "The anti-inflammatory effect of exercise," J. Appl. Physiol, 98:1154-1162, Apr. 2005.

Piantadosi, "Oxygenated water and athletic performance," Br. J. Sports Med., Sep. 2006, 40(9):740, published online Jul. 19, 2006.

Riley et al., "Human T Regulatory Cell Therapy: Take a Billion or So and Call Me in the Morning," Immunity 30:656-665, May 22, 2009.

Silverman et al., "Inhibition of Daptomycin by Pulmonary Surfactant: In Vitro Modeling and Clinical Impact," Journal of Infectious Diseases, Jun. 15, 2005, 191:2149-52 (published electronically May 5, 2005).

Sriram et al., "Experimental Allergic Encephalomyelitis: A Misleading Model of Multiple Sclerosis," Ann Neurol. 2005 58(6):939-45, published online Nov. 28, 2005.

Sun et al., "Role of G protein-coupled receptors in inflammation," Acta Pharmacologica Sinica, 2012, 33:342-350.

Vickers, "A Vaccine Against Alzheimer's Disease," Drugs Aging, 2002, 19:487-494.

Vliet et al., "Nitric oxide: a pro-inflammatory mediator in lung disease?," Respiratory Research 1:67-72, Aug. 15, 2000.

Watson et al., U.S. Appl. No. 12/258,210, filed Oct. 24, 2008.
Watson et al., U.S. Appl. No. 12/256,774, filed Oct. 23, 2008.
Watson et al., U.S. Appl. No. 12/257,224, filed Oct. 23, 2008.
Watson et al., U.S. Appl. No. 12/257,607, filed Oct. 24, 2008.
Watson et al., U.S. Appl. No. 12/259,101, filed Oct. 27, 2008.
Watson et al., U.S. Appl. No. 61/373,652, filed Aug. 13, 2010 (unpublished).
Wood et al., U.S. Appl. No. 13/028,058, filed Feb. 15, 2011.

Yasuda et al., Modulation of hypoglossal motoneuron excitability by NK1.

Areza-Fegyveres et al., "Dementia Puglistica with Clinical Features of Alzheimer's Disease," Arq Neuropsiquiatar, vol. 65, No. 3-B, Sao Paulo, Sep. 2007, pp. 830-833(4).

Bellucci et al., "Induction of Inflammator Mediators and Microglial Activation in Mice Transgenic for Mutant Human P3015 Tau Protein," American Journal of Pathology, vol. 165, No. 5, Nov. 2004, pp. 1643-1652(10).

Kim et al., "Microglia, major player in the brain inflammation: their roles in the pathogenesis of Perkinson's disease," Experimental and Molecular Medicine, vol. 38, No, 4, Aug. 2006, pp. 333-347(15).

Li et al., "Interleukin-1 Mediates Pathological Effects of Microglia on Tau Phosphorylation and on Synatophysin Synthesis in Cortical Neurons through a p38-MAPK Pathway," The Journal of Neuroscience, vol. 23, No. 5, Mar. 1, 2003, pp. 1605-1611(7).

Wersinger et al., "Inflammation and Parkinson's Disease," Current Drug Targets—Inflammation & Allergy, vol. 1, No. 3, Sep. 2002, pp. 221-242(22).

Yoshiyama et al., "Synapse Loss and Microglial Activation Precede Tangles in a P301S Taupathy Mouse Model," Neuron, vol. 53, No. 3, Feb. 1, 2007, pp. 337-351(15).

Arnold et al., "ICAM-1 expression and low-molecular-weight G-protein activation of human bronchial epithelial cells (A549) infected with RSV," Journal of Leukocyte Biology, vol. 60, No. 6, Dec. 1996, 766-771.

Agarwal et al., "Principle and applications of microbubble and nanobubble technology for water treatment," Chemosphere, 84(9):117-1180, Aug. 2011.

Bettelli et al., "Induction and effector functions of TH17 cells," Nature, 453(7198), Jun. 19, 2008, pp. 1051-1057.

Chaplin, "Evidence for Nanobubbles," Nanobubbles (ultrafine bubbles) in Water Structure and Science, Nov. 6, 2015, pp. 1-12, retrieved from the internet at http://www1.lsbu.ac.uk/water/nanobubble.html#evid on Dec. 9, 2015.

Drugbank, "Budesonide", retrieved from the Internet at < http://www.drugbank.ca/drugs/DB01222 > in Nov. 2015, 9 pages.

Lee et al., "Phosphatidylinositol-3-kinase activation blocks amyloid beta-induced neurotoxicity," Toxicology, 243 (1-2):43-50, published in print Jan. 14, 2008, available online Sep. 26, 2007.

Lundblad et al., "Penh is not a measure of airway resistance!," European Respiratory Journal, Oct. 1, 2007, 47:805.

(56) References Cited

OTHER PUBLICATIONS

Ushikubo et al., "Evidence of the existence and the stability of nano-bubbles in water," Colloids and Surfaces A: Physicochemical and Engineering Aspects, 361(1-3):31-37, May 20, 2010.

Valmori et al., "Human RORYgt+ TH17 cells preferentially differentiate from naive FOXP3+Treg in the presence of lineage-specific polarizing factor," Proceedings of the National Academy of Science 45:19402-19407, 2010.

"Know the 10 Signs," Alzheimer's Association. 2 pages. Downloaded on Feb. 22, 2016 from <http://www.alz.org/national/documents/checklist_10signs.pdf>. 2009.

Behan et al., "The sad plight of multiple sclerosis research (low on fact, high on fiction): critical data to support it being a neurocristopathy," Inflammopharmacology, 18(6). pp. 265-290. Dec. 2010. Published ahead of print Sep. 24, 2010.

Bird, "Genetic aspects of Alzheimer disease." Genetics in Medicine, 10(4):231-239. Apr. 2008.

* cited by examiner

COMPOSITIONS AND METHODS FOR TREATMENT OF TAUPATHY

CROSS-REFERENCE TO RELATED APPLICATIONS

This application claims the benefit of priority to U.S. Provisional Patent Application Ser. No. 61/373,223 filed Aug. 12, 2010, which is incorporated by reference herein in its entirety.

FIELD OF THE INVENTION

Particular aspects relate generally to inflammatory neurodegenerative diseases (e.g., multiple sclerosis, amyotrophic lateral sclerosis, Alzheimer's disease, Parkinson's disease, stroke/cerebral ischemia, head trauma, spinal cord injury, Huntington's disease, migraine, cerebral amyloid angiopathy, inflammatory neurodegenerative condition associated with AIDS, age-related cognitive decline; taupathies, mild cognitive impairment and prion diseases in a mammal), and in more particular aspects to taupathies (e.g., Alzheimer's, argyorphilic grain disease, frontotemporal dementia, progressive supranuclear palsy, corticobasal degeneration, frontotemporal lobar degeneration (Pick's disease), and Dementia pugilistica (DP) (a.k.a., boxer's dementia, chronic boxer's encephalopathy)), and to regulating or modulating neuroinflammation, and more particularly to compositions and methods for treating or preventing taupathies or at least one symptom of taupathy disease in a subject by administering a therapeutic composition comprising at least one electrokinetically-generated fluids (e.g., electrokinetically-generated gas-enriched fluids) as disclosed herein, including gas-enriched (e.g., oxygen enriched) electrokinetically generated fluids, as disclosed herein. Additional aspects relate to combination therapies.

SEQUENCE LISTING

A Sequence Listing comprising SEQ ID NO:1 is incorporated by reference herein in its entirety as part of this application.

BACKGROUND OF THE INVENTION

Neurodegenerative diseases are a group of diseases typified by deterioration of neurons or their myelin sheath. This destruction of neurons eventually leads to dysfunction and disabilities. Often times inflammation is found to be a component of neurodegenerative diseases and adds to the pathogenesis of the neurodegeneration (Minagar, et al. (2002) J. Neurological Sci. 202:13-23; Antel and Owens (1999) J. Neuroimmunol. 100: 181-189; Elliott (2001) Mol. Brain. Res. 95:172-178; Nakamura (2002) Biol. Pharm. Bull. 25:945-953; Whitton P S. (2007) Br J Pharmacol. 150:963-76). Collectively, these diseases comprise the art-recognized inflammatory neurodegenerative diseases. Neuroinflammation may occur years prior to any considerable loss of neurons in some neurodegenerative disorders (Tansey et. al., Fron Bioscience 13:709-717, 2008). Many different types of immune cells, including macrophages, neutrophils, T cells, astrocytes, and microglia, can contributed to the pathology of immune-related diseases, like Multiple Sclerosis (M.S.), Parkinson's disease, amyloidosis (e.g., Alzheimer's disease), amyotrophic lateral sclerosis (ALS), prion diseases, and HIV-associated dementia. More specifically, research groups have noted that in MS the injury to myelin is mediated by an inflammatory response (Ruffini et. al. (2004) Am J Pathol 164:1519-1522) and that M.S. pathogenesis is exacerbated when leukocytes infiltrate the CNS (Dos Santos et. al. (2008) J Neuroinflammation 5:49). One research group has developed genetic models to test CNS inflammation and its effects in MS (through the animal model experimental autoimmune encephalomyelitis (EAE). In addition, pro-inflammatory cytokines (specifically TNF-alpha) were found to be elevated in Alzheimer's disease, Parkinson's disease, and amyotrophic lateral sclerosis (ALS). (Greig et al (2006) Ann NY Acad of Sci 1035:290-315). These inflammatory neurodegenerative diseases may, therefore, be effectively treated by anti-inflammatory drugs.

Inflammatory neurodegenerative diseases include but are not limited to: multiple sclerosis (MS), Parkinson's disease, amyloidosis (e.g., Alzheimer's disease), amyotrophic lateral sclerosis (ALS), HIV-associated dementia, stroke/cerebral ischemia, head trauma, spinal cord injury, Huntington's disease, migraine, cerebral amyloid angiopathy, AIDS, age-related cognitive decline; mild cognitive impairment and prion diseases in a mammal.

Multiple sclerosis (MS) is a chronic inflammatory neurodegenerative disease of the central nervous system (CNS) that affects approximately 1,100,000 people all over the world, in particular affects young adults (Pugliatti et al. (2002) Clin. Neurol. Neuros. 104:182-191). MS is characterized pathologically by demyelination of neural tissue, which results clinically in one of many forms of the disease, ranging from benign to chronic-progressive patterns of the disease state. More specifically, five main forms of multiple sclerosis have been described: 1) benign multiple sclerosis; 2) relapsing-remitting multiple sclerosis (RRMS); 3) secondary progressive multiple sclerosis (SPMS); 4) primary progressive multiple sclerosis (PPMS); and 5) progressive-relapsing multiple sclerosis (PRMS). Chronic progressive multiple sclerosis is a term used to collectively refer to SPMS, PPMS, and PRMS. The relapsing forms of multiple sclerosis are SPMS with superimposed relapses, RRMS and PRMS.

Throughout the course of the disease there is a progressive destruction of the myelin sheath surrounding axons. Since intact myelin is essential in the preservation of axonal integrity (Dubois-Dalcq et al., Neuron. 48, 9-12 (2005)) systematic destruction eventually leads, clinically, to various neurological dysfunctions including numbness and pain, problems with coordination and balance, blindness, and general cognitive impairment. Interestingly, MS progression can differ considerably in patients with some having slight disability even after several decades of living with the disease, while others becoming dependent upon a wheelchair only a few years after being diagnosis.

The etiology of MS currently is unknown, but studies examining genetic evidence, the molecular basis, and immunology factors are beginning to elucidate the course of the disease and the mechanism by which demyelination occurs. In genetic analyses, some reports have indicated that related individuals have higher incidence of MS when compared to normal population (0.1% prevalence of MS): an identical twin having a 30% chance of developing the disease if the other twin has MS and fraternal twins and siblings have a 1-2% chance if a another sibling is affected by MS. Several groups have utilized linkage and association studies to discover the genes responsible for this heritability and found that the relative risk of being affected by MS is 3-4 fold higher to those carrying a the major histocompatibility complex (MHC) class II allele of the human leukocyte antigen (HLA)-DR2 allele. Other genes have been identified that associate with MS, but a much lower risk. The link between MS susceptibility and MHC Class II strongly suggests a role for CD4+ T-cells in the pathogenesis of MS (Oksenberg et al., *JAMA* 270:2363-2369 (1993); Olerup et al., *Tissue Antigens* 38:1-3 (1991)).

In addition, identification of genes that are differentially expressed in MS patients suffering from MS compared to healthy individuals has been attempted. Gene microarrays have been used 1) to examine transcription from MS plaque types (acute verses chronic) and plaque regions (active verses inactive) (Lock and Heller (2003)); 2) to compare peripheral blood mononucleocytes (PBMC) in RRMS patients verses controls, from patients both with and without interferon-β treatment (Sturzebecher et al. (2003)); and 3) to examine CNS cells in stages of experimental allergic encephalomyelitis (EAE) in mice, an animal model of MS (Lock et al. (2002)). Much of what these experiments discovered was expected, including the finding that anti-inflammatory, anti-apoptotic genes are down-regulated and pro-inflammatory, proliferation genes are up-regulated. Surprising results include identification of potential novel targets for therapeutic application such as osteopontin (Chabas et al. 2001) and TRAIL (Wandinger et al. 2003)). However, many of the genes that have differential regulation when comparing expression from MS patients with healthy individuals have unknown significance in MS development, because any genes that may affect MS susceptibility and/or progression are still unknown.

Further research has determined that inflammatory responses initiated by autoreactive CD4+ T-cells can mediate injury to myelin (Bruck et al., *J. Neurol.* 206:181-185 (2003)). In general, it is believed that much of the damage occurring to myelin sheaths and axons during an episode of MS happens through autoreactive T cell response which produces an inflammatory response including the secretion of proinflammatory (e.g. Th1 and Th17) cytokines (Prat et al., *J. Rehabil. Res. Dev.* 39:187-199 (2002); Hemmer et al., *Nat. Rev. Neurosci.* 3:291-301 (2002)).

Treatments that currently are available for MS include glatiramer acetate, interferon-β, natalizumab, and mitoxanthrone. In general, these drugs suppress the immune system in a nonspecific fashion and only marginally limit the overall progression of disease. (Lubetzki et al. (2005), *Curr. Opin. Neurol.* 18:237-244). Thus, there exists a need for developing therapeutic strategies to better treat MS.

Glatiramer acetate is composed of glutamic acid, lysine, alanine, and tyrosine as a random polymer. Glatiramer acetate has limited effectiveness and significant side effects, for example, lump at the site of injection, chills, fever, aches, shortness of breath, rapid heartbeat and anxiety. In an important clinical study using 943 patients with primary progressive MS, glatiramer acetate failed to halt the progression of disability and the disease (Wolinsky, et al (2007) *Ann Neurol* 61:13-24).

Interferon-β is a naturally occurring protein produced by fibroblasts and part of the innate immune response. As a drug for MS, interferon-β is about 18-38% effective in reducing the rate of MS episodes. Side effects include mild ones flu-like symptoms and reactions at the site of injection and more serious (e.g., depression, seizures, and liver problems)

Mitoxantrone is a treatment for MS. It was developed as a chemotherapy treatment for use in combating cancer—working by interfering with DNA repair and synthesis and is not specific to cancer cells. Side effects from mitoxantrone can be quite severe and include nausea, vomiting, hair loss, heart damage, and immunosuppression.

Natalizumab is a humanized monoclonal antibody that targets alpha4-integren, which is a cellular adhesion molecule. Natalizumab is believed to work by keeping immune cells that cause inflammation from crossing the blood brain barrier (BBB). Side effects include fatigue, headache, nausea, colds, and allergic reactions.

Parkinson's disease, another inflammatory neurodegeneration disease, is characterized by movement disorders, including muscle rigidity and slow physical movements. Recent research into Parkinson's disease has observed that due to enhanced expression of cytokines and HLA-DR antigens it is likely that the immune response contributes to the neuronal damage (Czlonkowska et. al. (2002) *Med Sci Monit* 8:RA165-77).

Amyloidosis develops when certain proteins have altered structure and tend to bind to each building up in particular tissue and blocking the normal tissue functioning. These altered structured proteins are called amyloids. Often amyloidoses is split into two categories: primary or secondary. Primary amyloidoses occur from an illness with improper immune cell function. Secondary amyloidoses usually arise from a complication of some other chronic infectious or inflammatory diseases. Examples of such include Alzheimer's disease and rheumatoid arthritis. Since the underlying problem in secondary amyloidosis is inflammation, treating inflammation likely will be beneficial.

Alzheimer's disease is another type of inflammatory neurodegenerative disease. It is exemplified by the increasing impairment of learning and memory, although the disease may manifest itself in other ways indicating altered cognitive ability. Throughout the disease the progressive loss of neurons and synapses in the cerebral cortex leads to gross atrophy of the neural tissue. Although the cause of Alzheimer's is unknown, many believe that inflammation plays an important role and clinical studies have shown that inflammation considerably contributes to the pathogenesis of the disease (Akiyama, et. al. (2000) Neurobiol Aging. 21:383-421.

In amyotrophic lateral sclerosis, a link between inflammation and the disease has been suggested (Centonze, et. al. (2007) *Trends Pharm Sci* 28:180-7). In addition, TNF-alpha mRNA has been found to be expressed in spinal cords of a transgenic mouse model for amyotrophic lateral sclerosis. Interestingly, the transcript was detected as early as prior to onset motor difficulties until death caused by ALS (Elliot (2001) *Brain Res Mol Brain Res* 95:172-8).

Tauopathies.

Tauopathies are a class of neurodegenerative diseases resulting from the pathological aggregation of tau protein in neurofibrillary tangles (NFT) in the human brain. Tau proteins are involved in stabilizing microtubules and are primarily located in neurons in the central nervous system. When tau proteins become defective, thus no longer stabilizing microtubules properly, they can result in dementias, such as Alzheimer's disease, argyorphilic grain disease, frontotemporal dementia, progressive supranuclear palsy, corticobasal degeneration, frontotemporal lobar degeneration (Pick's disease) and. dementia pugilistica (DP) (a.k.a., boxer's dementia, chronic boxer's encephalopathy) neurofibrillary tangles are at least implicated in DP). The non-Alzheimer's tauopathies listed above are sometimes grouped together as "Pick's complex".

SUMMARY OF THE INVENTION

Particular aspects provide a method for treating a taupathy or at least one symptom thereof, comprising administering to a subject in need thereof a therapeutically effective amount of an electrokinetically altered aqueous fluid comprising an ionic aqueous solution of charge-stabilized oxygen-containing nanostructures substantially having an average diameter of less than about 100 nanometers and stably configured in the ionic aqueous fluid in an amount sufficient for modulation of tau phosphorylation to provide for treating a taupathy or at least one symptom thereof in the subject. In certain aspects, the charge-stabilized oxygen-containing nanostructures are stably configured in the ionic aqueous fluid in an amount sufficient to provide, upon contact of a living cell by the fluid, modulation of at least one of cellular membrane potential and cellular membrane conductivity. In particular embodiments, the charge-stabilized oxygen-containing nanostructures are the major charge-stabilized gas-containing nanostructure species in the fluid. In certain aspects, the percentage of dissolved oxygen molecules present in the fluid as the charge-stabilized oxygen-containing nanostructures is a percentage selected from the group consisting of greater than: 0.01%, 0.1%, 1%, 5%; 10%; 15%; 20%; 25%; 30%; 35%; 40%; 45%; 50%; 55%; 60%; 65%; 70%; 75%; 80%; 85%; 90%; and 95%. In particular aspects, the total dissolved oxygen is substantially present in the charge-stabilized oxygen-containing nanostructures. In certain embodiments, the charge-stabilized oxygen-containing nanostructures substantially have an average diameter of less than a size selected from the group consisting of: 90 nm; 80 nm; 70 nm; 60 nm; 50 nm; 40 nm; 30 nm; 20 nm; 10 nm; and less than 5 nm.

In particular aspects, the ionic aqueous solution comprises a saline solution.

In particular aspects, the fluid is superoxygenated.

In particular aspects the fluid comprises a form of solvated electrons.

In particular embodiments, alteration of the electrokinetically altered aqueous fluid comprises exposure of the fluid to hydrodynamically-induced, localized electrokinetic effects. In certain aspects, exposure to the localized electrokinetic effects comprises exposure to at least one of voltage pulses and current pulses. In particular aspects, the exposure of the fluid to hydrodynamically-induced, localized electrokinetic effects, comprises exposure of the fluid to electrokinetic effect-inducing structural features of a device used to generate the fluid.

In certain aspects, the taupathy the taupathy comprises at least one selected from the group consisting of Alzheimer's, argyorphilic grain disease, frontotemporal dementia, progressive supranuclear palsy, corticobasal degeneration, frontotemporal lobar degeneration (Pick's disease), and Dementia pugilistica (DP) (a.k.a., boxer's dementia, chronic boxer's encephalopathy). Preferably, the taupathy comprises at least one argyorphilic grain disease, frontotemporal dementia, progressive supranuclear palsy, corticobasal degeneration, and frontotemporal lobar degeneration (Pick's disease). In particular embodiments, the taupathy comprises frontotemporal dementia.

In certain aspects, the at least one symptom thereof is related to at least one condition selected from the group consisting of chronic inflammation in the central nervous system and brain, and acute inflammation in the central nervous system and brain.

In particular embodiments, the electrokinetically altered aqueous fluid modulates localized or cellular levels of nitric oxide. In certain aspects, the electrokinetically altered aqueous fluid promotes a localized decrease at the site of administration of at least one cytokine selected from the group consisting of: IL-1 beta, IL-8, TNF-alpha, and TNF-beta.

Particular method aspects further comprise a synergistic or non-synergistic inhibition or reduction in inflammation by simultaneously or adjunctively treating the subject with another anti-inflammatory agent. In particular embodiments, said other anti-inflammatory agent comprises a steroid or glucocorticoid steroid (e.g., a glucocorticoid steroid comprising Budesonide or an active derivative thereof).

Particular method aspects further comprise combination therapy, wherein at least one additional therapeutic agent is administered to the patient. In certain aspects, the at least one additional therapeutic agent is selected from the group consisting of: glatiramer acetate, interferon-β, mitoxantrone, natalizumab, inhibitors of MMPs including inhibitor of MMP-9 and MMP-2, short-acting $β_2$-agonists, long-acting $β_2$-agonists, anticholinergics, corticosteroids, systemic corticosteroids, mast cell stabilizers, leukotriene modifiers, methylxanthines, $β_2$-agonists, albuterol, levalbuterol, pirbuterol, artformoterol, formoterol, salmeterol, anticholinergics including ipratropium and tiotropium; corticosteroids including beclomethasone, budesonide, flunisolide, fluticasone, mometasone, triamcinolone, methyprednisolone, prednisolone, prednisone; leukotriene modifiers including montelukast, zafirlukast, and zileuton; mast cell stabilizers including cromolyn and nedocromil; methylxanthines including theophylline; combination drugs including ipratropium and albuterol, fluticasone and salmeterol, budesonide and formoterol; antihistamines including hydroxyzine, diphenhydramine, loratadine, cetirizine, and hydrocortisone; immune system modulating drugs including tacrolimus and pimecrolimus; cyclosporine; azathioprine; mycophenolatemofetil; and combinations thereof.

In particular embodiments, the at least one additional therapeutic agent is a TSLP and/or TSLPR antagonist (e.g., wherein the TSLP and/or TSLPR antagonist is selected from the group consisting of neutralizing antibodies specific for TSLP and the TSLP receptor, soluble TSLP receptor molecules, and TSLP receptor fusion proteins, including TSLPR-immunoglobulin Fc molecules or polypeptides that encode components of more than one receptor chain).

In certain aspects, modulation of at least one of cellular membrane potential and cellular membrane conductivity comprises modulating at least one of cellular membrane structure or function comprising modulation of at least one of a conformation, ligand binding activity, or a catalytic activity of a membrane associated protein. In certain aspects, the membrane associated protein comprises at least one selected from the group consisting of receptors, transmembrane receptors, ion channel proteins, intracellular attachment proteins, cellular adhesion proteins, and integrins. In particular embodiments, the transmembrane receptor comprises a G-Protein Coupled Receptor (GPCR). In certain aspects, the G-Protein Coupled Receptor (GPCR) interacts with a G protein α subunit (e.g., wherein the G protein α subunit comprises at least one selected from the group consisting of $Gα_s$, $Gα_i$, $Gα_q$, and $Gα_{12}$).

In particular embodiments, modulating cellular membrane conductivity, comprises modulating whole-cell conductance. In certain aspects, modulating whole-cell conductance, comprises modulating at least one voltage-dependent contribution of the whole-cell conductance.

In particular aspects, modulation of at least one of cellular membrane potential and cellular membrane conductivity comprises modulating intracellular signal transduction comprising at least one of: modulation of a calcium dependant cellular messaging pathway or system; modulating intracellular signal transduction comprising modulation of phospholipase C activity; modulating intracellular signal transduction comprising modulation of adenylate cyclase (AC) activity; and modulating intracellular signal transduction associated with at least one condition or symptom selected from the group consisting of: chronic inflammation in the central nervous and brain, and acute inflammation in the central nervous and brain.

Certain aspects, comprise administration to a cell network or layer, and further comprising modulation of an intercellular junction therein. In particular embodiments, the intracellular junction comprises at least one selected from the group consisting of tight junctions, gap junctions, zona adherins and desmasomes. In certain aspects, the cell network or layers comprises at least one selected from the group consisting of endothelial cell and endothelial-astrocyte tight junctions in CNS vessels, blood-cerebrospinal fluid tight junctions or barrier, pulmonary epithelium-type junctions, bronchial epithelium-type junctions, and intestinal epithelium-type junctions.

In particular embodiments, the electrokinetically altered aqueous fluid is oxygenated, and wherein the oxygen in the fluid is present in an amount of at least 8 ppm, at least 15, ppm, at least 25 ppm, at least 30 ppm, at least 40 ppm, at least 50 ppm, or at least 60 ppm oxygen at atmospheric pressure. In certain aspects, the amount of oxygen present in charge-stabilized oxygen-containing nanostructures of the electrokinetically-altered fluid is at least 8 ppm, at least 15, ppm, at least 20 ppm, at least 25 ppm, at least 30 ppm, at least 40 ppm, at least 50 ppm, or at least 60 ppm oxygen at atmospheric pressure.

In certain aspects, the electrokinetically altered aqueous fluid comprises at least one of a form of solvated electrons, and electrokinetically modified or charged oxygen species. In certain embodiments, the form of solvated electrons or electrokinetically modified or charged oxygen species are present in an amount of at least 0.01 ppm, at least 0.1 ppm, at least 0.5 ppm, at least 1 ppm, at least 3 ppm, at least 5 ppm, at least 7 ppm, at least 10 ppm, at least 15 ppm, or at least 20 ppm. In certain aspects, the electrokinetically altered oxygenated aqueous fluid comprises solvated electrons stabilized, at least in part, by molecular oxygen.

In particular aspects, the ability to modulate of at least one of cellular membrane potential and cellular membrane conductivity persists for at least two, at least three, at least four, at least five, at least 6, at least 12 months, or longer periods, in a closed gas-tight container.

In certain aspects, the membrane associated protein comprises CCR3.

In particular aspects, treating a taupathy, or at least one symptom thereof, comprises modulation of intracellular NF-κB expression and/or activity.

Additional aspects provide a method of formulating a therapeutic agent suitable for use in treating a taupathy, or at least one symptom thereof, comprising: obtaining a therapeutic agent suitable for use in treating a taupathy, or at least one symptom thereof, of a subject; and combining the therapeutic agent with an amount of an electrokinetically altered aqueous fluid comprising an ionic aqueous solution of charge-stabilized oxygen-containing nanostructures substantially having an average diameter of less than about 100 nanometers and stably configured in the ionic aqueous fluid in an amount sufficient for treating a taupathy, or at least one symptom thereof, wherein formulating a therapeutic agent suitable for use in treating a taupathy, or at least one symptom thereof is afforded. In certain aspects, the charge-stabilized oxygen-containing nanostructures are stably configured in the ionic aqueous fluid in an amount sufficient to provide, upon contact of a living cell by the fluid, modulation of at least one of cellular membrane potential and cellular membrane conductivity.

Further aspects provide a pharmaceutical composition, comprising: a therapeutic agent suitable for use treating a taupathy, or at least one symptom thereof, of a subject; and an amount of an electrokinetically altered aqueous fluid comprising an ionic aqueous solution of charge-stabilized oxygen-containing nanostructures substantially having an average diameter of less than about 100 nanometers and stably configured in the ionic aqueous fluid in an amount sufficient for treating a taupathy, or at least one symptom thereof.

Additional aspects provide a pharmaceutical composition, prepared by the methods disclosed herein.

In certain aspects, treating comprises administration by at least one of topical, inhalation, intranasal, oral, intravenous (IV) and intraperitoneal (IP).

In particular aspects, the charge-stabilized oxygen-containing nanostructures of the electrokinetically-altered fluid comprise at least one salt or ion from Tables 1 and 2 disclosed herein.

In particular aspects, the subject is a mammal, preferably a human.

In certain aspects, treating comprises modulation of Tau phosphorylation.

DETAILED DESCRIPTION OF THE INVENTION

Figure 1:
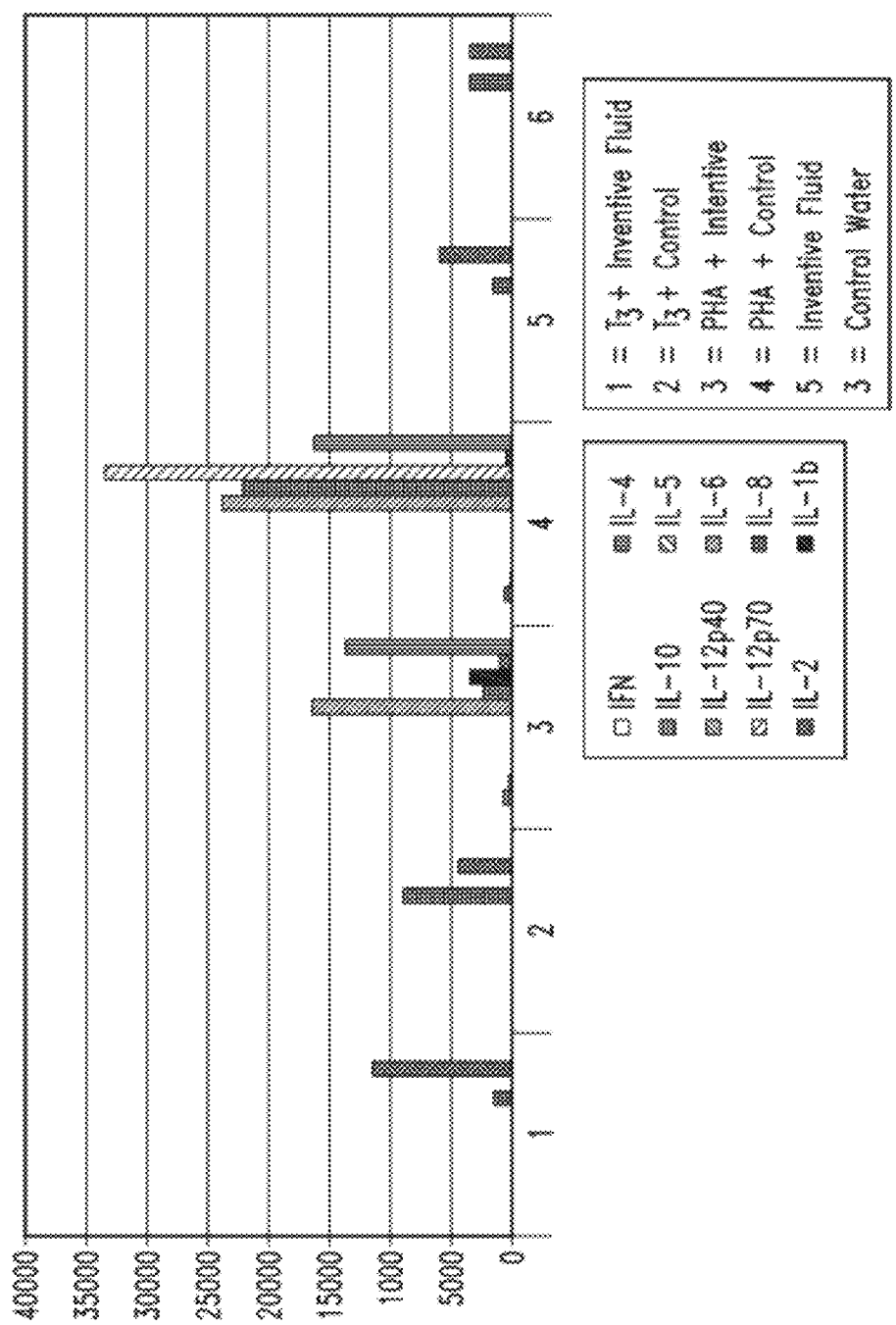
FIG. 1 illustrates the cytokine profile of a mitogenic assay in the presence of a gas-enriched fluid and deionized control fluid.

Certain embodiments disclosed herein relate to providing compositions and methods of treatment of at least one symptom of an inflammatory neurodegenerative disease, including but not limited to a taupathy (e.g., Alzheimer's, argyorphilic grain disease, frontotemporal dementia, progressive supranuclear palsy, corticobasal degeneration, frontotemporal lobar degeneration (Pick's disease), and Dementia pugilistica (DP) (a.k.a., boxer's dementia, chronic boxer's encephalopathy)), by contacting the site or administering to a subject (e.g., a mammal or human), a therapeutic composition comprising a novel electrokinetically-generated fluid. In certain specific embodiments, the electrokinetically-generated fluids comprise gas-enriched electrokinetically-generated fluid comprising oxygen-enriched water.

Tauopathies are a class of neurodegenerative diseases resulting from the pathological aggregation of tau protein in neurofibrillary tangles (NFT) in the human brain. Tau proteins are involved in stabilizing microtubules and are primarily located in neurons in the central nervous system. When tau proteins become defective, thus no longer stabilizing microtubules properly, they can result in dementias, such as Alzheimer's disease, argyorphilic grain disease, frontotemporal dementia, progressive supranuclear palsy, corticobasal degeneration, frontotemporal lobar degeneration (Pick's disease) and dementia pugilistica (DP) (a.k.a., boxer's dementia, chronic boxer's encephalopathy) neurofibrillary tangles are at least implicated in DP). The non-Alzheimer's tauopathies listed above are grouped together as "Pick's complex". According to particular aspects, the disclosed electrokinetically-generated fluids have substantial utility for treating non-Alzheimer's tauopathies or Pick's complex (e.g., argyorphilic grain disease, frontotemporal dementia, progressive supranuclear palsy, corticobasal degeneration, frontotemporal lobar degeneration (Pick's disease), DP, etc). http://en.wikipedia.org/wiki/Tauopathy—cite_note-2#cite_note-2

Argyrophilic grain disease (AGD; also called Braak's disease) is a sporadic late-onset form of dementia characterized by a neuro-degenerative process, which mainly affects limbic structures (e.g., amygdala, hippocampus and mediobasal temporal/entorhinal cortex) (see, Tolnay M et al. Argyrophilic grain disease: widespread hyperphosphorylation of tau protein in limbic neurons. Acta Neuropathol 1997; 93:477-84, which is incorporated herein in its entirety and, in particular, for its teaching of hyperphosphorylation of tau protein involvement with AGD). It is named after the silver-staining (argyrophilic) grains or coiled bodies found within the cytoplasm of neurons that consist mainly of abnormally phosphorylated tau protein isoforms having four microtubule-binding repeats (4-R tau) (Togo T et al. Argyrophilic grain disease is a sporadic 4-repeat tauopathy. J Neuropathol Exp Neurol. 2002; 61:547-56; Togo T et al. Argyrophilic grain disease: neuropathology, frequency in a dementia brain bank and lack of relationship with apolipoprotein E. Brain Pathol. 2002; 12:45-52, which are incorporated herein in their entirety and, in particular, for their teachings of tau protein involvement with AGD). Symptoms of AGD include: reduction of short-term memory, difficulty with word finding, difficulty with reading and writing, disorientation, behavioral disturbances (personality changes, emotional disorders with aggression and ill-temper). These symptoms may precede or follow memory failure. The age of onset is around 70 years old and the duration of the disease is between 4 and 8 years. Neuron degeneration likely associated with dysfunction of tau protein. Interestingly, AGD may co-exist with other tauopathies such as progressive supranuclear palsy and corticobasal degeneration (Dickson, Neuropathology of Non-Alzheimer Degenerative Disorders. Int J Clin Exp Pathol. 2010; 3(1): 1-23; which is incorporated herein in its entirety and, in particular, for its teaching of neuropathology of non-Alzheimer degenerative disorders) Currently, AGD treatments include those used for Alzheimer's disease.

Frontotemporal dementia (FTD) is a clinical syndrome caused by degeneration of the frontal lobe of the brain and may extend back to the temporal lobe. It is one of three syndromes caused by frontotemporal lobar degeneration, and the second most common early-onset dementia after Alzheimer's disease (Haberland, C (2010). "Frontotemporal dementia or frontotemporal lobar degeneration—overview of a group of proteinopathies". *Ideggyogyaszati szemle* 63 (3-4): 87-93; which is incorporated herein in its entirety and, in particular, for its teaching of neuropathology of frontotemporal dementia). Symptoms can be classified (roughly) into two groups which underlie the functions of the frontal lobe: behavioral symptoms (and/or personality change) and symptoms related to problems with executive function. Behavioral symptoms include lethargy and aspontaneity or oppositely disinhibition. Executive function is the cognitive skill of planning and organizing and as such, patients become unable to perform skills that require complex planning or sequencing. In addition, there are specific clinical manifestations of FTD, including: Primary Progressive Aphasia (PPA) and Semantic Dementia (SD). The age of onset is around 40 to 50 years old and the median survival time is seven years. There is no treatment for FTD.

Progressive Supranuclear Palsy (also referred to as Steele-Richardson-Olszewsky syndrome) is a disorder caused by damage to certain nerve cells in the brain, characterized by progressive lack of coordination, stiffness of the neck and trunk, difficulties with eye movement, slow movements, cognitive dysfunction, and difficulty walking that can result in falls. PSP belongs to the 4R tauopathies (aggregation of tau isoforms with 4 repeats) (Sergeant N., Wattez A. and Delacourte A. (1999) Neurofibrillary degeneration in progressive supranuclear palsy and corticobasal degeneration: tau pathologies with exclusively exon 10 isoforms. J Neurochem 72, 1243-1249; which is herein incorporated by reference in its entirety). PSP is a very individual disease, affecting different people in different ways at different rates of progression. Early symptoms in 'classical' PSP cases involve a tendency to fall unexpectedly, usually backwards. Other common symptoms include rigidity and backward arching of the neck, and—a key diagnostic feature—the Supranuclear Palsy. This is a difficulty in 'willed' upgaze and downgaze, ie. the ability of the patient to voluntarily move their eyes up and down whilst keeping the head still. The gait of a PSP patient is mildly unsteady and broad based. PSP is a disorder characterised by symptoms similar to Parkinson's disease (including unsteady gait, stiff movements and mild dementia). PSP can be easily misdiagnosed as Parkinson's disease in its early stages. Tiny, cramped handwriting and some changes in personality are often other indicators of the disease. Cognitive symptoms include reduced verbal fluency, attention deficit, executive dysfunction, slowing of information processing and problems with complex and abstract thought. Nevertheless the patient is still very much aware of what is going on. Behavioural changes include emotional liability and temper outbursts. Motor symptoms come first and always precede cognitive changes. The progression of the disease is slow between 5 to 10 years. The age of onset is typically over 50 years old and the duration of the disease is 7 years. Treatment is aimed at controlling symptoms. There is no known cure for progressive supranuclear palsy. Levodopa and anticholinergic medications may provide temporary reduction of symptoms.

Corticobasal degeneration (CBD) or Corticobasal Ganglionic Degeneration (CBGD) is a rare progressive neurodegenerative disease involving the cerebral cortex and the basal ganglia. It is characterized by marked disorders in movement and cognitive dysfunction. Clinical diagnosis is difficult, as symptoms of CBD are often similar to those of other diseases, such as Parkinson's disease (PD) and progressive supranuclear palsy (PSP). CBD is essentially sporadic. A degeneration affecting many subcortical nuclei and spreading into the neocortex in the frontal and parietal areas with an aggregation of tau protein in affected areas within neurons and in astrocytes. Genetic risk factor is H1H1 in the tau gene. Belongs to the 4R tauopathies (aggregation of tau isoforms with 4 repeats) (Sergeant N., Wattez A. and Delacourte A. (1999) Neurofibrillary degeneration in progressive supranuclear palsy and corticobasal degeneration: tau pathologies with exclusively exon 10 isoforms. J Neurochem 72, 1243-1249; which is herein incorporated by reference in its entirety). Symptoms include signs of Parkinsonism such as poor coordination, akinesia (an absence of movements), rigidity (a resistance to imposed movement), and disequilibrium (impaired balance); and limb dystonia (abnormal muscle postures). Other symptoms such as cognitive and visual-spatial impairments, apraxia (loss of the ability to make familiar, purposeful movements), hesitant and halting speech, myoclonus, and dysphagia (difficulty swallowing) may also occur. CBD is a progressive disease, and over the course of one to several years, most people with CBD gradually worsen, with symptoms progressing to involve upper and lower extremities and other body regions. The age of onset is around 60 years old. The duration of the disease is between 5 and 10 years. Currently, there are no drugs or other therapies that can slow the progress of the disease, and very few that offer symptomatic relief. Tremor and myoclonus may be controlled somewhat with drugs such as clonazepam. Baclofen may help reduce rigidity somewhat. Levodopa and other dopaminergic drugs used in Parkinson's disease are rarely beneficial, but may help some CBD patients.

Frontotemporal lobar degeneration (FTLD) is the name for a group of clinically, pathologically and genetically heterogeneous disorders associated with atrophy in the frontal lobe and temporal lobe of the brain, with sparing of the parietal and occipital lobes. In the over 65 age group, FTLD is probably the fourth most common cause of dementia after Alzheimer's disease, Dementia with Lewy bodies and vascular dementia. In the below 65 age group, it is the second most common cause after Alzheimer's disease. In some patients the symptoms of FTLD and Alzheimer's may overlap. The pathological processes responsible for the FTLD clinical profile are heterogeneous, and mainly related to different dysfunctions of tau gene or tau protein (mutations, aggregation, abnormal production). These different abnormal processes of tau are revealed by different types of brain lesions that accumulate in the cortex of patients, and more especially in fronto-temporal areas (Pick bodies, neurofibrillary tangles, astrocytic plaques).

Dementia pugilistica (DP) is a type of neurodegenerative disease or dementia, which may affect amateur or professional boxers as well as athletes in other sports who suffer concussions. It is also called chronic boxer's encephalopathy, traumatic boxer's encephalopathy, boxer's dementia, chronic traumatic brain injury associated with boxing (CTBI-B) and punch-drunk syndrome ('punchy'), as well as a variant form, Chronic traumatic encephalopathy. Symptoms and signs of DP develop progressively over a long latent period sometimes reaching decades, with the average time of onset being about 12-16 years after the start of a career in boxing. The condition is thought to affect around 15-20% of professional boxers. The condition, which occurs in boxers who have suffered repeated blows to the head, manifests as dementia, or declining mental ability, problems with memory, and parkinsonism, or tremors and lack of coordination. It can also cause speech problems and an unsteady gait. Patients with DP may be prone to inappropriate or explosive behavior and may display pathological jealousy or paranoia. Individuals displaying these symptoms also can be characterized as "punchy", another term for a person suffering from DR The brains of DP patients atrophy and lose neurons, for example in the cerebellum. http://en.wikipedia.org/wiki/Dementia_pugilistica—cite_note-Erlanger99-0#cite_note-Erlanger99-0 Sufferers may be treated with drugs used for Alzheimer's disease and parkinsonism.

In further embodiments herein relate to the therapeutic compositions and methods of treatment for preventing or alleviating complications related to taupathies, including alleviating the symptoms of cognitive impairment, for example.

Electrokinetically-Generated Fluids:

"Electrokinetically generated fluid," as used herein, refers to Applicants' inventive electrokinetically-generated fluids generated, for purposes of the working Examples herein, by the exemplary Mixing Device described in detail herein (see also US200802190088 and WO2008/052143, both incorporated herein by reference in their entirety). The electrokinetic fluids, as demonstrated by the data disclosed and presented herein, represent novel and fundamentally distinct fluids relative to prior art non-electrokinetic fluids, including relative to prior art oxygenated non-electrokinetic fluids (e.g., pressure pot oxygenated fluids and the like). As disclosed in various aspects herein, the electrokinetically-generated fluids have unique and novel physical and biological properties including, but not limited to the following:

In particular aspects, the electrokinetically altered aqueous fluid comprise an ionic aqueous solution of charge-stabilized oxygen-containing nanostructures substantially having an average diameter of less than about 100 nanometers and stably configured in the ionic aqueous fluid in an amount sufficient to provide, upon contact of a living cell by the fluid, modulation of at least one of cellular membrane potential and cellular membrane conductivity.

In particular aspects, electrokinetically-generated fluids refers to fluids generated in the presence of hydrodynamically-induced, localized (e.g., non-uniform with respect to the overall fluid volume) electrokinetic effects (e.g., voltage/current pulses), such as device feature-localized effects as described herein. In particular aspects said hydrodynamically-induced, localized electrokinetic effects are in combination with surface-related double layer and/or streaming current effects as disclosed and discussed herein.

In particular aspects the administered inventive electrokinetically-altered fluids comprise charge-stabilized oxygen-containing nanostructures in an amount sufficient to provide modulation of at least one of cellular membrane potential and cellular membrane conductivity. In certain embodiments, the electrokinetically-altered fluids are super-oxygenated (e.g., RNS-20, RNS-40 and RNS-60, comprising 20 ppm, 40 ppm and 60 ppm dissolved oxygen, respectively, in standard saline). In particular embodiments, the electrokinetically-altered fluids are not-superoxygenated (e.g., RNS-10 or Solas, comprising 10 ppm (e.g., approx. ambient levels of dissolved oxygen in standard saline). In certain aspects, the salinity, sterility, pH, etc., of the inventive electrokinetically-altered fluids is established at the time of electrokinetic production of the fluid, and the sterile fluids are administered by an appropriate route. Alternatively, at least one of the salinity, sterility, pH, etc., of the fluids is appropriately adjusted (e.g., using sterile saline or appropriate diluents) to be physiologically compatible with the route of administration prior to administration of the fluid. Preferably, and diluents and/or saline solutions and/or buffer compositions used to adjust at least one of the salinity, sterility, pH, etc., of the fluids are also electrokinetic fluids, or are otherwise compatible.

In particular aspects, the inventive electrokinetically-altered fluids comprise saline (e.g., one or more dissolved salt(s); e.g., alkali metal based salts (Li+, Na+, K+, Rb+, Cs+, etc.), alkaline earth based salts (e.g., Mg++, Ca++), etc., or transition metal-based positive ions (e.g., Cr, Fe, Co, Ni, Cu, Zn, etc.), in each case along with any suitable anion components, including, but not limited to F—, Cl—, Br—, I—, PO4-, SO4-, and nitrogen-based anions. Particular aspects comprise mixed salt based electrokinetic fluids (e.g., Na+, K+, Ca++, Mg++, transition metal ion(s), etc.) in various combinations and concentrations, and optionally with mixtures of counterions. In particular aspects, the inventive electrokinetically-altered fluids comprise standard saline (e.g., approx. 0.9% NaCl, or about 0.15 M NaCl). In particular aspects, the inventive electrokinetically-altered fluids comprise saline at a concentration of at least 0.0002 M, at least 0.0003 M, at least 0.001 M, at least 0.005 M, at least 0.01 M, at least 0.015 M, at least 0.1 M, at least 0.15 M, or at least 0.2 M. In particular aspects, the conductivity of the inventive electrokinetically-altered fluids is at least 10 µS/cm, at least 40 µS/cm, at least 80 µS/cm, at least 100 µS/cm, at least 150 µS/cm, at least 200 µS/cm, at least 300 µS/cm, or at least 500 µS/cm, at least 1 mS/cm, at least 5, mS/cm, 10 mS/cm, at least 40 mS/cm, at least 80 mS/cm, at least 100 mS/cm, at least 150 mS/cm, at least 200 mS/cm, at least 300 mS/cm, or at least 500 mS/cm. In particular aspects, any salt may be used in preparing the inventive electrokinetically-altered fluids, provided that they allow for formation of biologically active salt-stabilized nanostructures (e.g., salt-stabilized oxygen-containing nanostructures) as disclosed herein.

According to particular aspects, the biological effects of the inventive fluid compositions comprising charge-stabilized gas-containing nanostructures can be modulated (e.g., increased, decreased, tuned, etc.) by altering the ionic components of the fluids, and/or by altering the gas component of the fluid.

According to particular aspects, the biological effects of the inventive fluid compositions comprising charge-stabilized gas-containing nanostructures can be modulated (e.g., increased, decreased, tuned, etc.) by altering the gas component of the fluid. In preferred aspects, oxygen is used in preparing the inventive electrokinetic fluids. In additional aspects mixtures of oxygen along with at least one other gas selected from Nitrogen, Oxygen, Argon, Carbon dioxide, Neon, Helium, krypton, hydrogen and Xenon. As described above, the ions may also be varied, including along with varying the gas constitutent(s).

Given the teachings and assay systems disclosed herein (e.g., cell-based cytokine assays, patch-clamp assays, etc.) one of skill in the art will readily be able to select appropriate salts and concentrations thereof to achieve the biological activities disclosed herein.

TABLE 1

Exemplary cations and anions.

| Name | Formula | Other name(s) | | |
|---|---|---|---|---|
| Common Cations: | | | | |
| Aluminum | $Al^{+3}$ | | | |
| Ammonium | $NH_4^+$ | | | |
| Barium | $Ba^{+2}$ | | | |
| Calcium | $Ca^{+2}$ | | | |
| Chromium(II) | $Cr^{+2}$ | Chromous | | |
| Chromium(III) | $Cr^{+3}$ | Chromic | | |
| Copper(I) | $Cu^+$ | Cuprous | | |
| Copper(II) | $Cu^{+2}$ | Cupric | | |
| Iron(II) | $Fe^{+2}$ | Ferrous | | |
| Iron(III) | $Fe^{+3}$ | Ferric | | |
| Hydrogen | $H^+$ | | | |
| Hydronium | $H_3O^+$ | | | |
| Lead(II) | $Pb^{+2}$ | | | |
| Lithium | $Li^+$ | | | |
| Magnesium | $Mg^{+2}$ | | | |
| Manganese(II) | $Mn^{+2}$ | Manganous | | |
| Manganese(III) | $Mn^{+3}$ | Manganic | | |
| Mercury(I) | $Hg_2^{+2}$ | Mercurous | | |
| Mercury(II) | $Hg^{+2}$ | Mercuric | | |
| Nitronium | $NO_2^+$ | | | |
| Potassium | $K^+$ | | | |
| Silver | $Ag^+$ | | | |
| Sodium | $Na^+$ | | | |
| Strontium | $Sr^{+2}$ | | | |
| Tin(II) | $Sn^{+2}$ | Stannous | | |
| Tin(IV) | $Sn^{+4}$ | Stannic | | |
| Zinc | $Zn^{+2}$ | | | |
| Common Anions: | | | | |
| Simple ions: | | | | |
| Hydride | $H^-$ | Oxide | $O^{2-}$ | |
| Fluoride | $F^-$ | Sulfide | $S^{2-}$ | |
| Chloride | $Cl^-$ | Nitride | $N^{3-}$ | |
| Bromide | $Br^-$ | | | |
| Iodide | $I^-$ | | | |
| Oxoanions: | | | | |
| Arsenate | $AsO_4^{3-}$ | Phosphate | $PO_4^{3-}$ | |
| Arsenite | $AsO_3^{3-}$ | Hydrogen phosphate | $HPO_4^{2-}$ | |
| | | Dihydrogen phosphate | $H_2PO_4^-$ | |
| Sulfate | $SO_4^{2-}$ | Nitrate | $NO_3^-$ | |
| Hydrogen sulfate | $HSO_4^-$ | Nitrite | $NO_2^-$ | |
| Thiosulfate | $S_2O_3^{2-}$ | | | |
| Sulfite | $SO_3^{2-}$ | | | |
| Perchlorate | $ClO_4^-$ | Iodate | $IO_3^-$ | |
| Chlorate | $ClO_3^-$ | Bromate | $BrO_3^-$ | |
| Chlorite | $ClO_2^-$ | | | |

TABLE 1-continued

Exemplary cations and anions.

| Name | Formula | Other name(s) | |
|---|---|---|---|
| Hypochlorite | $OCl^-$ | Hypobromite | $OBr^-$ |
| Carbonate | $CO_3^{2-}$ | Chromate | $CrO_4^{2-}$ |
| Hydrogen carbonate or Bicarbonate | $HCO_3^-$ | Dichromate | $Cr_2O_7^{2-}$ |
| Anions from Organic Acids: | | | |
| Acetate | $CH_3COO^-$ | formate | $HCOO^-$ |
| Others: | | | |
| Cyanide | $CN^-$ | Amide | $NH_2^-$ |
| Cyanate | $OCN^-$ | Peroxide | $O_2^{2-}$ |
| Thiocyanate | $SCN^-$ | Oxalate | $C_2O_4^{2-}$ |
| Hydroxide | $OH^-$ | Permanganate | $MnO_4^-$ |

TABLE 2

Exemplary cations and anions.

| Formula | Charge | Name |
|---|---|---|
| Monoatomic Cations | | |
| $H^+$ | 1+ | hydrogen ion |
| $Li^+$ | 1+ | lithium ion |
| $Na^+$ | 1+ | sodium ion |
| $K^+$ | 1+ | potassium ion |
| $Cs^+$ | 1+ | cesium ion |
| $Ag^+$ | 1+ | silver ion |
| $Mg^{2+}$ | 2+ | magnesium ion |
| $Ca^{2+}$ | 2+ | calcium ion |
| $Sr^{2+}$ | 2+ | strontium ion |
| $Ba^{2+}$ | 2+ | barium ion |
| $Zn^{2+}$ | 2+ | zinc ion |
| $Cd^{2+}$ | 2+ | cadmium ion |
| $Al^{3+}$ | 3+ | aluminum ion |
| Polyatomic Cations | | |
| $NH_4^+$ | 1+ | ammonium ion |
| $H_3O^+$ | 1+ | hydronium ion |
| Multivalent Cations | | |
| $Cr^{2+}$ | 2 | chromium(II) or chromous ion |
| $Cr^{3+}$ | 3 | chromium(III) or chromic ion |
| $Mn^{2+}$ | 2 | manganese(II) or manganous ion |
| $Mn^{4+}$ | 4 | manganese(IV) ion |
| $Fe^{2+}$ | 2 | iron(II) or ferrous ion |
| $Fe^{3+}$ | 3 | iron(III) or ferric ion |
| $Co^{2+}$ | 2 | cobalt(II) or cobaltous ion |
| $Co^{3+}$ | 3 | cobalt(II) or cobaltic ion |
| $Ni^{2+}$ | 2 | nickel(II) or nickelous ion |
| $Ni^{3+}$ | 3 | nickel(III) or nickelic ion |
| $Cu^+$ | 1 | copper(I) or cuprous ion |
| $Cu^{2+}$ | 2 | copper(II) or cupric ion |
| $Sn^{2+}$ | 2 | tin(II) or atannous ion |
| $Sn^{4+}$ | 4 | tin(IV) or atannic ion |
| $Pb^{2+}$ | 2 | lead(II) or plumbous ion |
| $Pb^{4+}$ | 4 | lead(IV) or plumbic ion |
| Monoatomic Anions | | |
| $H^-$ | 1− | hydride ion |
| $F^-$ | 1− | fluoride ion |
| $Cl^-$ | 1− | chloride ion |
| $Br^-$ | 1− | bromide ion |
| $I^-$ | 1− | iodide ion |
| $O^{2-}$ | 2− | oxide ion |
| $S^{2-}$ | 2− | sulfide ion |
| $N^{3-}$ | 3− | nitride ion |
| Polyatomic Anions | | |
| $OH^-$ | 1− | hydroxide ion |
| $CN^-$ | 1− | cyanide ion |
| $SCN^-$ | 1− | thiocyanate ion |
| $C_2H_3O_2^-$ | 1− | acetate ion |

TABLE 2-continued

Exemplary cations and anions.

| Formula | Charge | Name |
|---|---|---|
| $ClO^-$ | 1− | hypochlorite ion |
| $ClO_2^-$ | 1− | chlorite ion |
| $ClO_3^-$ | 1− | chlorate ion |
| $ClO_4^-$ | 1− | perchlorate ion |
| $NO_2^-$ | 1− | nitrite ion |
| $NO_3^-$ | 1− | nitrate ion |
| $MnO_4^{2-}$ | 2− | permanganate ion |
| $CO_3^{2-}$ | 2− | carbonate ion |
| $C_2O_4^{2-}$ | 2− | oxalate ion |
| $CrO_4^{2-}$ | 2− | chromate ion |
| $Cr_2O_7^{2-}$ | 2− | dichromate ion |
| $SO_3^{2-}$ | 2− | sulfite ion |
| $SO_4^{2-}$ | 2− | sulfate ion |
| $PO_3^{3-}$ | 3− | phosphite ion |
| $PO_4^{3-}$ | 3− | phosphate ion |

The present disclosure sets forth novel gas-enriched fluids, including, but not limited to gas-enriched ionic aqueous solutions, aqueous saline solutions (e.g., standard aqueous saline solutions, and other saline solutions as discussed herein and as would be recognized in the art, including any physiological compatible saline solutions), cell culture media (e.g., minimal medium, and other culture media) useful in the treatment of diabetes or diabetes related disorders. A medium, or media, is termed "minimal" if it only contains the nutrients essential for growth. For prokaryotic host cells, a minimal media typically includes a source of carbon, nitrogen, phosphorus, magnesium, and trace amounts of iron and calcium. (Gunsalus and Stanter, The Bacteria, V. 1, Ch. 1 Acad. Press Inc., N.Y. (1960)). Most minimal media use glucose as a carbon source, ammonia as a nitrogen source, and orthophosphate (e.g., $PO_4$) as the phosphorus source. The media components can be varied or supplemented according to the specific prokaryotic or eukaryotic organism(s) grown, in order to encourage optimal growth without inhibiting target protein production. (Thompson et al., *Biotech. and Bioeng.* 27: 818-824 (1985)).

In particular aspects, the electrokinetically altered aqueous fluids are suitable to modulate $^{13}$C-NMR line-widths of reporter solutes (e.g., Trehelose) dissolved therein. NMR line-width effects are in indirect method of measuring, for example, solute 'tumbling' in a test fluid as described herein in particular working Examples.

In particular aspects, the electrokinetically altered aqueous fluids are characterized by at least one of: distinctive square wave voltammetry peak differences at any one of −0.14V, −0.47V, −1.02V and −1.36V; polarographic peaks at −0.9 volts; and an absence of polarographic peaks at −0.19 and −0.3 volts, which are unique to the electrokinetically generated fluids as disclosed herein in particular working Examples.

In particular aspects, the electrokinetically altered aqueous fluids are suitable to alter cellular membrane conductivity (e.g., a voltage-dependent contribution of the whole-cell conductance as measure in patch clamp studies disclosed herein).

In particular aspects, the electrokinetically altered aqueous fluids are oxygenated, wherein the oxygen in the fluid is present in an amount of at least 15, ppm, at least 25 ppm, at least 30 ppm, at least 40 ppm, at least 50 ppm, or at least 60 ppm dissolved oxygen at atmospheric pressure. In particular aspects, the electrokinetically altered aqueous fluids have less than 15 ppm, less that 10 ppm of dissolved oxygen at atmospheric pressure, or approximately ambient oxygen levels.

In particular aspects, the electrokinetically altered aqueous fluids are oxygenated, wherein the oxygen in the fluid is present in an amount between approximately 8 ppm and approximately 15 ppm, and in this case is sometimes referred to herein as "Solas."

In particular aspects, the electrokinetically altered aqueous fluid comprises at least one of solvated electrons (e.g., stabilized by molecular oxygen), and electrokinetically modified and/or charged oxygen species, and wherein in certain embodiments the solvated electrons and/or electrokinetically modified or charged oxygen species are present in an amount of at least 0.01 ppm, at least 0.1 ppm, at least 0.5 ppm, at least 1 ppm, at least 3 ppm, at least 5 ppm, at least 7 ppm, at least 10 ppm, at least 15 ppm, or at least 20 ppm.

In particular aspects, the electrokinetically altered aqueous fluids are characterized by differential (e.g., increased or decreased) permittivity relative to control, non-electrokinetically altered fluids. In preferred aspects, the electrokinetically altered aqueous fluids are characterized by differential, increased permittivity relative to control, non-electrokinetically altered fluids. Permittivity (∈) (farads per meter) is a measure of the ability of a material to be polarized by an electric field and thereby reduce the total electric field inside the material. Thus, permittivity relates to a material's ability to transmit (or "permit") an electric field. Capacitance (C) (farad; coulomb per volt), a closely related property, is a measure of the ability of a material to hold charge if a voltage is applied across it (e.g., best modeled by a dielectric layer sandwiched between two parallel conductive plates). If a voltage V is applied across a capacitor of capacitance C, then the charge Q that it can hold is directly proportional to the applied voltage V, with the capacitance C as the proportionality constant. Thus, Q=CV, or C=Q/V. The capacitance of a capacitor depends on the permittivity E of the dielectric layer, as well as the area A of the capacitor and the separation distance d between the two conductive plates. Permittivity and capacitance are mathematically related as follows: C=∈(A/d). When the dielectric used is vacuum, then the capacitance Co=∈o (A/d), where co is the permittivity of vacuum (8.85×10$^{-12}$ F/m). The dielectric constant (k), or relative permittivity of a material is the ratio of its permittivity ∈ to the permittivity of vacuum ∈o, so k=∈/∈o (the dielectric constant of vacuum is 1). A low-k dielectric is a dielectric that has a low permittivity, or low ability to polarize and hold charge. A high-k dielectric, on the other hand, has a high permittivity. Because high-k dielectrics are good at holding charge, they are the preferred dielectric for capacitors. High-k dielectrics are also used in memory cells that store digital data in the form of charge.

In particular aspects, the electrokinetically altered aqueous fluids are suitable to alter cellular membrane structure or function (e.g., altering of a conformation, ligand binding activity, or a catalytic activity of a membrane associated protein) sufficient to provide for modulation of intracellular signal transduction, wherein in particular aspects, the membrane associated protein comprises at least one selected from the group consisting of receptors, transmembrane receptors (e.g., G-Protein Coupled Receptor (GPCR), TSLP receptor, beta 2 adrenergic receptor, bradykinin receptor, etc.), ion channel proteins, intracellular attachment proteins, cellular adhesion proteins, and integrins. In certain aspects, the effected G-Protein Coupled Receptor (GPCR) interacts with a G protein α subunit (e.g., $G\alpha_s$, $G\alpha_i$, $G\alpha_g$, and $G\alpha_{12}$).

In particular aspects, the electrokinetically altered aqueous fluids are suitable to modulate intracellular signal transduction, comprising modulation of a calcium dependant cellular messaging pathway or system (e.g., modulation of phospholipase C activity, or modulation of adenylate cyclase (AC) activity).

In particular aspects, the electrokinetically altered aqueous fluids are characterized by various biological activities (e.g., regulation of cytokines, receptors, enzymes and other proteins and intracellular signaling pathways) described in the working Examples and elsewhere herein.

In particular aspects, the electrokinetically altered aqueous fluids display synergy with glatiramer acetate interferon-β, mitoxantrone, and/or natalizumab. In particular aspects, the electrokinetically altered aqueous fluids reduce DEP-induced TSLP receptor expression in bronchial epithelial cells (BEC) as shown in working Examples herein.

In particular aspects, the electrokinetically altered aqueous fluids inhibit the DEP-induced cell surface-bound MMP9 levels in bronchial epithelial cells (BEC) as shown in working Examples herein.

In particular aspects, the biological effects of the electrokinetically altered aqueous fluids are inhibited by diphtheria toxin, indicating that beta blockade, GPCR blockade and Ca channel blockade affects the activity of the electrokinetically altered aqueous fluids (e.g., on regulatory T cell function) as shown in working Examples herein.

In particular aspects, the physical and biological effects (e.g., the ability to alter cellular membrane structure or function sufficient to provide for modulation of intracellular signal transduction) of the electrokinetically altered aqueous fluids persists for at least two, at least three, at least four, at least five, at least 6 months, or longer periods, in a closed container (e.g., closed gas-tight container).

Therefore, further aspects provide said electrokinetically-generated solutions and methods of producing an electrokinetically altered oxygenated aqueous fluid or solution, comprising: providing a flow of a fluid material between two spaced surfaces in relative motion and defining a mixing volume therebetween, wherein the dwell time of a single pass of the flowing fluid material within and through the mixing volume is greater than 0.06 seconds or greater than 0.1 seconds; and introducing oxygen ($O_2$) into the flowing fluid material within the mixing volume under conditions suitable to dissolve at least 20 ppm, at least 25 ppm, at least 30, at least 40, at least 50, or at least 60 ppm oxygen into the material, and electrokinetically alter the fluid or solution. In certain aspects, the oxygen is infused into the material in less than 100 milliseconds, less than 200 milliseconds, less than 300 milliseconds, or less than 400 milliseconds. In particular embodiments, the ratio of surface area to the volume is at least 12, at least 20, at least 30, at least 40, or at least 50.

Yet further aspects, provide a method of producing an electrokinetically altered oxygenated aqueous fluid or solution, comprising: providing a flow of a fluid material between two spaced surfaces defining a mixing volume therebetween; and introducing oxygen into the flowing material within the mixing volume under conditions suitable to infuse at least 20 ppm, at least 25 ppm, at least 30, at least 40, at least 50, or at least 60 ppm oxygen into the material in less than 100 milliseconds, less than 200 milliseconds, less than 300 milliseconds, or less than 400 milliseconds. In certain aspects, the dwell time of the flowing material within the mixing volume is greater than 0.06 seconds or greater than 0.1 seconds. In particular embodiments, the ratio of surface area to the volume is at least 12, at least 20, at least 30, at least 40, or at least 50.

Additional embodiments provide a method of producing an electrokinetically altered oxygenated aqueous fluid or solution, comprising use of a mixing device for creating an output mixture by mixing a first material and a second material, the device comprising: a first chamber configured to receive the first material from a source of the first material; a stator; a rotor having an axis of rotation, the rotor being disposed inside the stator and configured to rotate about the axis of rotation therein, at least one of the rotor and stator having a plurality of through-holes; a mixing chamber defined between the rotor and the stator, the mixing chamber being in fluid communication with the first chamber and configured to receive the first material therefrom, and the second material being provided to the mixing chamber via the plurality of through-holes formed in the one of the rotor and stator; a second chamber in fluid communication with the mixing chamber and configured to receive the output material therefrom; and a first internal pump housed inside the first chamber, the first internal pump being configured to pump the first material from the first chamber into the mixing chamber. In certain aspects, the first internal pump is configured to impart a circumferential velocity into the first material before it enters the mixing chamber.

Further embodiments provide a method of producing an electrokinetically altered oxygenated aqueous fluid or solution, comprising use of a mixing device for creating an output mixture by mixing a first material and a second material, the device comprising: a stator; a rotor having an axis of rotation, the rotor being disposed inside the stator and configured to rotate about the axis of rotation therein; a mixing chamber defined between the rotor and the stator, the mixing chamber having an open first end through which the first material enters the mixing chamber and an open second end through which the output material exits the mixing chamber, the second material entering the mixing chamber through at least one of the rotor and the stator; a first chamber in communication with at least a majority portion of the open first end of the mixing chamber; and a second chamber in communication with the open second end of the mixing chamber.

Additional aspects provide an electrokinetically altered oxygenated aqueous fluid or solution made according to any of the above methods. In particular aspects the administered inventive electrokinetically-altered fluids comprise charge-stabilized oxygen-containing nanostructures in an amount sufficient to provide modulation of at least one of cellular membrane potential and cellular membrane conductivity. In certain embodiments, the electrokinetically-altered fluids are superoxygenated (e.g., RNS-20, RNS-40 and RNS-60, comprising 20 ppm, 40 ppm and 60 ppm dissolved oxygen, respectively, in standard saline). In particular embodiments, the electrokinetically-altered fluids are not-superoxygenated (e.g., RNS-10 or Solas, comprising 10 ppm (e.g., approx. ambient levels of dissolved oxygen in standard saline). In certain aspects, the salinity, sterility, pH, etc., of the inventive electrokinetically-altered fluids is established at the time of electrokinetic production of the fluid, and the sterile fluids are administered by an appropriate route. Alternatively, at least one of the salinity, sterility, pH, etc., of the fluids is appropriately adjusted (e.g., using sterile saline or appropriate diluents) to be physiologically compatible with the route of administration prior to administration of the fluid. Preferably, and diluents and/or saline solutions and/or buffer compositions used to adjust at least one of the salinity, sterility, pH, etc., of the fluids are also electrokinetic fluid, or are otherwise compatible therewith.

The present disclosure sets forth novel gas-enriched fluids, including, but not limited to gas-enriched ionic aqueous solutions, aqueous saline solutions (e.g., standard aqueous saline solutions, and other saline solutions as discussed herein and as would be recognized in the art, including any physiological compatible saline solutions), cell culture media (e.g., minimal medium, and other culture media)

Inflammation

Inflammation may occur as a defensive response to invasion of the subject by foreign material, particularly of microbial origin. Additionally, mechanical trauma, toxins, and neoplasia may induce inflammatory responses. The accumulation and subsequent activation of leukocytes are central events in the pathogenesis of most forms of inflammation. Inflammation deficiencies can compromise the host, leaving it susceptible to worsening infection or trauma. Excessive inflammation, such as prolonged inflammatory responses, may lead to inflammatory diseases including but not limited to diabetes, arteriosclerosis, cataracts, chronic skin disorders, reperfusion injury, and cancer, to post-infectious syndromes such as in infectious meningitis, rheumatic fever, and to rheumatic diseases such as systemic lupus erythematosus and rheumatoid arthritis. These diseases affect millions of people worldwide every year, and lead to increased mortality and morbidity. The commonality of the inflammatory response in these varied disease processes makes its regulation a major element in the prevention, or treatment of human disease.

Overproduction of pro-inflammatory cytokines has been implicated in the pathogenesis of numerous inflammatory and autoimmune diseases. Secretion of TNFα is a primary event in the initiation of the inflammatory cascade (Brennan F. M., et. al. *Lancet*, 1989, 2:244-7; Haworth C, et. al. *Eur. J. Immunol*. 1991, 21:2575-2579) and directly contributes to the initiation and maintenance of these diseases. Other cytokines also play a role, including interleukin 1β (IL-1β), IL-6, IL-8, IL-12 nitric oxide (NO), IFN-γ, granulocyte colony stimulating factor (G-CSF), granulocyte macrophage-colony stimulating factor (GM-CSF), and IL-10. Certain of these cytokines (e.g. IL-8) may increase or exacerbate an inflammatory response, while others (e.g. IL-10) may decrease or alleviate the inflammatory response.

Cells of the immune system, macrophages in particular, secrete many of these cytokines in response to activating stimuli. Target cells of the cytokines may be localized in any body compartment and may act via long-distance mechanisms, or may act on neighboring cells. Thus, cytokines may regulate inflammation in a localized or systemic manner.

Metalloproteinases

Metalloproteinases are a superfamily of proteinases (enzymes) classified into families and subfamilies as described, for example, in N. M. Hooper FEBS Letters 354:1-6, 1994. Examples of metalloproteinases include the matrix metalloproteinases (MMPs) such as the collagenases (MMP1, MMP8, MMP13), the gelatinases (MMP2, MMP9), the stromelysins (MMP3, MMP10, MMP II), matrilysin (MMP7), metalloelastase (MMP12), enamelysin (MMP19), the MT-MMPs (MMP14, MMP15, MMP16, MMP17); the reprolysin or adamalysin or MDC family which includes the secretases and sheddases such as TNF converting enzymes (ADAM10 and TACE); the astacin family which include enzymes such as procollagen processing proteinase (PCP); and other metalloproteinases such as aggrecanase, the endothelin converting enzyme family and the angiotensin converting enzyme family. Collectively, the metalloproteinases are known to cleave a broad range of matrix substrates such as collagen, proteoglycan and fibronectin. Metalloproteinases are implicated in the processing, or secretion, of biological important cell mediators, such as tumour necrosis factor (TNF); and the post translational proteolysis processing, or shedding, of biologically important membrane proteins, such as the low affinity IgE receptor CD23 (see, e.g., N. M. Hooper et al., Biochem. J. 321:265-279, 1997).

Not surprisingly, therefore, metalloproteinases are believed to be important in many physiological disease processes that involve tissue remodeling (e.g., embryonic development, bone formation, uterine remodelling during menstruation, etc.). Moreover, inhibition of the activity of one or more metalloproteinases may well be of benefit in these diseases or conditions, for example: various inflammatory and allergic diseases such as, inflammation of the joint (especially rheumatoid arthritis, osteoarthritis and gout), inflammation of the gastro-intestinal tract (especially inflammatory bowel disease, ulcerative colitis and gastritis), inflammation of the skin (especially psoriasis, eczema, dermatitis); in tumour metastasis or invasion; in disease associated with uncontrolled degradation of the extracellular matrix such as osteoarthritis; in bone resorptive disease (such as osteoporosis and Paget's disease); in diseases associated with aberrant angiogenesis; the enhanced collagen remodelling associated with diabetes, periodontal disease (such as gingivitis), corneal ulceration, ulceration of the skin, post-operative conditions (such as colonic anastomosis) and dermal wound healing; demyelinating diseases of the central and peripheral nervous systems (such as multiple sclerosis); Alzheimer's disease; extracellular matrix remodelling observed in cardiovascular diseases such as restenosis and atherosclerosis; asthma; rhinitis; and chronic obstructive pulmonary diseases (COPED).

MMP12, also known as macrophage elastase or metalloelastase, was initially cloned in the mouse (Shapiro et al., Journal of Biological Chemistry 267: 4664, 1992) and has also been cloned in man by the same group in 1995. MMP12 is preferentially expressed in activated macrophages, and has been shown to be secreted from alveolar macrophages from smokers (Shapiro et al, 1993, Journal of Biological Chemistry, 268: 23824) as well as in foam cells in atherosclerotic lesions (Matsumoto et al, Am. J. Pathol. 153: 109, 1998). A mouse model of COPD is based on challenge of mice with cigarette smoke for six months, two cigarettes a day six days a week. Wild-type mice developed pulmonary emphysema after this treatment. When MMP12 knock-out mice were tested in this model they developed no significant emphysema, strongly indicating that MMP12 is a key enzyme in the COPD pathogenesis. The role of MMPs such as MMP12 in COPD (emphysema and bronchitis) is discussed in Anderson and Shinagawa, 1999, Current Opinion in Anti-inflammatory and Immunomodulatory Investigational Drugs 1(1): 29-38. It was recently discovered that smoking increases macrophage infiltration and macrophage-derived MMP-12 expression in human carotid artery plaques (Matetzky S, Fishbein M C et al., Circulation 102:(18), 36-39 Suppl. S, Oct. 31, 2000).

MMP9-(Gelatinase B; 92 kDa-TypeIV Collagenase; 92 kDa Gelatinase) is a secreted protein which was first purified, then cloned and sequenced, in 1989 (S. M. Wilhelm et al., J. Biol. Chem. 264 (29): 17213-17221, 1989; published erratum in J. Biol. Chem. 265 (36): 22570, 1990) (for review of detailed information and references on this protease see T. H. Vu & Z. Werb (1998) (In: Matrix Metalloproteinases, 1998, edited by W. C. Parks & R. P. Mecham, pp. 115-148, Academic Press. ISBN 0-12-545090-7). The expression of MMP9 is restricted normally to a few cell types, including trophoblasts, osteoclasts, neutrophils and macrophages (Vu & Werb, supra). However, the expression can be induced in these same cells and in other cell types by several mediators, including exposure of the cells to growth factors or cytokines. These are the same mediators often implicated in initiating an inflammatory response. As with other secreted MMPs, MMP9 is released as an inactive Pro-enzyme, which is subsequently cleaved to form the enzymatically active enzyme. The proteases required for this activation in vivo are not known. The balance of active MMP9 versus inactive enzyme is further regulated in vivo by interaction with TIMP-1 (Tissue Inhibitor of Metalloproteinases-1), a naturally-occurring protein. TIMP-1 binds to the C-terminal region of MMP9, leading to inhibition of the catalytic domain of MMP9. The balance of induced expression of ProMMP9, cleavage of Pro- to active MMP9 and the presence of TIMP-1 combine to determine the amount of catalytically active MMP9 which is present at a local site. Proteolytically active MMP9 attacks substrates which include gelatin, elastin, and native Type IV and Type V collagens; it has no activity against native Type I collagen, proteoglycans or laminins. There has been a growing body of data implicating roles for MMP9 in various physiological and pathological processes. Physiological roles include the invasion of embryonic trophoblasts through the uterine epithelium in the early stages of embryonic implantation; some role in the growth and development of bones; and migration of inflammatory cells from the vasculature into tissues.

MMP9 release, measured using enzyme immunoassay, was significantly enhanced in fluids and in AM supernatants from untreated asthmatics compared with those from other populations (Am. J. Resp. Cell & Mol. Biol., 5:583-591, 1997). Also, increased MMP9 expression has been observed in certain other pathological conditions, thereby implicating MMP9 in disease processes such as COPD, arthritis, tumour metastasis, Alzheimer's disease, multiple sclerosis, and plaque rupture in atherosclerosis leading to acute coronary conditions such as myocardial infarction (see also WO07087637A3, incorporated herein by reference).

Recently, it has been demonstrated that the levels of MMP-9 are significantly increased in patients with stable asthma and even higher in patients with acute asthmatic patients compared with healthy control subjects. MMP-9 plays a crucial role in the infiltration of airway inflammatory cells and the induction of airway hyperresponsiveness indicating that MMP-9 may have an important role in inducing and maintaining asthma (Vignola et al., Sputum metalloproteinase-9/tissue inhibitor of metalloproteinase-1 ratio correlates with airflow obstruction in asthma and chronic bronchitis, Am J Respir Crit. Care Med 158:1945-1950, 1998; Hoshino et al., Inhaled corticosteroids decrease subepithelial collagen deposition by modulation of the balance between matrix metalloproteinase-9 and tissue inhibitor of metalloproteinase-1 expression in asthma, J Allergy Clin Immunol 104:356-363, 1999; Simpson et al., Differential proteolytic enzyme activity in eosinophilic and neutrophilic asthma, Am J Respir Crit. Care Med 172:559-565, 2005; Lee et al., A murine model of toluene diisocyanate-induced asthma can be treated with matrix metalloproteinase inhibitor, J Allergy Clin Immunol 108:1021-1026, 2001; and Lee et al., Matrix metalloproteinase inhibitor regulates inflammatory cell migration by reducing ICAM-1 and VCAM-1 expression in a murine model of toluene diisocyanate-induced asthma, J Allergy Clin Immunol 2003; 111:1278-1284).

MMP Inhibitors:

A number of metalloproteinase inhibitors are known (see, for example, the reviews of MMP inhibitors by Beckett R. P. and Whittaker M., 1998, Exp. Opin. Ther. Patents, 8(3): 259-282; and by Whittaker M. et al, 1999, Chemical Reviews 99(9):2735-2776). WO 02/074767 discloses hydantoin derivatives of formula that are useful as MMP inhibitors, particularly as potent MMP12 inhibitors. U.S. patent application Ser. No. 11/721,590 (published as 20080032997) discloses a further group of hydantoin derivatives that are inhibitors of metalloproteinases and are of particular interest in inhibiting MMPs such as MMP12 and MMP9. Novel triazolone derivatives for inhibiting MMPs such as MMP12 and MMP9 are disclosed in U.S. patent application Ser. No. 10/593,543 (published as 20070219217). Additional MMP12 and MMP9 inhibitors are disclosed in Ser. No. 11/509,490 (published as 20060287338) (see also Ser. No. 10/831,265 (published as 20040259896)).

Additionally, two compounds, 4-(4-phenoxyphenylsulfonyl)butane-1,2-dithiol (1) and 5-(4-phenoxyphenylsulfonyl)pentane-1,2-dithiol (2), have been shown to bind selectively and inhibit potently MMP-2 and MMP-9 (Bernardo, et. al (2002) J. Biol. Chem. 277:11201-11207). These two compounds may have significant use in the clinic to inhibit MMP-2 and -9 and therefore lessen inflammation. In addition, the use of certain tetracycline antibiotics (e.g., Minocycline and Doxycycline) at sub-antibiotic levels has been shown to effectively inhibit MMP activity. Certain aspects of this invention include using the inventive fluids in combination with sub-antibiotic levels useful to inhibit MMP.

Methods of Treatment

The term "treating" refers to, and includes, reversing, alleviating, inhibiting the progress of, or preventing a disease, disorder or condition, or one or more symptoms thereof; and "treatment" and "therapeutically" refer to the act of treating, as defined herein.

A "therapeutically effective amount" is any amount of any of the compounds utilized in the course of practicing the invention provided herein that is sufficient to reverse, alleviate, inhibit the progress of, or prevent a disease, disorder or condition, or one or more symptoms thereof.

Certain embodiments herein relate to therapeutic compositions and methods of treatment for a subject by preventing or alleviating at least one symptom of inflammation associated with certain conditions or diseases, like an inflammatory neurodegenerative disease. For example, the therapeutic compositions and/or methods disclosed herein may be useful for treating or preventing one or more condition or disease selected from the group consisting multiple sclerosis (MS), Parkinson's disease, amyloidosis (e.g. Alzheimer's disease), amyotrophic lateral sclerosis (ALS), prion diseases, and HIV-associated dementia.

Many conditions or diseases associated with inflammation have been treated with steroids, methotrexate, immunosuppressive drugs including cyclophosphamide, cyclosporine, azathioprine and leflunomide, nonsteroidal anti-inflammatory agents such as aspirin, acetaminophen and COX-2 inhibitors, gold agents and anti-malarial treatments. These drugs have a variety of disadvantages, and adverse reactions including injection site reactions, rash, upper respiratory infections, autoimmune disorders and increased susceptibility to infections. In addition, many anti-inflammatory pharmaceutical drugs require intravenous (IV) or subcutaneous (SC) administration, as opposed to more convenient and compliant oral or topical dermal routes. Accordingly, a need still exists for the development of novel medicaments and treatment methods for conditions and diseases relating to inflammation.

Current treatments for MS include glatiramer acetate, interferon-β, mitoxantrone, and natalizumab. Glatiramer acetate is composed of glutamic acid, lysine, alanine, and tyrosine as a random polymer. Glatiramer acetate has limited effectiveness and significant side effects, for example, lump at the site of injection, chills, fever, aches, shortness of breath, rapid heartbeat and anxiety. In an important clinical study using 943 patients with primary progressive MS, glatiramer acetate failed to halt the progression of disability and the disease (Wolinsky, et al (2007) Ann Neurol 61:13-24).

Interferon-β is a naturally occurring protein produced by fibroblasts and part of the innate immune response. As a drug for MS, interferon-β is about 18-38% effective in reducing the rate of MS episodes. Side effects include mild ones flu-like symptoms and reactions at the site of injection and more serious (e.g. depression, seizures, and liver problems).

Mitoxantrone is a treatment for MS. It was developed as a chemotherapy treatment for use in battling cancer. it works by interfering with DNA repair and synthesis and is not specific to cancer cells. Side effects from mitoxantrone can be quite severe and include nausea, vomiting, hair loss, heart damage, and immunosuppression.

Natalizumab is a humanized monoclonal antibody that targets alpha4-integren, which is a cellular adhesion molecule. Natalizumab is believed to work by keeping immune cells that cause inflammation from crossing the blood brain barrier. Side effects include fatigue, headache, nausea, colds, and allergic reactions.

In general, these drugs suppress the immune system in a nonspecific fashion and only marginally limit the overall progression of disease. (Lubetzki et al. (2005), Curr. Opin. Neurol. 18:237-244). Thus, there exists a need for developing therapeutic strategies to better treat MS.

Combination Therapy:

Additional aspects provide the herein disclosed inventive methods, further comprising combination therapy, wherein at least one additional therapeutic agent is administered to the patient. In certain aspects, the at least one additional therapeutic agent is selected from the group consisting of glatiramer acetate, interferon-β, mitoxantrone, and natalizumab and/or inhibitors of MMPs.

Anti-Inflammatory Activity of the Electrokinetically-Generated Gas-Enriched Fluids and Solutions:

According to certain aspects of the present invention, the gas-enriched fluids and/or solutions disclosed herein have anti-inflammatory properties and effects, and can be used as anti-inflammatory agents for the treatment of subjects afflicted by diseases or disorders relating to inflammatory neurodegeneration. FIG. 1 shows the experimental results of cytokine profiles in stimulated lymphocytes from a healthy blood donor. As can be seen in FIG. 1, the inventive oxygen-enriched fluid (water) affected a down regulation of particular cytokines, especially IL-6, IL-8, and IL-β.

Increased production of pro-inflammatory cytokines has been implicated in the pathogenesis of numerous inflammatory and autoimmune diseases. Secretion of TNFα is a primary event in the initiation of the inflammatory cascade (Brennan F. M., et. al. Lancet, 1989, 2:244-7; Haworth C, et. al. Eur. J. Immunol. 1991, 21:2575-2579) and directly contributes to the initiation and maintenance of inflammatory and autoimmune diseases. Other pro-inflammatory cytokines also play a role, including interleukin 1β (IL-1β), IL-6, IL-8, IL-12 nitric oxide, IFN-γ and GM-CSF, while anti-inflammatory cytokines such as IL-10 may reduce disease. Cells of the immune system, macrophages in particular, secrete many of these cytokines in response to activating stimuli.

A variety of cell types are involved in the inflammatory process. Overproduction of TNFα by monocytes, macrophages and other immune cells is a key element in the pathogenesis of a multitude of diseases. Macrophages and T-cells in particular play a central role in the initiation and maintenance of the immune response. Once activated by pathological or immunogenic stimuli, macrophages respond by releasing a host of cytokines, including TNF-α, IL-1β, IL-8, IL-12, nitric oxide (NO), IL-6, GM-CSF, G-CSF, M-CSF and others. T-cells release IL-2, IL-4, INF-γ, and other inflammatory cytokines. These cytokines activate other immune cells and some can also act as independent cytotoxic agents. Excessive release of macrophage and T-cell derived inflammatory mediators can particularly lead to damage of normal cells and surrounding tissues.

Pro-inflammatory cytokines have been implicated in HIV-AIDS, and other viral infections including the cytomegalovirus, influenza virus and the herpes family of viruses. TNFα enhances the basal activity of the major immediate early enhancer/promoter of human cytomegalovirus and may play a role in reactivation of latent HCMV infection in premonocytic cells (Prosch S., et. al. *Virology* 1995, 208: 197-206).

Additionally, a number of inflammatory cytokines contribute to mortality in patients suffering from sepsis or endotoxic shock. For example, TNFα and IL-1β have a well-established central role in sepsis, septic shock and endotoxic shock. Increased levels of these cytokines are associated with fever, hypotension and shock (Smith J. W. et. al. *J. Clin. Oncol.* 1992, 10:1141-1152; Chapman P. B., et. al. *J. Clin. Oncol.* 1987, 5:1942-1951) together with the induction of gene expression for phospholipase A2 (Gronich J., et. al. *J. Clin. Invest.* 1994, 93:1224-1233) and NO synthase.

The induction of NO from smooth muscle cells mediates decreased mean arterial pressure and systemic vascular resistance during septic shock, suggesting a fundamental role for NO. Thus, therapies that target downregulatory effects on IL-8, IL-1β, and NO could be beneficial in the treatment of inflammatory diseases or disorders, including sepsis, septic shock, and endotoxic shock.

Overproduction of TNFα contributes to the clinical features of numerous autoimmune diseases such as diabetes and rheumatoid arthritis. Systemic lupus erythematosus (SLE) is also precipitated by increased IL-1β and TNFα levels. Within lupus patients, serum C-reactive protein, IL-1.beta and TNFα levels were higher than in controls, suggesting that an increased inflammatory response plays a role in the disease (Liou L. B. *Clin. Exp. Rheumatol.* 2001, 19:515-523). A study of patients with one form of SLE, neuropsychiatric lupus erythematosus (NPLE), showed that the number of peripheral blood mononuclear cells expressing mRNA for TNFα as well as the cerebrospinal fluid level of NO metabolites correlated with NPLE disease severity (Svenungsson E., et al. *Ann. Rheum. Dis.* 2001, 60:372-9).

IL-1 and TNFα play a central role in various acute as well as chronic responses in animal models. Additionally, IL-11, IFNα and IFNβ may also up-regulate inflammatory reactions. Conversely, several cytokines may be involved in down-regulation of inflammatory responses (i.e. IL-4, IL-10, IL-13, among others). As set forth in Example 1, cells contacted with the inventive gas-enriched fluid showed an increase in IFN-γ levels with T3 antigen than in the control culture media with T3 antigen, while IL-8 was lower in the inventive gas-enriched culture media with T3 antigen than in the control culture media with T3 antigen. Additionally, IL-6, IL-8, and TNF-α levels were lower in the inventive gas-enriched media with PHA, than in the control media with PHA, while IL-1β levels were lower in the inventive gas-enriched fluid with PHA when compared with control media with PHA. In the inventive gas-enriched media alone, IFN-γ levels were higher than in control media. These results are consistent with an anti-inflammatory microenvironment.

NO is recognized as a mediator and regulator of inflammatory responses. It possesses cytotoxic properties toward pathogens, but can also have deleterious effects on the subject's own tissues. (Korhonen et al., *Curr Drug Targets Inflamm Allergy* 4(4): 471-9, 2005). NO reacts with soluble guanylate cyclase to form cyclic guanosine monophosphate (cGMP), which mediates many of the effects of NO. NO can also interact with molecular oxygen and superoxide anion to produce reactive oxygen species that can modify various cellular functions. These indirect effects of NO have a significant role in inflammation, where NO is produce in high amounts by inducible NO synthase (iNOS) and reactive oxygen species are synthesized by activated inflammatory cells.

NO can be produced by keratinocytes, fibroblasts, endothelial cells, and possibly others. Some of the vascular actions of NO include vasodilation, inhibiting platelet adhesion to the vascular endothelium, inhibiting leukocyte adhesion to the vascular endothelium, and scavenging superoxides. (Shah et al., *Env. Health Persp.* v. 106 (5): 1139-1143.)

Furthermore, inhibition of NO synthesis has been shown to delay wound contraction, alter collagen organization, and alter neoepidermis thickness. (Amadeu and Costa, *J. Cutan. Pathol.* 33: 465-473, 2006.) Mast cell migration and angiogenesis in wounds is also affected by inhibition of NO. (Id.) Without being bound to any particular theory of mechanism, in certain embodiments the inventive gas-enriched fluids may be modulating localized and/or cellular NO production, or degradation, consistent with the spectrum of wound healing effects illustrated in the Examples section disclosed herein. Due to variable pathways of regulation, in certain embodiments, the inventive gas-enriched fluid may increase NO production and/or retard NO degradation, whereas in other certain embodiments, the inventive gas-enriched fluid may decrease NO production and/or hasten NO degradation.

Specifically, wounds treated with oxygen-enriched saline solution showed an increase in wound healing at days 4 through 11, and between days 3 and 11, the new epidermis in wounds treated with the oxygen-enriched saline solution migrated at two to four times as fast as the epidermis of the wounds treated with the normal saline solution, as set forth in Example 9 herein. The study also showed that between 15 and 22 days, wounds treated by the oxygen-enriched saline solution differentiated at a more rapid rate as evidenced by the earlier formation of more mature epidermal layers. At all stages, the thickening that occurs in the epidermis associated with normal healing did not occur within the wounds treated by the oxygen-enriched saline solution.

Thus, in accordance with this spectrum of wound healing effects, but without wishing to be bound by any particular theory, it is believed that the oxygen-enriched saline solution may modulate the localized and/or cellular level of NO within the wounds. NO modulates growth factors, collagen deposition, inflammation, mast cell migration, epidermal thickening, and neovascularization in wound healing. Furthermore, nitric oxide is produced by an inducible enzyme that is regulated by oxygen.

In the case of mast cell migration, differences also occurred in early and late migration for the oxygen-enriched solution. This is consistent with what is known in the art regarding inhibition of NO synthesis (Amadeu and Costa, *J. Cutan Pathol* 33: 465-473, 2006).

In the first two phases of the inflammatory process, the foreign body is either destroyed, for example, if the foreign body is an organism, or the tissue around it is loosened, for example, if it is a splinter. In the healing phase, the inflammation begins to subside; individual blood vessels and vascular patterns become normal once again; and repair of the wound commences. The three main events in the repair process are (1) formation of new connective tissue by proliferating fibroblasts; (2) regeneration of epithelium; and (3) outgrowth of new capillaries.

Even before the inflammation subsides, fibroblasts begin moving into the injured area from the surrounding normal tissue, where they usually exist in a dormant state. They migrate by an amoeboid movement along strands of fibrin and distribute themselves throughout the healing area. Once fixed into position in the injured tissue, they begin to synthesize collagen and secrete this protein, which arranges itself into fibers. The fibers orient themselves with their longitudinal axes in the direction of the greatest stress. As the collagen bundles grow in firmness, the fibroblasts gradually degenerate and attach closely to the bundles, and the injured area transforms into scar tissue.

Simultaneously with scar tissue formation, the intact epidermal cells on the edge of the wound begin to proliferate and move, as one sheet, toward the center of the injured area. As the inflammation subsides, a need for a direct supply of blood arises, and angiogenesis occurs at the wound site.

Inflammation is a complex process that involves multiple cell types. For example, mast cells release mediators that trigger an early phase of vasodilation, accompanied by the separation of endothelial cells and exposure of collagen fibers in the subendothelial layer. Fibers in the intercellular gaps that form in blood vessels trap platelets and trigger the release of mediators from these cells.

In addition to platelets, the exposed collagen fibers also interact with proteins of the plasma that filter through the pores of the dilated vessel wall, including the triggering factor of the blood-clotting cascade, increased vasodilation, increased blood vessel permeability, and chemotaxis.

Additionally, the complement cascade can be activated by several stimuli: the injured blood vessels, the proteolytic enzymes released by the damaged cells, the membrane components of any participating bacteria, and antigen-antibody complexes. Some of the activated complement components act as chemotactic factors, responsible for the influx of leukocytes into the inflamed area, while others facilitate phagocytosis and participate in cell lysis.

In addition, it is believed that the inventive gas-enriched fluids or solutions may also regulate at least one cytokine involved in at least one aspect of inflammation, the cytokine(s) including, but not limited to MAF (macrophage activating factor), MMIF (macrophage migration inhibition factor), MCF (macrophage chemotactic factor), LMIF (leukocyte migration inhibition factor), HRFs (histamine releasing factors), TF (transfer factors), interleukins (IL-1, IL-2, IL-3, IL-4, IL-5, IL-6, IL-7, IL-8, IL-9, IL-10, IL-11, IL-12, IL-13, IL-14, IL-15, etc.), TNF-α, TNF-β, interferons (IFN-α, IFN-β, IFN-γ, IFN-ζ, IFN-δ, etc.), G-CSF (granulocyte colony stimulating factor), GM-CSF (granulocyte-macrophage CSF), M-CSF (macrophage CSF), multi-CSF (IL-3), fibroblast growth factor (aFGF, bFGF), EGF (epidermal growth factor), NGF (nerve growth factor), PDGF (platelet-derived growth factor), VEGF (vascular endothelial growth factor), transforming growth factors (TGF-α, TGF-β, etc.), NAP-2 (neutrophil-activating protein 2), PF-4 (platelet factor 4), thromboglobulin, MCP-1 (monocyte chemoattractant protein 1), MCP-3, MIP-1α, MIP-1β-+ (macrophage inflammatory proteins), RANTES (regulated upon activation normal T expressed and presumably secreted chemokine), HSPs (heat shock proteins), GRPs (glucose-regulated proteins), ubiquitin, and others.

Thus, in certain embodiments, the gas-enriched fluids and/or therapeutic compositions may increase production and/or secretion of anti-inflammatory molecules or cytokines or decrease the degradation of anti-inflammatory molecules or cytokines, thereby alleviating or preventing at least one symptom of inflammation and/or inflammatory neurodegeneration. In other embodiments, the gas-enriched fluids and/or therapeutic compositions of the present invention may decrease production and/or secretion of pro-inflammatory molecules or cytokines or increase the degradation of pro-inflammatory molecules or cytokines, thereby alleviating or preventing at least one symptom of inflammation and/or inflammatory neurodegeneration.

Previous studies had shown a critical role of anti-MOG antibodies in augmentation of demyelination and worsening of EAE (experimental autoimmune encephalomyelitis), an animal model system for the human autoimmune disorder of rheumatoid arthritis. (Linington, et al. 1992. *J. Neuroimmunol.* 40:219-224). Additionally, antibodies against MOG have been implicated in the pathogenesis of multiple sclerosis. (Berger et al. *N. Engl. J. Med.* 2003 Jul. 10; 349(2): 139-45).

Figure 2:
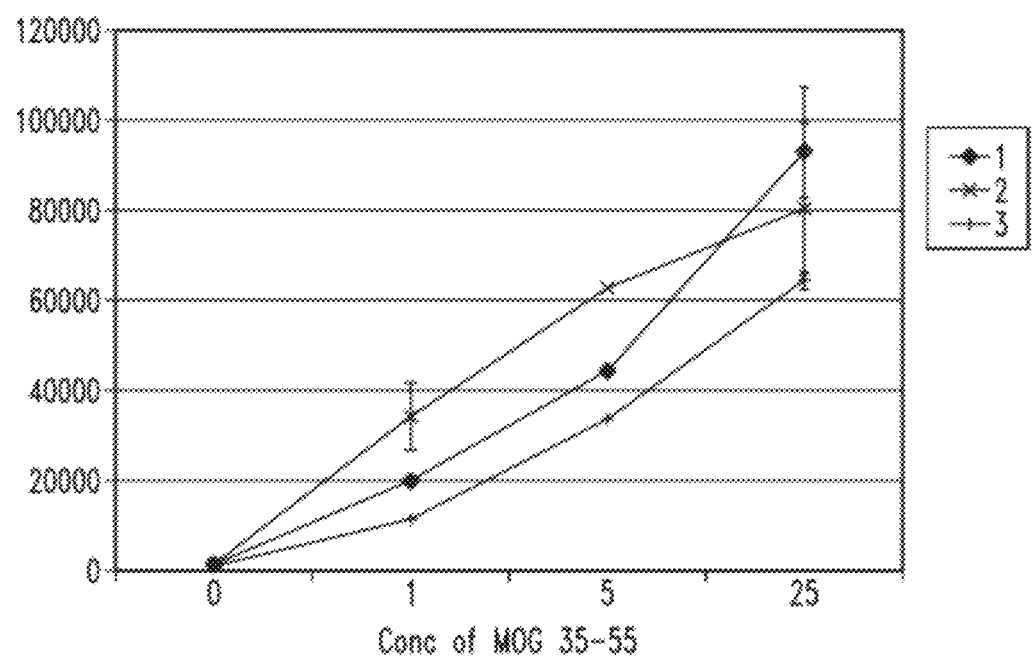
FIG. 2 illustrates the results of contacting splenocytes with MOG in the presence of pressurized pot oxygenated fluid (1), inventive gas-enriched fluid (2), or control deionized fluid (3).

As set forth in FIG. 2 and Example 3, the inventive gas-enriched fluid of the present invention amplifies the lymphocyte response to an antigen for which an animal was previously primed. As indicated in FIG. 2, lymphocyte proliferation was greater for response to MOG challenge when cultured in fluid reconstituted with the inventive gas-enriched fluid comprising solvated electrons, when compared with pressurized, oxygenated fluid (pressure pot) or control deionized fluid.

Exemplary Relevant Molecular Interactions:

Conventionally, quantum properties are thought to belong to elementary particles of less than $10^{-10}$ meters, while the macroscopic world of our everyday life is referred to as classical, in that it behaves according to Newton's laws of motion.

Recently, molecules have been described as forming clusters that increase in size with dilution. These clusters measure several micrometers in diameter, and have been reported to increase in size non-linearly with dilution. Quantum coherent domains measuring 100 nanometers in diameter have been postulated to arise in pure water, and collective vibrations of water molecules in the coherent domain may eventually become phase locked to electromagnetic field fluctuations, providing for stable oscillations in water, providing a form of 'memory' in the form of excitation of long lasting coherent oscillations specific to dissolved substances in the water that change the collective structure of the water, which may in turn determine the specific coherent oscillations that develop. Where these oscillations become stabilized by magnetic field phase coupling, the water, upon dilution may still carry 'seed' coherent oscillations. As a cluster of molecules increases in size, its electromagnetic signature is correspondingly amplified, reinforcing the coherent oscillations carried by the water.

Despite variations in the cluster size of dissolved molecules and detailed microscopic structure of the water, a specificity of coherent oscillations may nonetheless exist. One model for considering changes in properties of water is based on considerations involved in crystallization.

A simplified protonated water cluster forming a nanoscale cage is shown in Applicants' previous patent application: WO 2009/055729. A protonated water cluster typically takes the form of $H^+(H_2O)_n$. Some protonated water clusters occur naturally, such as in the ionosphere. Without being bound by any particular theory, and according to particular aspects, other types of water clusters or structures (clusters, nanocages, etc) are possible, including structures comprising oxygen and stabilized electrons imparted to the inventive output materials. Oxygen atoms may be caught in the resulting structures. The chemistry of the semi-bound nanocage allows the oxygen and/or stabilized electrons to remain dissolved for extended periods of time. Other atoms or molecules, such as medicinal compounds, can be caged for sustained delivery purposes. The specific chemistry of the solution material and dissolved compounds depend on the interactions of those materials.

Fluids processed by the mixing device have been shown previously via experiments to exhibit different structural characteristics that are consistent with an analysis of the fluid in the context of a cluster structure. See, for example, WO 2009/055729.

Charge-Stabilized Nanostructures (e.g., Charge Stabilized Oxygen-Containing Nanostructures):

As described previously in Applicants' WO 2009/055729, "Double Layer Effect," "Dwell Time," "Rate of Infusion," and "Bubble size Measurements," the electrokinetic mixing device creates, in a matter of milliseconds, a unique non-linear fluid dynamic interaction of the first material and the second material with complex, dynamic turbulence providing complex mixing in contact with an effectively enormous surface area (including those of the device and of the exceptionally small gas bubbles of less that 100 nm) that provides for the novel electrokinetic effects described herein. Additionally, feature-localized electrokinetic effects (voltage/current) were demonstrated using a specially designed mixing device comprising insulated rotor and stator features.

As well-recognized in the art, charge redistributions and/or solvated electrons are known to be highly unstable in aqueous solution. According to particular aspects, Applicants' electrokinetic effects (e.g., charge redistributions, including, in particular aspects, solvated electrons) are surprisingly stabilized within the output material (e.g., saline solutions, ionic solutions). In fact, as described herein, the stability of the properties and biological activity of the inventive electrokinetic fluids (e.g., RNS-60 or Solas) can be maintained for months in a gas-tight container, indicating involvement of dissolved gas (e.g., oxygen) in helping to generate and/or maintain, and/or mediate the properties and activities of the inventive solutions. Significantly, the charge redistributions and/or solvated electrons are stably configured in the inventive electrokinetic ionic aqueous fluids in an amount sufficient to provide, upon contact with a living cell (e.g., mammalian cell) by the fluid, modulation of at least one of cellular membrane potential and cellular membrane conductivity (see, e.g., cellular patch clamp working Example 23 from WO 2009/055729 and as disclosed herein).

As described herein under "Molecular Interactions," to account for the stability and biological compatibility of the inventive electrokinetic fluids (e.g., electrokinetic saline solutions), Applicants have proposed that interactions between the water molecules and the molecules of the substances (e.g., oxygen) dissolved in the water change the collective structure of the water and provide for nanoscale cage clusters, including nanostructures comprising oxygen and/or stabilized electrons imparted to the inventive output materials. Without being bound by mechanism, the configuration of the nanostructures in particular aspects is such that they: comprise (at least for formation and/or stability and/or biological activity) dissolved gas (e.g., oxygen); enable the electrokinetic fluids (e.g., RNS-60 or Solas saline fluids) to modulate (e.g., impart or receive) charges and/or charge effects upon contact with a cell membrane or related constituent thereof; and in particular aspects provide for stabilization (e.g., carrying, harboring, trapping) solvated electrons in a biologically-relevant form.

According to particular aspects, and as supported by the present disclosure, in ionic or saline (e.g., standard saline, NaCl) solutions, the inventive nanostructures comprise charge stabilized nanostructures (e.g., average diameter less that 100 nm) that may comprise at least one dissolved gas molecule (e.g., oxygen) within a charge-stabilized hydration-shell. According to additional aspects, the charge-stabilized hydration shell may comprise a cage or void harboring the at least one dissolved gas molecule (e.g., oxygen). According to further aspects, by virtue of the provision of suitable charge-stabilized hydration shells, the charge-stabilized nanostructure and/or charge-stabilized oxygen containing nano-structures may additionally comprise a solvated electron (e.g., stabilized solvated electron).

Without being bound by mechanism or particular theory, after the present priority date, charge-stabilized microbubbles stabilized by ions in aqueous liquid in equilibrium with ambient (atmospheric) gas have been proposed (Bunkin et al., *Journal of Experimental and Theoretical Physics,* 104:486-498, 2007; incorporated herein by reference in its entirety). According to particular aspects of the present invention, Applicants' novel electrokinetic fluids comprise a novel, biologically active form of charge-stabilized oxygen-containing nanostructures, and may further comprise novel arrays, clusters or associations of such structures.

According to the charge-stabilized microbubble model, the short-range molecular order of the water structure is destroyed by the presence of a gas molecule (e.g., a dissolved gas molecule initially complexed with a nonadsorptive ion provides a short-range order defect), providing for condensation of ionic droplets, wherein the defect is surrounded by first and second coordination spheres of water molecules, which are alternately filled by adsorptive ions (e.g., acquisition of a 'screening shell of $Na^+$ ions to form an electrical double layer) and nonadsorptive ions (e.g., $Cl^-$ ions occupying the second coordination sphere) occupying six and 12 vacancies, respectively, in the coordination spheres. In under-saturated ionic solutions (e.g., undersaturated saline solutions), this hydrated 'nucleus' remains stable until the first and second spheres are filled by six adsorptive and five nonadsorptive ions, respectively, and then undergoes Coulomb explosion creating an internal void containing the gas molecule, wherein the adsorptive ions (e.g., $Na^+$ ions) are adsorbed to the surface of the resulting void, while the nonadsorptive ions (or some portion thereof) diffuse into the solution (Bunkin et al., supra). In this model, the void in the nanostructure is prevented from collapsing by Coulombic repulsion between the ions (e.g., $Na^+$ ions) adsorbed to its surface. The stability of the void-containing nanostructures is postulated to be due to the selective adsorption of dissolved ions with like charges onto the void/bubble surface and diffusive equilibrium between the dissolved gas and the gas inside the bubble, where the negative (outward electrostatic pressure exerted by the resulting electrical double layer provides stable compensation for surface tension, and the gas pressure inside the bubble is balanced by the ambient pressure. According to the model, formation of such microbubbles requires an ionic component, and in certain aspects collision-mediated associations between particles may provide for formation of larger order clusters (arrays) (Id).

The charge-stabilized microbubble model suggests that the particles can be gas microbubbles, but contemplates only spontaneous formation of such structures in ionic solution in equilibrium with ambient air, is uncharacterized and silent as to whether oxygen is capable of forming such structures, and is likewise silent as to whether solvated electrons might be associated and/or stabilized by such structures.

According to particular aspects, the inventive electrokinetic fluids comprising charge-stabilized nanostructures and/or charge-stabilized oxygen-containing nanostructures are novel and fundamentally distinct from the postulated non-electrokinetic, atmospheric charge-stabilized microbubble structures according to the microbubble model. Significantly, this conclusion is unavoidable, deriving, at least in part, from the fact that control saline solutions do not have the biological properties disclosed herein, whereas Applicants' charge-stabilized nanostructures provide a novel, biologically active form of charge-stabilized oxygen-containing nanostructures.

According to particular aspects of the present invention, Applicants' novel electrokinetic device and methods provide for novel electrokinetically-altered fluids comprising significant quantities of charge-stabilized nanostructures in excess of any amount that may or may not spontaneously occur in ionic fluids in equilibrium with air, or in any non-electrokinetically generated fluids. In particular aspects, the charge-stabilized nanostructures comprise charge-stabilized oxygen-containing nanostructures. In additional aspects, the charge-stabilized nanostructures are all, or substantially all charge-stabilized oxygen-containing nanostructures, or the charge-stabilized oxygen-containing nanostructures the major charge-stabilized gas-containing nanostructure species in the electrokinetic fluid.

According to yet further aspects, the charge-stabilized nanostructures and/or the charge-stabilized oxygen-containing nanostructures may comprise or harbor a solvated electron, and thereby provide a novel stabilized solvated electron carrier. In particular aspects, the charge-stabilized nanostructures and/or the charge-stabilized oxygen-containing nanostructures provide a novel type of electride (or inverted electride), which in contrast to conventional solute electrides having a single organically coordinated cation, rather have a plurality of cations stably arrayed about a void or a void containing an oxygen atom, wherein the arrayed sodium ions are coordinated by water hydration shells, rather than by organic molecules. According to particular aspects, a solvated electron may be accommodated by the hydration shell of water molecules, or preferably accommodated within the nanostructure void distributed over all the cations. In certain aspects, the inventive nanostructures provide a novel 'super electride' structure in solution by not only providing for distribution/stabilization of the solvated electron over multiple arrayed sodium cations, but also providing for association or partial association of the solvated electron with the caged oxygen molecule(s) in the void—the solvated electron distributing over an array of sodium atoms and at least one oxygen atom. According to particular aspects, therefore, 'solvated electrons' as presently disclosed in association with the inventive electrokinetic fluids, may not be solvated in the traditional model comprising direct hydration by water molecules. Alternatively, in limited analogy with dried electride salts, solvated electrons in the inventive electrokinetic fluids may be distributed over multiple charge-stabilized nanostructures to provide a 'lattice glue' to stabilize higher order arrays in aqueous solution.

In particular aspects, the inventive charge-stabilized nanostructures and/or the charge-stabilized oxygen-containing nanostructures are capable of interacting with cellular membranes or constituents thereof, or proteins, etc., to mediate biological activities. In particular aspects, the inventive charge-stabilized nanostructures and/or the charge-stabilized oxygen-containing nanostructures harboring a solvated electron are capable of interacting with cellular membranes or constituents thereof, or proteins, etc., to mediate biological activities.

In particular aspects, the inventive charge-stabilized nanostructures and/or the charge-stabilized oxygen-containing nanostructures interact with cellular membranes or constituents thereof, or proteins, etc., as a charge and/or charge effect donor (delivery) and/or as a charge and/or charge effect recipient to mediate biological activities. In particular aspects, the inventive charge-stabilized nanostructures and/or the charge-stabilized oxygen-containing nanostructures harboring a solvated electron interact with cellular membranes as a charge and/or charge effect donor and/or as a charge and/or charge effect recipient to mediate biological activities.

In particular aspects, the inventive charge-stabilized nanostructures and/or the charge-stabilized oxygen-containing nanostructures are consistent with, and account for the observed stability and biological properties of the inventive electrokinetic fluids, and further provide a novel electride (or inverted electride) that provides for stabilized solvated electrons in aqueous ionic solutions (e.g., saline solutions, NaCl, etc.).

In particular aspects, the charge-stabilized oxygen-containing nanostructures substantially comprise, take the form of, or can give rise to, charge-stabilized oxygen-containing nanobubbles. In particular aspects, charge-stabilized oxygen-containing clusters provide for formation of relatively larger arrays of charge-stabilized oxygen-containing nanostructures, and/or charge-stabilized oxygen-containing nanobubbles or arrays thereof. In particular aspects, the charge-stabilized oxygen-containing nanostructures can provide for formation of hydrophobic nanobubbles upon contact with a hydrophobic surface.

In particular aspects, the charge-stabilized oxygen-containing nanostructures substantially comprise at least one oxygen molecule. In certain aspects, the charge-stabilized oxygen-containing nanostructures substantially comprise at least 1, at least 2, at least 3, at least 4, at least 5, at least 10 at least 15, at least 20, at least 50, at least 100, or greater oxygen molecules. In particular aspects, charge-stabilized oxygen-containing nanostructures comprise or give rise to nanobubbles (e.g., hydrophobic nanobubbles) of about 20 nm×1.5 nm, comprise about 12 oxygen molecules (e.g., based on the size of an oxygen molecule (approx 0.3 nm by 0.4 nm), assumption of an ideal gas and application of n=PV/RT, where P=1 atm, R=0.082□057 □·l·atm/mol·K; T=295K; V=pr$^2$h=4.7×10$^{-22}$ L, where r=10×10$^{-9}$ m, h=1.5× 10$^{-9}$ m, and n=1.95×10$^{-22}$ moles).

In certain aspects, the percentage of oxygen molecules present in the fluid that are in such nanostructures, or arrays thereof, having a charge-stabilized configuration in the ionic aqueous fluid is a percentage amount selected from the group consisting of: greater than: 0.1%; 1%; 2%; 5%; 10%; 15%; 20%; 25%; 30%; 35%; 40%; 45%; 50%; 55%; 60%; 65%; 70%; 75%; 80%; 85%; 90%; and greater than 95%. Preferably, this percentage is greater than about 5%, greater than about 10%, greater than about 15% f, or greater than about 20%. In additional aspects, the substantial size of the charge-stabilized oxygen-containing nanostructures, or arrays thereof, having a charge-stabilized configuration in the ionic aqueous fluid is a size selected from the group consisting of less than: 100 nm; 90 nm; 80 nm; 70 nm; 60 nm; 50 nm; 40 nm; 30 nm; 20 nm; 10 nm; 5 nm; 4 nm; 3 nm; 2 nm; and 1 nm. Preferably, this size is less than about 50 nm, less than about 40 nm, less than about 30 nm, less than about 20 nm, or less than about 10 nm.

In certain aspects, the inventive electrokinetic fluids comprise solvated electrons. In further aspects, the inventive electrokinetic fluids comprises charge-stabilized nanostructures and/or charge-stabilized oxygen-containing nanostructures, and/or arrays thereof, which comprise at least one of: solvated electron(s); and unique charge distributions (polar, symmetric, asymmetric charge distribution). In certain aspects, the charge-stabilized nanostructures and/or charge-stabilized oxygen-containing nanostructures, and/or arrays thereof, have paramagnetic properties.

By contrast, relative to the inventive electrokinetic fluids, control pressure pot oxygenated fluids (non-electrokinetic fluids) and the like do not comprise such electrokinetically generated charge-stabilized biologically-active nanostructures and/or biologically-active charge-stabilized oxygen-containing nanostructures and/or arrays thereof, capable of modulation of at least one of cellular membrane potential and cellular membrane conductivity.

Systems for Making Gas-Enriched Fluids

The system and methods as previously disclosed in Applicants' WO 2009/055729 patent application allow gas (e.g. oxygen) to be enriched stably at a high concentration with minimal passive loss. This system and methods can be effectively used to enrich a wide variety of gases at heightened percentages into a wide variety of fluids. By way of example only, deionized water at room temperature that typically has levels of about 2-3 ppm (parts per million) of dissolved oxygen can achieve levels of dissolved oxygen ranging from at least about 5 ppm, at least about 10 ppm, at least about 15 ppm, at least about 20 ppm, at least about 25 ppm, at least about 30 ppm, at least about 35 ppm, at least about 40 ppm, at least about 45 ppm, at least about 50 ppm, at least about 55 ppm, at least about 60 ppm, at least about 65 ppm, at least about 70 ppm, at least about 75 ppm, at least about 80 ppm, at least about 85 ppm, at least about 90 ppm, at least about 95 ppm, at least about 100 ppm, or any value greater or therebetween using the disclosed systems and/or methods. In accordance with a particular exemplary embodiment, oxygen-enriched water may be generated with levels of about 30-60 ppm of dissolved oxygen.

Table 3 illustrates various partial pressure measurements taken in a healing wound treated with an oxygen-enriched saline solution (Table 3) and in samples of the gas-enriched oxygen-enriched saline solution of the present invention.

TABLE 3

| TISSUE OXYGEN MEASUREMENTS Probe Z082BO In air: 171 mmHg 23° C. | |
|---|---|
| Column | Partial Pressure (mmHg) |
| B1 | 32-36 |
| B2 | 169-200 |

TABLE 3-continued

TISSUE OXYGEN MEASUREMENTS
Probe Z082BO
In air: 171 mmHg 23° C.

| Column | Partial Pressure (mmHg) |
|---|---|
| B3 | 20-180* |
| B4 | 40-60 |

*wound depth minimal, majority >150, occasional 20 s

Routes and Forms of Administration

In particular exemplary embodiments, the gas-enriched fluid of the present invention may function as a therapeutic composition alone or in combination with another therapeutic agent such that the therapeutic composition prevents or alleviates at least one symptom of inflammation. The therapeutic compositions of the present invention include compositions that are able to be administered to a subject in need thereof. In certain embodiments, the therapeutic composition formulation may also comprise at least one additional agent selected from the group consisting of: carriers, adjuvants, emulsifying agents, suspending agents, sweeteners, flavorings, perfumes, and binding agents.

As used herein, "pharmaceutically acceptable carrier" and "carrier" generally refer to a non-toxic, inert solid, semi-solid or liquid filler, diluent, encapsulating material or formulation auxiliary of any type. Some non-limiting examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and anti-oxidants can also be present in the composition, according to the judgment of the formulator. In particular aspects, such carriers and excipients may be gas-enriched fluids or solutions of the present invention.

The pharmaceutically acceptable carriers described herein, for example, vehicles, adjuvants, excipients, or diluents, are well known to those who are skilled in the art. Typically, the pharmaceutically acceptable carrier is chemically inert to the therapeutic agents and has no detrimental side effects or toxicity under the conditions of use. The pharmaceutically acceptable carriers can include polymers and polymer matrices, nanoparticles, microbubbles, and the like.

In addition to the therapeutic gas-enriched fluid of the present invention, the therapeutic composition may further comprise inert diluents such as additional non-gas-enriched water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, poly-ethylene glycols and fatty acid esters of sorbitan, and mixtures thereof. As is appreciated by those of ordinary skill, a novel and improved formulation of a particular therapeutic composition, a novel gas-enriched therapeutic fluid, and a novel method of delivering the novel gas-enriched therapeutic fluid may be obtained by replacing one or more inert diluents with a gas-enriched fluid of identical, similar, or different composition. For example, conventional water may be replaced or supplemented by a gas-enriched fluid produced by mixing oxygen into water or deionized water to provide gas-enriched fluid.

In certain embodiments, the inventive gas-enriched fluid may be combined with one or more therapeutic agents and/or used alone. In particular embodiments, incorporating the gas-enriched fluid may include replacing one or more solutions known in the art, such as deionized water, saline solution, and the like with one or more gas-enriched fluid, thereby providing an improved therapeutic composition for delivery to the subject.

Certain embodiments provide for therapeutic compositions comprising a gas-enriched fluid of the present invention, a pharmaceutical composition or other therapeutic agent or a pharmaceutically acceptable salt or solvate thereof, and at least one pharmaceutical carrier or diluent. These pharmaceutical compositions may be used in the prophylaxis and treatment of the foregoing diseases or conditions and in therapies as mentioned above. Preferably, the carrier must be pharmaceutically acceptable and must be compatible with, i.e. not have a deleterious effect upon, the other ingredients in the composition. The carrier may be a solid or liquid and is preferably formulated as a unit dose formulation, for example, a tablet that may contain from 0.05 to 95% by weight of the active ingredient.

Possible administration routes include oral, sublingual, buccal, parenteral (for example subcutaneous, intramuscular, intra-arterial, intraperitoneally, intracisternally, intravesically, intrathecally, or intravenous), rectal, topical including transdermal, intravaginal, intraocular, intraotical, intranasal, inhalation, and injection or insertion of implantable devices or materials.

Administration Routes

Most suitable means of administration for a particular subject will depend on the nature and severity of the disease or condition being treated or the nature of the therapy being used, as well as the nature of the therapeutic composition or additional therapeutic agent. In certain embodiments, oral or topical administration is preferred.

Formulations suitable for oral administration may be provided as discrete units, such as tablets, capsules, cachets, syrups, elixirs, chewing gum, "lollipop" formulations, microemulsions, solutions, suspensions, lozenges, or gel-coated ampules, each containing a predetermined amount of the active compound; as powders or granules; as solutions or suspensions in aqueous or non-aqueous liquids; or as oil-in-water or water-in-oil emulsions.

Additional formulations suitable for oral administration may be provided to include fine particle dusts or mists which may be generated by means of various types of metered dose pressurized aerosols, atomizers, nebulisers, or insufflators. In particular, powders or other compounds of therapeutic agents may be dissolved or suspended in a gas-enriched fluid of the present invention.

Formulations suitable for transmucosal methods, such as by sublingual or buccal administration include lozenges patches, tablets, and the like comprising the active compound and, typically a flavored base, such as sugar and acacia or tragacanth and pastilles comprising the active compound in an inert base, such as gelatin and glycerine or sucrose acacia.

Formulations suitable for parenteral administration typically comprise sterile aqueous solutions containing a predetermined concentration of the active gas-enriched fluid and possibly another therapeutic agent; the solution is preferably isotonic with the blood of the intended recipient. Additional formulations suitable for parenteral administration include formulations containing physiologically suitable co-solvents and/or complexing agents such as surfactants and cyclodextrins. Oil-in-water emulsions may also be suitable for formulations for parenteral administration of the gas-enriched fluid. Although such solutions are preferably administered intravenously, they may also be administered by subcutaneous or intramuscular injection.

Formulations suitable for urethral, rectal or vaginal administration include gels, creams, lotions, aqueous or oily suspensions, dispersible powders or granules, emulsions, dissolvable solid materials, douches, and the like. The formulations are preferably provided as unit-dose suppositories comprising the active ingredient in one or more solid carriers forming the suppository base, for example, cocoa butter. Alternatively, colonic washes with the gas-enriched fluids of the present invention may be formulated for colonic or rectal administration.

Formulations suitable for topical, intraocular, intraotic, or intranasal application include ointments, creams, pastes, lotions, pastes, gels (such as hydrogels), sprays, dispersible powders and granules, emulsions, sprays or aerosols using flowing propellants (such as liposomal sprays, nasal drops, nasal sprays, and the like) and oils. Suitable carriers for such formulations include petroleum jelly, lanolin, polyethyleneglycols, alcohols, and combinations thereof. Nasal or intranasal delivery may include metered doses of any of these formulations or others. Likewise, intraotic or intraocular may include drops, ointments, irritation fluids and the like.

Formulations of the invention may be prepared by any suitable method, typically by uniformly and intimately admixing the gas-enriched fluid optionally with an active compound with liquids or finely divided solid carriers or both, in the required proportions and then, if necessary, shaping the resulting mixture into the desired shape.

For example a tablet may be prepared by compressing an intimate mixture comprising a powder or granules of the active ingredient and one or more optional ingredients, such as a binder, lubricant, inert diluent, or surface active dispersing agent, or by molding an intimate mixture of powdered active ingredient and a gas-enriched fluid of the present invention.

Suitable formulations for administration by inhalation include fine particle dusts or mists which may be generated by means of various types of metered dose pressurized aerosols, atomizers, nebulisers, or insufflators. In particular, powders or other compounds of therapeutic agents may be dissolved or suspended in a gas-enriched fluid of the present invention.

For pulmonary administration via the mouth, the particle size of the powder or droplets is typically in the range 0.5-10 µM, preferably 1-5 µM, to ensure delivery into the bronchial tree. For nasal administration, a particle size in the range 10-500 µM is preferred to ensure retention in the nasal cavity.

Metered dose inhalers are pressurized aerosol dispensers, typically containing a suspension or solution formulation of a therapeutic agent in a liquefied propellant. In certain embodiments, as disclosed herein, the gas-enriched fluids of the present invention may be used in addition to or instead of the standard liquefied propellant. During use, these devices discharge the formulation through a valve adapted to deliver a metered volume, typically from 10 to 150 µL, to produce a fine particle spray containing the therapeutic agent and the gas-enriched fluid. Suitable propellants include certain chlorofluorocarbon compounds, for example, dichlorodifluoromethane, trichlorofluoromethane, dichlorotetrafluoroethane and mixtures thereof.

The formulation may additionally contain one or more co-solvents, for example, ethanol surfactants, such as oleic acid or sorbitan trioleate, anti-oxidants and suitable flavoring agents. Nebulisers are commercially available devices that transform solutions or suspensions of the active ingredient into a therapeutic aerosol mist either by means of acceleration of a compressed gas (typically air or oxygen) through a narrow venturi orifice, or by means of ultrasonic agitation. Suitable formulations for use in nebulisers consist of another therapeutic agent in a gas-enriched fluid and comprising up to 40% w/w of the formulation, preferably less than 20% w/w. In addition, other carriers may be utilized, such as distilled water, sterile water, or a dilute aqueous alcohol solution, preferably made isotonic with body fluids by the addition of salts, such as sodium chloride. Optional additives include preservatives, especially if the formulation is not prepared sterile, and may include methyl hydroxy-benzoate, anti-oxidants, flavoring agents, volatile oils, buffering agents and surfactants.

Suitable formulations for administration by insufflation include finely comminuted powders that may be delivered by means of an insufflator or taken into the nasal cavity in the manner of a snuff. In the insufflator, the powder is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation.

In addition to the ingredients specifically mentioned above, the formulations of the present invention may include other agents known to those skilled in the art, having regard for the type of formulation in issue. For example, formulations suitable for oral administration may include flavoring agents and formulations suitable for intranasal administration may include perfumes.

The therapeutic compositions of the invention can be administered by any conventional method available for use in conjunction with pharmaceutical drugs, either as individual therapeutic agents or in a combination of therapeutic agents.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 1000 milligrams (mg) per kilogram (kg) of body weight, with the preferred dose being 0.1 to about 30 mg/kg. According to certain aspects daily dosage of active ingredient may be 0.001 liters to 10 liters, with the preferred dose being from about 0.01 liters to 1 liter.

Dosage forms (compositions suitable for administration) contain from about 1 mg to about 500 mg of active ingredient per unit. In these pharmaceutical compositions, the active ingredient will ordinarily be present in an amount of about 0.5-95% weight based on the total weight of the composition.

Ointments, pastes, foams, occlusions, creams and gels also can contain excipients, such as starch, tragacanth, cellulose derivatives, silicones, bentonites, silica acid, and talc, or mixtures thereof. Powders and sprays also can contain excipients such as lactose, talc, silica acid, aluminum hydroxide, and calcium silicates, or mixtures of these substances. Solutions of nanocrystalline antimicrobial metals can be converted into aerosols or sprays by any of the known means routinely used for making aerosol pharmaceuticals. In general, such methods comprise pressurizing or providing a means for pressurizing a container of the solution, usually with an inert carrier gas, and passing the pressurized gas through a small orifice. Sprays can additionally contain customary propellants, such as nitrogen, carbon dioxide, and other inert gases. In addition, microspheres or nanoparticles may be employed with the gas-enriched therapeutic compositions or fluids of the present invention in any of the routes required to administer the therapeutic compounds to a subject.

The injection-use formulations can be presented in unit-dose or multi-dose sealed containers, such as ampules and vials, and can be stored in a freeze-dried (lyophilized) condition requiring only the addition of the sterile liquid excipient, or gas-enriched fluid, immediately prior to use. Extemporaneous injection solutions and suspensions can be prepared from sterile powders, granules, and tablets. The requirements for effective pharmaceutical carriers for injectable compositions are well known to those of ordinary skill in the art. See, for example, Pharmaceutics and Pharmacy Practice, J. B. Lippincott Co., Philadelphia, Pa., Banker and Chalmers, Eds., 238-250 (1982) and ASHP Handbook on Injectable Drugs, Toissel, 4th ed., 622-630 (1986).

Formulations suitable for topical administration include lozenges comprising a gas-enriched fluid of the invention and optionally, an additional therapeutic and a flavor, usually sucrose and acacia or tragacanth; pastilles comprising a gas-enriched fluid and optional additional therapeutic agent in an inert base, such as gelatin and glycerin, or sucrose and acacia; and mouth washes or oral rinses comprising a gas-enriched fluid and optional additional therapeutic agent in a suitable liquid carrier; as well as creams, emulsions, gels and the like.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Suitable pharmaceutical carriers are described in Remington's Pharmaceutical Sciences, Mack Publishing Company, a standard reference text in this field.

The dose administered to a subject, especially an animal, particularly a human, in the context of the present invention should be sufficient to effect a therapeutic response in the animal over a reasonable time frame. One skilled in the art will recognize that dosage will depend upon a variety of factors including the condition of the animal, the body weight of the animal, as well as the condition being treated.

A suitable dose is that which will result in a concentration of the therapeutic composition in a subject that is known to affect the desired response.

The size of the dose also will be determined by the route, timing and frequency of administration as well as the existence, nature, and extent of any adverse side effects that might accompany the administration of the therapeutic composition and the desired physiological effect.

It will be appreciated that the compounds of the combination may be administered: (1) simultaneously by combination of the compounds in a co-formulation or (2) by alternation, i.e. delivering the compounds serially, sequentially, in parallel or simultaneously in separate pharmaceutical formulations. In alternation therapy, the delay in administering the second, and optionally a third active ingredient, should not be such as to lose the benefit of a synergistic therapeutic effect of the combination of the active ingredients. According to certain embodiments by either method of administration (1) or (2), ideally the combination should be administered to achieve the most efficacious results. In certain embodiments by either method of administration (1) or (2), ideally the combination should be administered to achieve peak plasma concentrations of each of the active ingredients. A one pill once-per-day regimen by administration of a combination co-formulation may be feasible for some patients suffering from inflammatory neurodegenerative diseases. According to certain embodiments effective peak plasma concentrations of the active ingredients of the combination will be in the range of approximately 0.001 to 100 $\mu$M. Optimal peak plasma concentrations may be achieved by a formulation and dosing regimen prescribed for a particular patient. It will also be understood that the inventive fluids and glatiramer acetate, interferon-beta, mitoxantrone, and/or natalizumab or the physiologically functional derivatives of any thereof, whether presented simultaneously or sequentially, may be administered individually, in multiples, or in any combination thereof. In general, during alternation therapy (2), an effective dosage of each compound is administered serially, where in co-formulation therapy (1), effective dosages of two or more compounds are administered together.

The combinations of the invention may conveniently be presented as a pharmaceutical formulation in a unitary dosage form. A convenient unitary dosage formulation contains the active ingredients in any amount from 1 mg to 1 g each, for example but not limited to, 10 mg to 300 mg. The synergistic effects of the inventive fluid in combination with glatiramer acetate, interferon-beta, mitoxantrone, and/or natalizumab may be realized over a wide ratio, for example 1:50 to 50:1 (inventive fluid: glatiramer acetate, interferon-beta, mitoxantrone, and/or natalizumab). In one embodiment the ratio may range from about 1:10 to 10:1. In another embodiment, the weight/weight ratio of inventive fluid to glatiramer acetate, interferon-beta, mitoxantrone, and/or natalizumab in a co-formulated combination dosage form, such as a pill, tablet, caplet or capsule will be about 1, i.e. an approximately equal amount of inventive fluid and glatiramer acetate, interferon-beta, mitoxantrone, and/or natalizumab. In other exemplary co-formulations, there may be more or less inventive fluid and glatiramer acetate, interferon-beta, mitoxantrone, and/or natalizumab. In one embodiment, each compound will be employed in the combination in an amount at which it exhibits anti-inflammatory activity when used alone. Other ratios and amounts of the compounds of said combinations are contemplated within the scope of the invention.

A unitary dosage form may further comprise inventive fluid and glatiramer acetate, interferon-beta, mitoxantrone, and/or natalizumab, or physiologically functional derivatives of either thereof, and a pharmaceutically acceptable carrier.

It will be appreciated by those skilled in the art that the amount of active ingredients in the combinations of the invention required for use in treatment will vary according to a variety of factors, including the nature of the condition being treated and the age and condition of the patient, and will ultimately be at the discretion of the attending physician or health care practitioner. The factors to be considered include the route of administration and nature of the formulation, the animal's body weight, age and general condition and the nature and severity of the disease to be treated.

It is also possible to combine any two of the active ingredients in a unitary dosage form for simultaneous or sequential administration with a third active ingredient. The three-part combination may be administered simultaneously or sequentially. When administered sequentially, the combination may be administered in two or three administrations. According to certain embodiments the three-part combination of inventive fluid and glatiramer acetate, interferon-beta, mitoxantrone, and/or natalizumab may be administered in any order.

The following examples are meant to be illustrative only and not limiting in any way.

EXAMPLES

Example 1

Microbubble Size

Experiments were performed with a gas-enriched fluid by using the diffuser of the present invention in order to determine a gas microbubble size limit. The microbubble size limit was established by passing the gas enriched fluid through 0.22 and 0.1 micron filters. In performing these tests, a volume of fluid passed through the diffuser of the present invention and generated a gas-enriched fluid. Sixty milliliters of this fluid was drained into a 60 ml syringe. The dissolved oxygen level of the fluid within the syringe was then measured by Winkler titration. The fluid within the syringe was injected through a 0.22 micron Millipore Millex GP50 filter and into a 50 ml beaker. The dissolved oxygen rate of the material in the 50 ml beaker was then measured. The experiment was performed three times to achieve the results illustrated in Table 4 below.

TABLE 4

| DO IN SYRINGE | DO AFTER 0.22 MICRON FILTER |
|---|---|
| 42.1 ppm | 39.7 ppm |
| 43.4 ppm | 42.0 ppm |
| 43.5 ppm | 39.5 ppm |

As can be seen, the dissolved oxygen levels that were measured within the syringe and the dissolved oxygen levels within the 50 ml beaker were not significantly changed by passing the diffused material through a 0.22 micron filter, which implies that the microbubbles of dissolved gas within the fluid are not larger than 0.22 microns.

A second test was performed in which a batch of saline solution was enriched with the diffuser of the present invention and a sample of the output solution was collected in an unfiltered state. The dissolved oxygen level of the unfiltered sample was 44.7 ppm. A 0.1 micron filter was used to filter the oxygen-enriched solution from the diffuser of the present invention and two additional samples were taken. For the first sample, the dissolved oxygen level was 43.4 ppm. For the second sample, the dissolved oxygen level was 41.4 ppm. Finally, the filter was removed and a final sample was taken from the unfiltered solution. In this case, the final sample had a dissolved oxygen level of 45.4 ppm. These results were consistent with those in which the Millipore 0.22 micron filter was used. Thus, the majority of the gas bubbles or microbubbles within the saline solution are approximately less than 0.1 microns in size.

Example 2

A Cytokine Profile was Determined

Mixed lymphocytes were obtained from a single healthy volunteer donor. Buffy coat samples were washed according to standard procedures to remove platelets. Lymphocytes were plated at a concentration of $2 \times 10^6$ per plate in RPMI media (+50 mm HEPES) diluted with either inventive gas-enriched fluid or distilled water (control). Cells were stimulated with 1 microgram/mL T3 antigen, or 1 microgram/mL phytohaemagglutinin (PHA) lectin (pan-T cell activator), or unstimulated (negative control). Following 24-hour incubation, cells were checked for viability and the supernatants were extracted and frozen.

The supernatants were thawed, centrifuged, and tested for cytokine expression using a XMAP® (Luminex) bead lite protocol and platform.

Two million cells were plated into 6 wells of a 24-well plate in full RPMI+50 mm Hepes with either inventive oxygen-enriched fluid (water) (wells 1, 3, and 5) or distilled water (2, 4 and 6) (10×RPMI diluted into water to make 1×). Cells were stimulated with 1 ug/ml T3 antigen (wells 1 and 2) or PHA (wells 3 and 4). Control wells 5 and 6 were not stimulated. After 24 hours, cells were checked for viability and supernatants were collected and frozen. Next, the supernatants were thawed and spun at 8,000 g to pellet. The clarified supernatants were assayed for the cytokines listed using a LUMINEX BEAD LITE™ protocol and platform. The numerical data is tabulated in Table 5, and the corresponding bar graphs are depicted in FIG. 1. Notably, IFN-γ level was higher in the inventive gas-enriched culture media with T3 antigen than in the control culture media with T3 antigen, while IL-8 was lower in the inventive gas-enriched culture media with T3 antigen than in the control culture media with T3 antigen. Additionally, IL-6, IL-8, and TNF-α levels were lower in the inventive gas-enriched media with PHA, than in the control media with PHA, while IL-1β levels were lower in the inventive gas-enriched fluid with PHA when compared with control media with PHA. In the inventive gas-enriched media alone, IFN-γ levels were higher than in control media.

TABLE 5

| Sample | IFN | Il-10 | Il-12p40 | Il-12p70 | Il-2 | Il-4 | Il-5 | Il-6 | Il-8 | Il-ib | IP-10 | TNFa |
|---|---|---|---|---|---|---|---|---|---|---|---|---|
| 1 | 0 | 0 | 0 | 2.85 | 0 | 0 | 7.98 | 20.3 | 1350 | 7.56 | 11500 | 15.5 |
| 2 | 0 | 0 | 0 | 3.08 | 0 | 0 | 8 | 15.2 | 8940 | 3.68 | 4280 | 7.94 |
| 3 | 0 | 581 | 168 | 3.15 | 0 | 0 | 8 | 16400 | 2200 | 3280 | 862 | 13700 |
| 4 | 0 | 377 | 56.3 | 4.22 | 0 | 0 | 8.08 | 23800 | 22100 | 33600 | 558 | 16200 |
| 5 | 0 | 0 | 0 | 2.51 | 0 | 0 | 7.99 | 24 | 1330 | 7.33 | 5900 | 8.55 |
| 6 | 0 | 0 | 0 | 2.77 | 0 | 0 | 8 | 5.98 | 3210 | 4.68 | 3330 | 0 |

Example 3

Myelin Oligodendrocyte Glycoprotein (MOG)

As set forth in FIG. 2, lymphocyte proliferation in response to MOG antigenic peptide was increased when cultured in the presence of the inventive gas-enriched fluid when compared to pressurized, oxygenated fluid (pressure pot) or deionized control fluid. Thus, the inventive gas-enriched fluid amplifies the lymphocyte proliferative response to an antigen to which the cells were previously primed.

Myelin oligodendrocyte glycoprotein peptide 35-55 (MOG 35-55) (M-E-V-G-W-Y-R-S-P-F-S-R-O-V-H-L-Y-R-N-G-K) (SEQ ID NO:1; see publication US20080139674, incorporated by reference herein, including for purposes of this SEQ ID NO:1) corresponding to the known mouse sequence was synthesized. Next, $5 \times 10^5$ spleen cells were removed from MOG T cell receptor transgenic mice previously immunized with MOG, and were cultured in 0.2 ml TCM fluid reconstituted with inventive gas-enriched fluid, pressurized oxygenated water (pressure pot water) or with control deionized water. Splenocytes were cultured with MOG p35-55 for 48 or 72 hours, respectively. Cultures were pulsed with 1 Ci [3H]-thymidine and harvested 16 hours later. Mean cpm of [3H] thymidine incorporation was calculated for triplicate cultures. Results are shown in FIG. 2.

Example 4

Cytokine Expression

In particular aspects, human mixed lymphocytes were stimulated with T3 antigen or PHA in inventive electrokinetic fluid, or control fluid, and changes in IL-1β, IL-2, IL-4, IL-5, IL-6, IL-7, IL-8, IL-10, IL-12 (p40), IL-12 (p70), IL-13, IL-17, Eotaxin, IFN-γ, GM-CSF, MIP-1β, MCP-1, G-CSF, FGFb, VEGF, TNF-α, RANTES, Leptin, TNF-13, TGF-β, and NGF were evaluated. As can be seen from FIG. 1, pro-inflammatory cytokines (IL-1β, TNF-α, IL-6, and GM-CSF), chemokines (IL-8, MIP-1α, RANTES, and Eotaxin), inflammatory enzymes (iNOS, COX-2, and MMP-9), allergen responses (MHC class II, CD23, B7-1, and B7-2), and Th2 cytokines (IL-4, IL-13, and IL-5) tested were reduced in test fluid versus control fluid. By contrast, anti-inflammatory cytokines (e.g., IL1R-α, TIMPs) tested were increased in test fluid versus control fluid.

To expand on these data, Applicants used an art recognized model system involving ovalbumin sensitization, for assessing allergic hypersensitivity reactions. The end points studied were particular cytologic and cellular components of the reaction as well as serologic measurements of protein and LDH. Cytokine analysis was performed, including analysis of Eotaxin, IL-1A, IL-1B, KC, MCP-1, MCP-3, MIP-1A, RANTES, TNF-α, and VCAM.

Briefly, male Brown Norway rats were injected intraperitoneally with 0.5 mL Ovalbumin (OVA) Grade V (A5503-1G, Sigma) in solution (2.0 mg/mL) containing aluminum hydroxide (Al(OH)$_3$) (200 mg/mL) once each on days 1, 2, and 3. The study was a randomized 2×2 factorial arrangement of treatments (4 groups). After a two week waiting period to allow for an immune reaction to occur, the rats were either exposed or were treated for a week with either RDC1676-00 (sterile saline processed through the Revalesio proprietary device), and RDC1676-01 (sterile saline processed through the Revalesio proprietary device with additional oxygen added). At the end of the 1 week of treatment for once a day, the 2 groups were broken in half and 50% of the rats in each group received either Saline or OVA challenge by inhalation.

Specifically, fourteen days following the initial serialization, 12 rats were exposed to RDC 1676-00 by inhalation for 30 minutes each day for 7 consecutive days. The air flow rate through the system was set at 10 liters/minute. A total of 12 rats were aligned in the pie chamber, with a single port for nebulized material to enter and evenly distribute to the 12 sub-chambers of the Aeroneb.

Fifteen days following initial sensitization, 12 rats were exposed to RDC 1676-01 by ultrasonic nebulization for 30 minutes each day for 7 consecutive days. The air flow was also set for 10 liters/minute, using the same nebulizer and chamber. The RDC 1676-00 was nebulized first and the Aeroneb chamber thoroughly dried before RDC 1676-01 was nebulized.

Approximately 2 hours after the last nebulization treatment, 6 rats from the RDC 1676-00 group were re-challenged with OVA (1% in saline) delivered by intratracheal instillation using a Penn Century Microsprayer (Model 1A-1B). The other 6 rats from the RDC 1676-00 group were challenged with saline as the control group delivered by way of intratracheal instillation. The following day, the procedure was repeated with the RDC 1676-01 group.

Twenty four hours after re-challenge, all rats in each group were euthanized by overdose with sodium pentobarbital. Whole blood samples were collected from the inferior vena-cava and placed into two disparate blood collection tubes: Qiagen PAXgene™ Blood RNA Tube and Qiagen PAXgene™ Blood DNA Tube. Lung organs were processed to obtain bronchioalveolar lavage (BAL) fluid and lung tissue for RT-PCR to assess changes in markers of cytokine expression known to be associated with lung inflammation in this model. A unilateral lavage technique was be employed in order to preserve the integrity of the 4 lobes on the right side of the lung. The left "large" lobe was lavaged, while the 4 right lobes were tied off and immediately placed into TRI-zol™, homogenized, and sent to the lab for further processing.

BAL analysis. Lung lavage was collected and centrifuged for 10 minutes at 4° C. at 600-800 g to pellet the cells. The supernatants were transferred to fresh tubes and frozen at −80° C. Bronchial lavage fluid ("BAL") was separated into two aliquots. The first aliquot was spun down, and the supernatant was snap frozen on crushed dry ice, placed in −80° C., and shipped to the laboratory for further processing. The amount of protein and LDH present indicates the level of blood serum protein (the protein is a serum component that leaks through the membranes when it's challenged as in this experiment) and cell death, respectively. The proprietary test side showed slight less protein than the control.

The second aliquot of bronchial lavage fluid was evaluated for total protein and LDH content, as well as subjected to cytological examination. The treated group showed total cells to be greater than the saline control group. Further, there was an increase in eosinophils in the treated group versus the control group. There were also slightly different polymorphonuclear cells for the treated versus the control side.

Blood Analysis.

Whole blood was analyzed by transfer of 1.2-2.0 mL blood into a tube, and allowing it to clot for at least 30 minutes. The remaining blood sample (approximately 3.5-5.0 mL) was saved for RNA extraction using TRI-zol™ or PAXgene™. Next, the clotted blood sample was centrifuged for 10 minutes at 1200 g at room temperature. The serum (supernatant) was removed and placed into two fresh tubes, and the serum was stored at −80° C.

For RNA extraction utilizing Tri-Reagent (TB-126, Molecular Research Center, Inc.), 0.2 mL of whole blood or plasma was added to 0.75 mL of TRI Reagent BD supplemented with 20 µL of 5N acetic acid per 0.2 mL of whole blood or plasma. Tubes were shaken and stored at −80° C. Utilizing PAXgene™, tubes were incubated for approximately two hours at room temperature. Tubes were then placed on their side and stored in the −20° C. freezer for 24 hours, and then transferred to −80° C. for long term storage.

Luminex Analysis.

By Luminex platform, a microbead analysis was utilized as a substrate for an antibody-related binding reaction which is read out in luminosity units and can be compared with quantified standards. Each blood sample was run as 2 samples concurrently. The units of measurement are luminosity units and the groups are divided up into OVA challenged controls, OVA challenged treatment, and saline challenged treatment with proprietary fluid.

For Agilant gene array data generation, lung tissue was isolated and submerged in TRI Reagent (TR118, Molecular Research Center, Inc.). Briefly, approximately 1 mL of TRI Reagent was added to 50-100 mg of tissue in each tube. The samples were homogenized in TRI Reagent, using glass-Teflon™ or Polytron™ homogenizer. Samples were stored at −80° C.

In summary, this standard assay of inflammatory reaction to a known sensitization produced, at least in the blood samples, a marked clinical and serologic affect. Additionally, while significant numbers of control animals were physiologically stressed and nearly dying in the process, none of the RDC1676-01 treated group showed such clinical stress effects. This was reflected then in the circulating levels of cytokines, with approximately 30% differences between the RDC1676-01-treated and the RDC1676-01-treated groups in the OVA challenged groups. By contrast, there were small and fairly insignificant changes in cytokine, cellular and serologic profiles between the RDC1676-01-treated and the RDC1676-01-treated groups in the non-OVA challenged groups., which likely merely represent minimal baseline changes of the fluid itself.

Example 5

A Regulatory T-Cell Assay was Used to Show Effects of the Inventive Electrokinetically Generated Fluids in Modulation of T-Cell Proliferation and Elaboration of Cytokines (Il-10) and Other Proteins (e.g., GITR, Granzyme A, XCL1, pStat5, and Foxp3)) in Regulatory T-Cell Assays, and of, for Example, Tryptase in PBMC The ability of particular embodiments disclosed herein to regulate T cells was studied by irradiating antigen presenting cells, and introducing antigen and T cells. Typically, these stimulated T cells proliferate. However, upon the introduction of regulatory T cells, the usual T cell proliferation is suppressed.

Methods:

Briefly, FITC-conjugated anti-CD25 (ACT-1) antibody used in sorting was purchased from DakoCytomation (Chicago, Ill.). The other antibodies used were as follows: CD3 (HIT3a for soluble conditions), GITR (PE conjugated), CD4 (Cy-5 and FITC-conjugated), CD25 (APC-conjugated), CD28 (CD28.2 clone), CD127-APC, Granzyme A (PE-conjugated), FoxP3 (BioLegend), Mouse IgG1 (isotype control), and XCL1 antibodies. All antibodies were used according to manufacturer's instructions.

CD4+ T cells were isolated from peripheral whole blood with CD4+ Rosette Kit (Stemcell Technologies). CD4+ T cells were incubated with anti-CD127-APC, anti-CD25-PE and anti-CD4-FITC antibodies. Cells were sorted by flow cytometry using a FACS Aria into CD4+CD25hiCD127lo/nTreg and CD4+CD25− responder T cells.

Suppression assays were performed in round-bottom 96 well microtiter plates. 3.75×103 CD4+CD25neg responder T cells, 3.75×103 autologous T reg, 3.75×104 allogeneic irradiated CD3-depleted PBMC were added as indicated. All wells were supplemented with anti-CD3 (clone HIT3a at 5.0 ug/ml). T cells were cultured for 7 days at 37° C. in RPMI 1640 medium supplemented with 10% fetal bovine serum. Sixteen hours before the end of the incubation, 1.0 mCi of $^3$H-thymidine was added to each well. Plates were harvested using a Tomtec cell harvester and $^3$H-thymidine incorporation determined using a Perkin Elmer scintillation counter. Antigen-presenting cells (APC) consisted of peripheral blood mononuclear cells (PBMC) depleted of T cells using StemSep human CD3+ T cell depletion (StemCell Technologies) followed by 40 Gy of irradiation.

Regulatory T cells were stimulated with anti-CD3 and anti-CD28 conditions and then stained with Live/Dead Red viability dye (Invitrogen), and surface markers CD4, CD25, and CD127. Cells were fixed in the Lyze/Fix PhosFlow™ buffer and permeabilized in denaturing Permbuffer III®. Cells were then stained with antibodies against each particular selected molecule.

Statistical analysis was performed using the GraphPad Prism software. Comparisons between two groups were made by using the two-tailed, unpaired Student's t-test. Comparisons between three groups were made by using 1-way ANOVA. P values less than 0.05 were considered significant (two-tailed). Correlation between two groups were determined to be statistically significant via the Spearman coefficient if the r value was greater than 0.7 or less than −0.7 (two-tailed).

In summary, the data showed a decreased proliferation in the presence of PM and Rev relative to PM in control fluid (no Rev, no Solis), indicates that the inventive electrokinetically generated fluid Rev improved regulatory T-cell function as shown by relatively decreased proliferation in the assay. Moreover, the evidence of this Example, indicate that beta blockade, GPCR blockade and Ca channel blockade affects the activity of Revera on Treg function.

Example 6

Patch Clamp Analysis Conducted on Calu-3 Cells Perfused with Inventive Electrokinetically Generated Fluids (RNS-60 and Solas) Revealed that (i) Exposure to RNS-60 and Solas Resulted in Increases in Whole Cell Conductance, (ii) that Exposure of Cells to the RNS-60 Produced an Increase in a Non-Linear Conductance, Evident at 15 Min Incubation Times, and (iii) that Exposure of Cells to the RNS-60 Produced an Effect of RNS-60 Saline on Calcium Permeable Channels Overview.

In this Example, patch clamp studies were performed to further confirm the utilities, as described herein, of the inventive electrokinetically generated saline fluids (RNS-60 and Solas), including the utility to modulate whole-cell currents. Two sets of experiments were conducted.

The summary of the data of the first set of experiments indicates that the whole cell conductance (current-to-voltage relationship) obtained with Solas saline is highly linear for both incubation times (15 min, 2 hours), and for all voltage protocols. It is however evident, that longer incubation (2 hours) with Solas increased the whole cell conductance. Exposure of cells to the RNS-60 produced an increase in a non-linear conductance, as shown in the delta currents (Rev-Sol subtraction), which is only evident at 15 min incubation time. The effect of the RNS-60 on this non-linear current disappears, and is instead highly linear at the two-hour incubation time. The contribution of the non-linear whole cell conductance, as previously observed, was voltage sensitive, although present at all voltage protocols.

The summary of data of the second set of experiments indicates that there is an effect of the RNS-60 saline on a non-linear current, which was made evident in high calcium in the external solution. The contribution of the non-linear whole cell conductance, although voltage sensitive, was present in both voltage protocols, and indicates an effect of RNS-60 saline on calcium permeable channels.

First Set of Experiments

Increase of Conductance; and Activation of a Non-Linear Voltage Regulated Conductance Materials and Methods:

The Bronchial Epithelial line Calu-3 was used in Patch clamp studies. Calu-3 Bronchial Epithelial cells (ATCC #HTB-55) were grown in a 1:1 mixture of Ham's F12 and DMEM medium that was supplemented with 10% FBS onto glass coverslips until the time of the experiments. In brief, a whole cell voltage clamp device was used to measure effects on Calu-3 cells exposed to the inventive electrokinetically generated fluids (e.g., RNS-60; electrokinetically treated normal saline comprising 60 ppm dissolved oxygen; sometimes referred to as "drug" in this Example).

Patch clamping techniques were utilized to assess the effects of the test material (RNS-60) on epithelial cell membrane polarity and ion channel activity. Specifically, whole cell voltage clamp was performed upon the Bronchial Epithelial line Calu-3 in a bathing solution consisting of: 135 mM NaCl, 5 mM KCl, 1.2 mM CaCl2, 0.8 mM MgCl2, and 10 mM HEPES (pH adjusted to 7.4 with N-methyl D-Glucamine). Basal currents were measured after which RNS-60 was perfused onto the cells.

More specifically, patch pipettes were pulled from borosilicate glass (Garner Glass Co, Claremont, Calif.) with a two-stage Narishige PB-7 vertical puller and then fire-polished to a resistance between 6-12 Mohms with a Narishige MF-9 microforge (Narishige International USA, East Meadow, N.Y.). The pipettes were filled with an intracellular solution containing (in mM): 135 KCl, 10 NaCl, 5 EGTA, 10 Hepes, pH was adjusted to 7.4 with NMDG (N-Methyl-D-Glucamine).

The cultured Calu-3 cells were placed in a chamber containing the following extracellular solution (in mM): 135 NaCl, 5 KCl, 1.2 CaCl2, 0.5 MgCl2 and 10 Hepes (free acid), pH was adjusted to 7.4 with NMDG.

Cells were viewed using the 40×DIC objective of an Olympus IX71 microscope (Olympus Inc., Tokyo, Japan). After a cell-attached gigaseal was established, a gentle suction was applied to break in, and to attain the whole-cell configuration. Immediately upon breaking in, the cell was voltage clamped at −120, −60, −40 and 0 mV, and was stimulated with voltage steps between ±100 mV (500 ms/step). After collecting the whole-cell currents at the control condition, the same cell was perfused through bath with the test fluid comprising same extracellular solutes and pH as for the above control fluid, and whole-cell currents at different holding potentials were recorded with the same protocols.

Electrophysiological data were acquired with an Axon Patch 200B amplifier, low-pass filtered at 10 kHz, and digitized with 1400A Digidata (Axon Instruments, Union City, Calif.). The pCLAMP 10.0 software (Axon Instruments) was used to acquire and to analyze the data. Current (I)-to-voltage (V) relationships (whole cell conductance) were obtained by plotting the actual current value at approximately 400 msec into the step, versus the holding potential (V). The slope of the IN relationship is the whole cell conductance.

Drugs and Chemicals.

Whenever indicated, cells were stimulated with a cAMP stimulatory cocktail containing 8-Br-cAMP (500 mM), IBMX (isobutyl-1-methylxanthine, 200 mM) and forskolin (10 mM). The cAMP analog 8-Br-cAMP (Sigma Chem. Co.) was used from a 25 mM stock in H2O solution. Forskolin (Sigma) and IBMX (Sigma) were used from a DMSO solution containing both 10 mM Forskolin and 200 mM IBMX stock solution. The data obtained are expressed as the mean±SEM whole cell current for 5-9 cells.

Figure 3A:
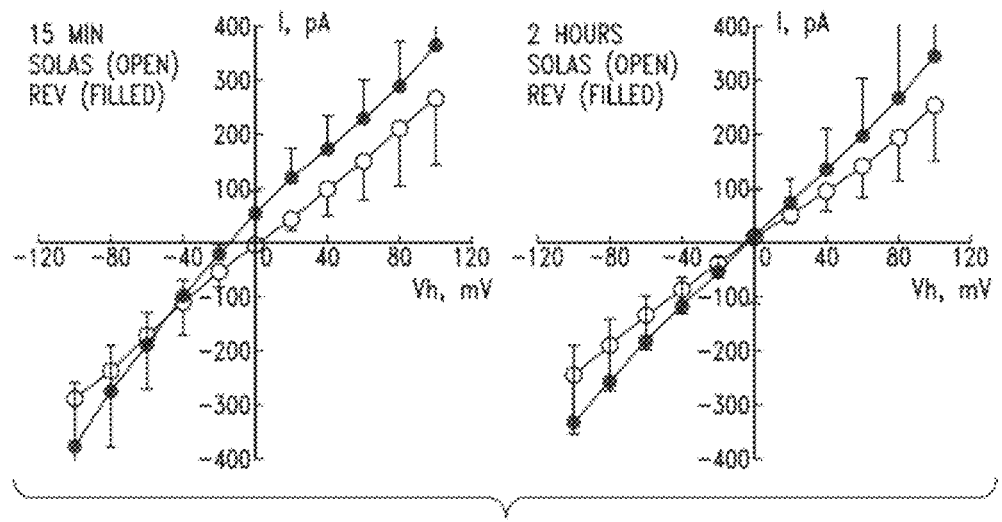
FIGS. 3 A-C demonstrate the results of a series of patch clamping experiments that assessed the effects of the electrokinetically generated fluid (e.g., RNS-60 and Solas) on epithelial cell membrane polarity and ion channel activity at two time-points (15 min (left panels) and 2 hours (right panels)) and at different voltage protocols.
Figure 3B:
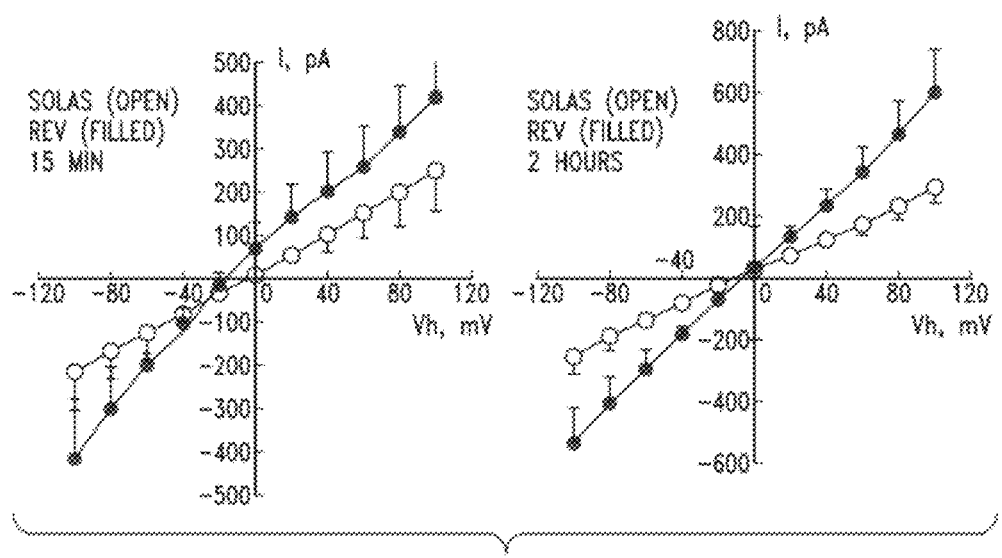
Figure 3C:
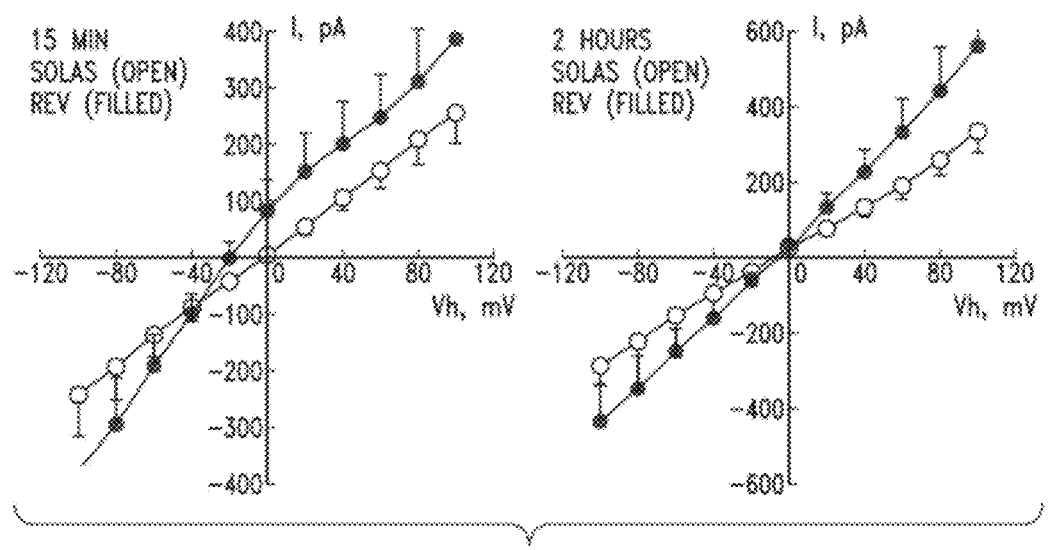

Results:

FIGS. 3 A-C show the results of a series of patch clamping experiments that assessed the effects of the electrokinetically generated fluid (e.g., RNS-60 and Solas) on epithelial cell membrane polarity and ion channel activity at two time-points (15 min (left panels) and 2 hours (right panels)) and at different voltage protocols (A, stepping from zero mV; B, stepping from −60 mV; and C, stepping from −120 mV). The results indicate that the RNS-60 (filled circles) has a larger effect on whole-cell conductance than Solas (open circles). In the experiment similar results were seen in the three voltage protocols and at both the 15 minute and two-hour incubation time points.

Figure 4A:
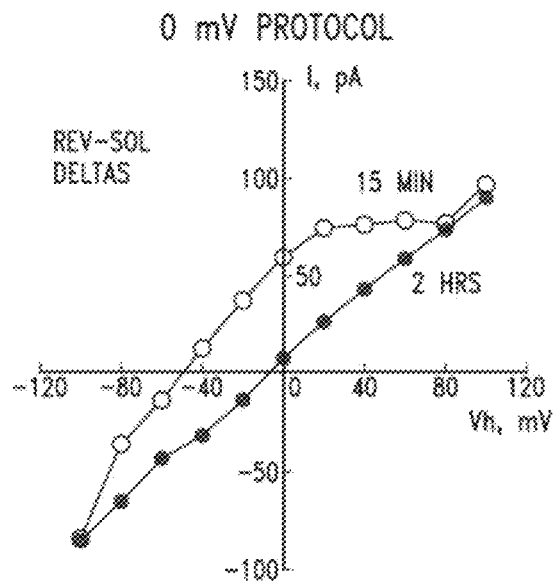
FIGS. 4 A-C show, in relation to the experiments relating to FIGS. 3 A-C, the graphs resulting from the subtraction of the Solas current data from the RNS-60 current data at three voltage protocols (A. stepping from zero mV; B. stepping from −60 mV; C. stepping from −120 mV) and the two time-points (15 mins (open circles) and 2 hours (closed circles)).
Figure 4B:
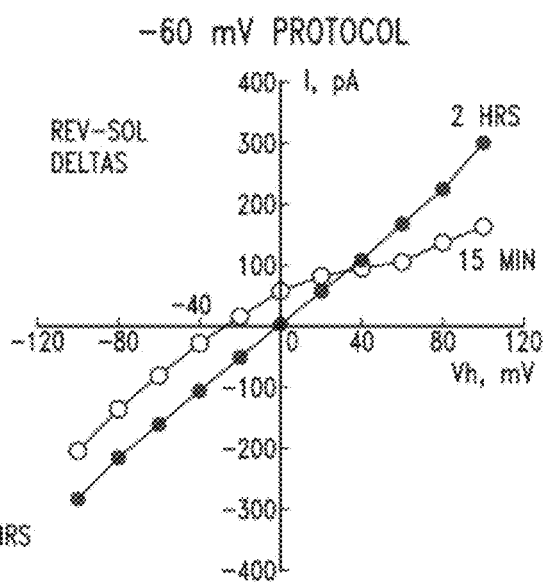
Figure 4C:
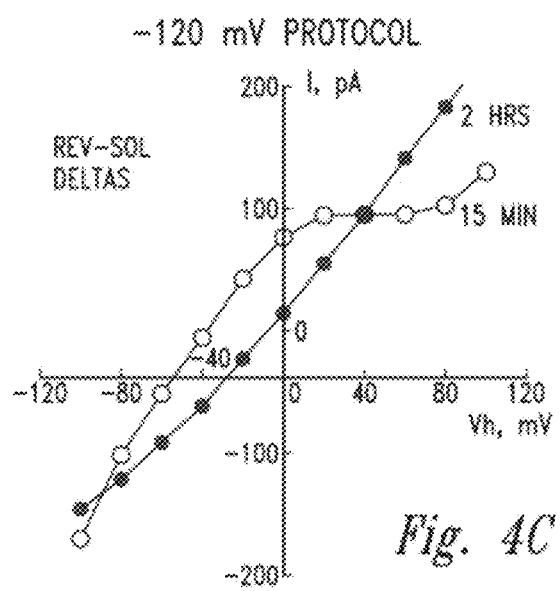
Figure 5A:
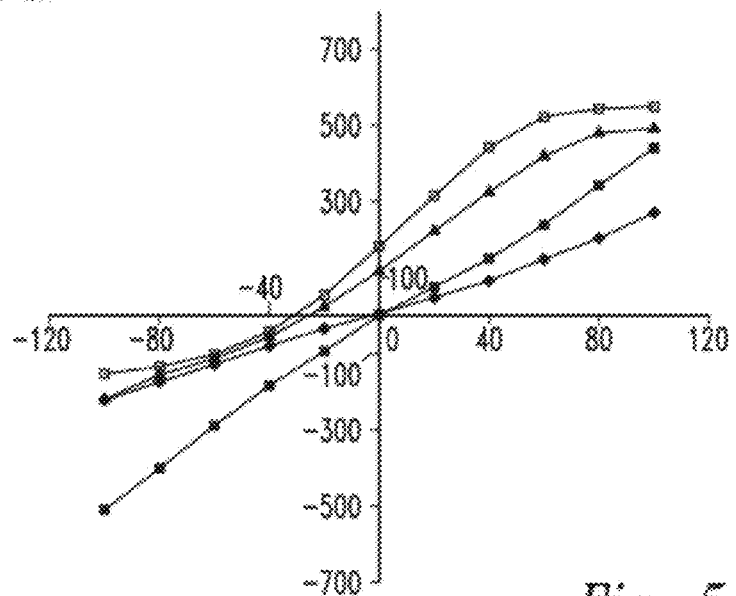
FIGS. 5 A-D demonstrate the results of a series of patch clamping experiments that assessed the effects of the electrokinetically generated fluid (e.g., Solas (panels A. and B.) and RNS-60 (panels C. and D.)) on epithelial cell membrane polarity and ion channel activity using different external salt solutions and at different voltage protocols (panels A. and C. show stepping from zero mV; panels B. and D. show stepping from −120 mV).
Figure 5B:
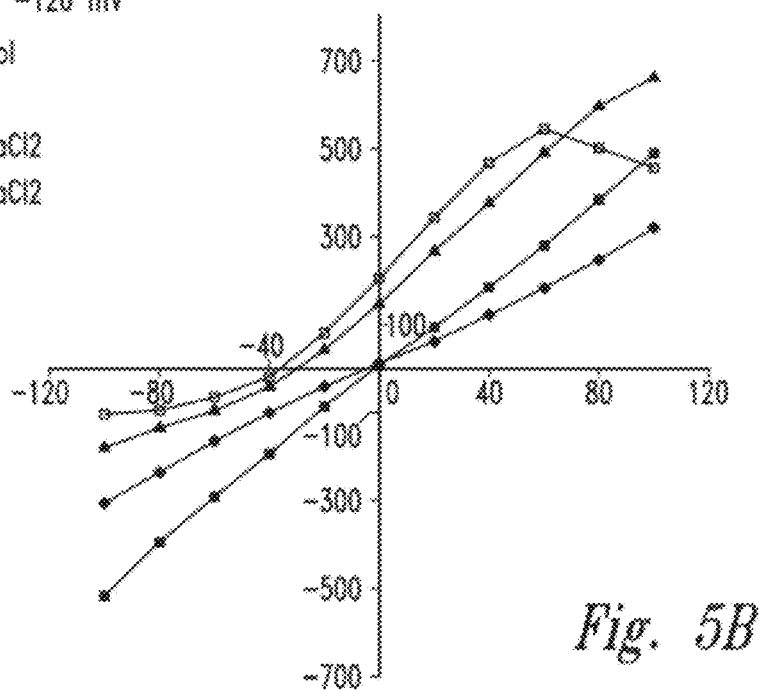
Figure 5C:
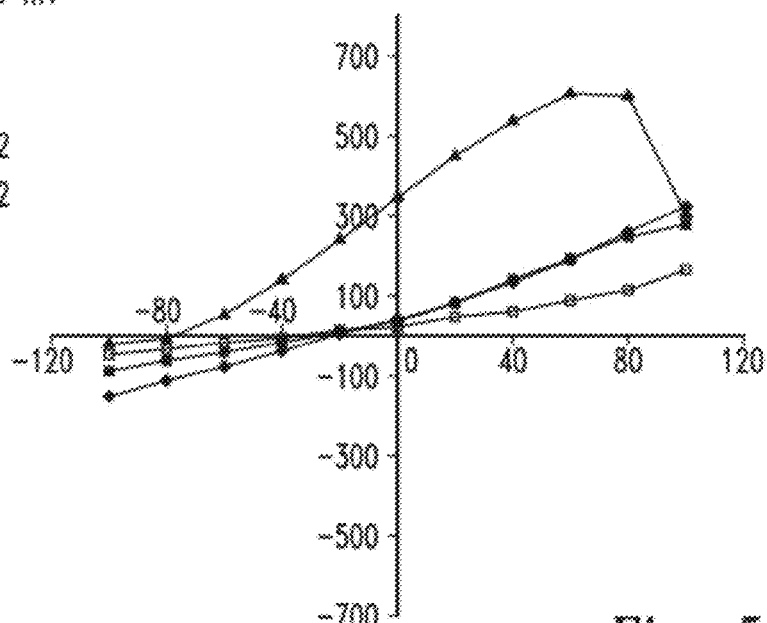
Figure 5D:
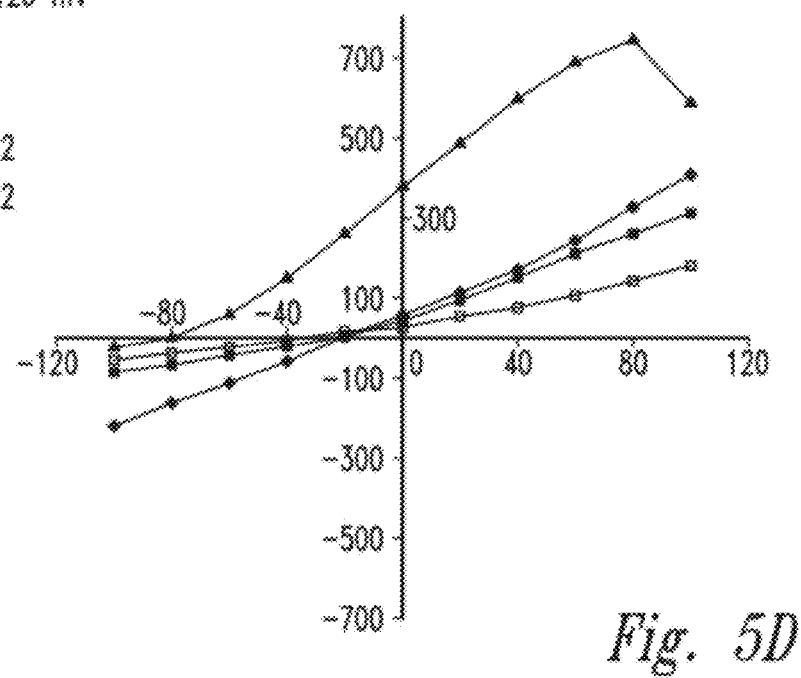
Figure 6A:
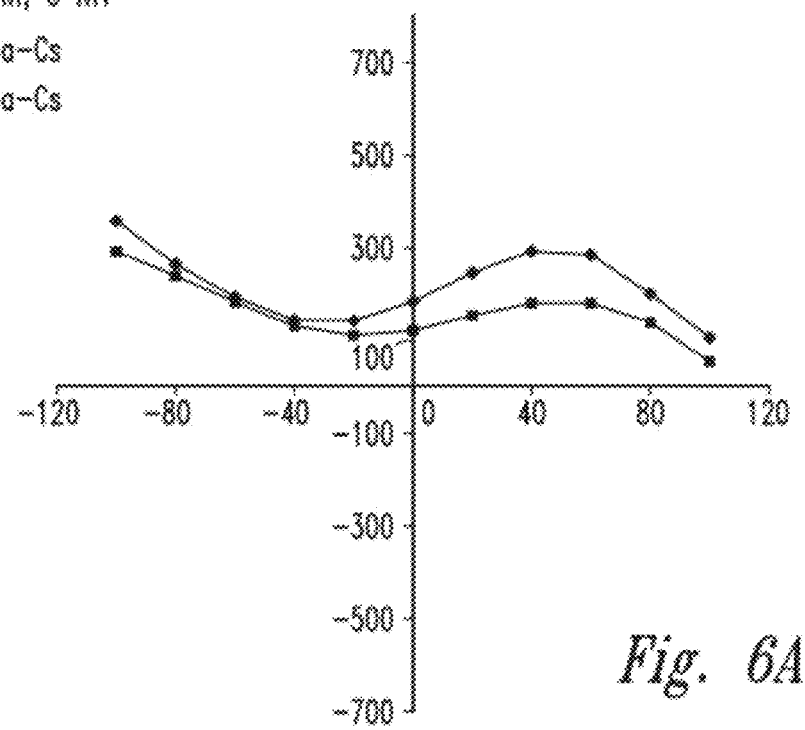
FIGS. 6 A-D show, in relation to the experiments relating to FIGS. 5 A-D, the graphs resulting from the subtraction of the CsCl current data (shown in FIG. 5) from the 20 mM $CaCl_2$ (diamonds) and 40 mM $CaCl_2$ (filled squares) current data at two voltage protocols (panels A. and C. stepping from zero mV; B. and D. stepping from −120 mV) for Solas (panels A. and B.) and Revera 60 (panels C. and D.).
Figure 6B:
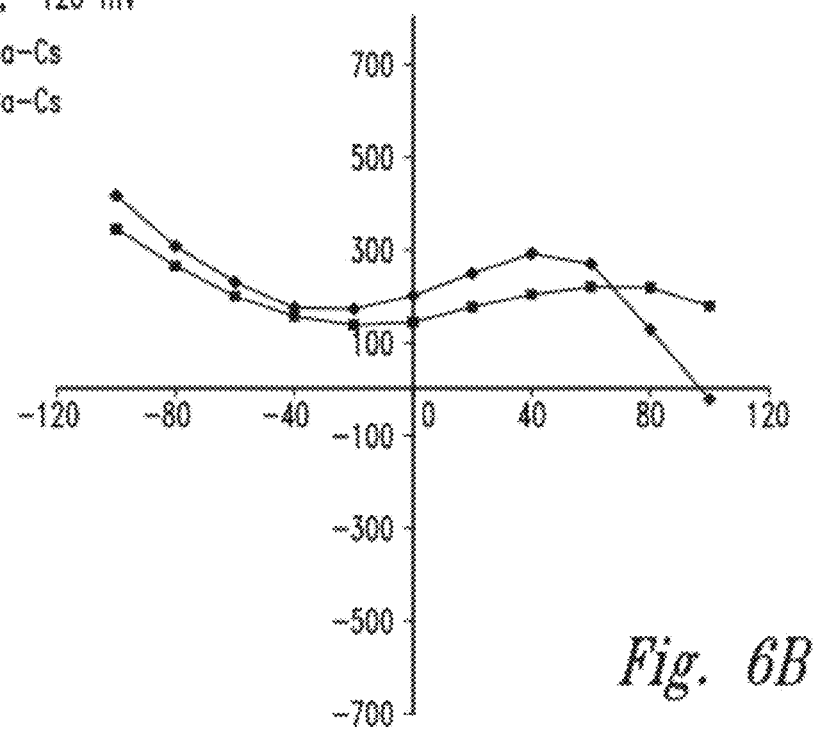
Figure 6C:
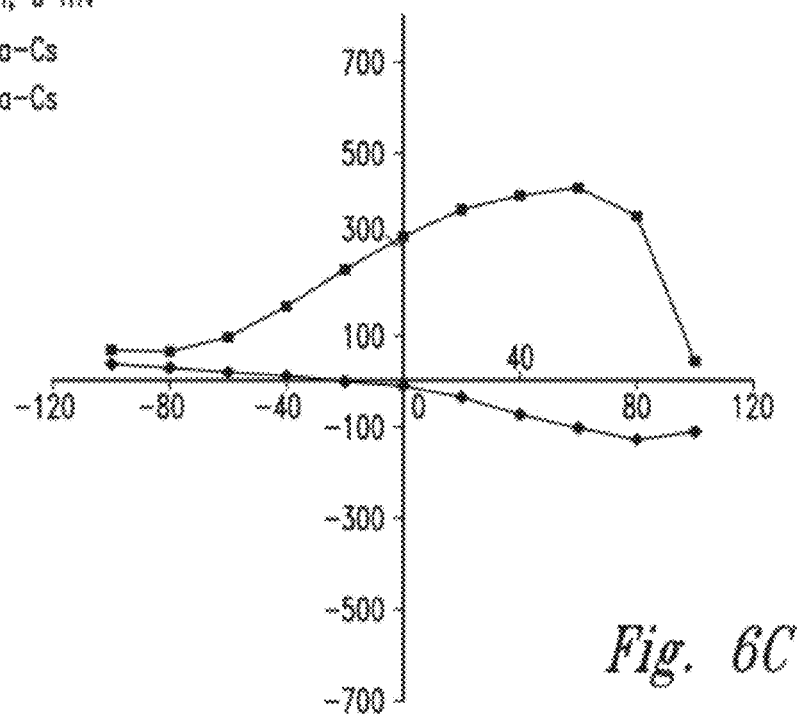
Figure 6D:
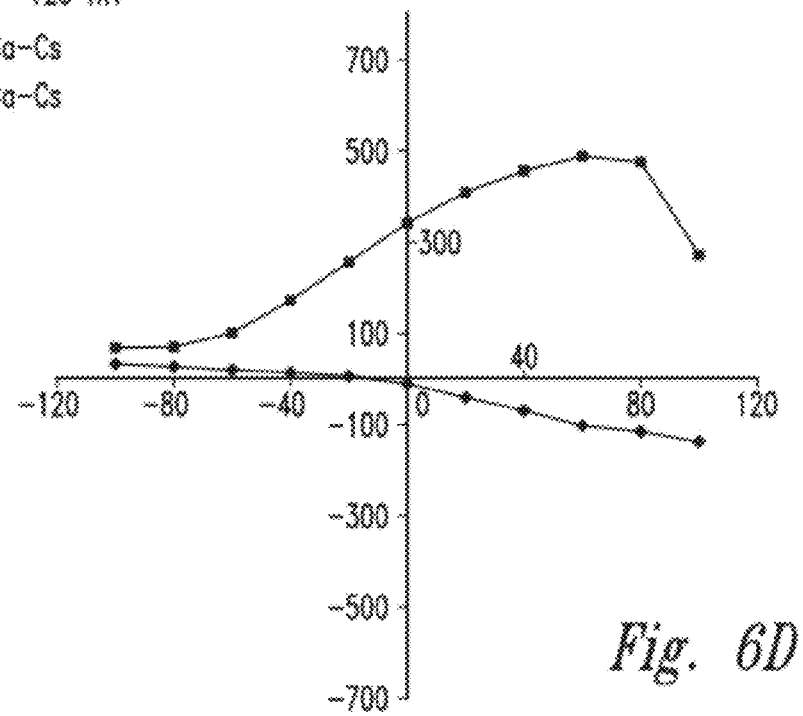

FIGS. 4 A-C show graphs resulting from the subtraction of the Solas current data from the RNS-60 current data at three voltage protocols ("Delta currents") (A, stepping from zero mV; B, stepping from −60 mV; and C, stepping from −120 mV) and the two time-points (15 mins (open circles) and 2 hours (filled circles)). These data indicated that at the 15 minute time-point with RNS-60, there is a non-linear voltage-dependent component that is absent at the 2 hour time point.

As in previous experiments, data with "Normal" saline gave a very consistent and time-independent conductance used as a reference. The present results were obtained by matching groups with either Solas or RNS-60 saline, and indicate that exposure of Calu-3 cells to the RNS-60 saline under basal conditions (without cAMP, or any other stimulation), produces time-dependent effect(s), consistent with the activation of a voltage-regulated conductance at shorter incubation times (15 min). This phenomenon was not as apparent at the two-hour incubation point. As described elsewhere herein, the linear component is more evident when the conductance is increased by stimulation with the cAMP "cocktail". Nonetheless, the two-hour incubation time showed higher linear conductance for both the RNS-60 and the Solas saline, and in this case, the RNS-60 saline doubled the whole cell conductance as compared to Solas alone. This evidence indicates that at least two contributions to the whole cell conductance are affected by the RNS-60 saline, namely the activation of a non-linear voltage regulated conductance, and a linear conductance, which is more evident at longer incubation times.

Second Set of Experiments

Effect on Calcium Permeable Channels

Methods for Second Set of Experiments:

See above for general patch clamp methods. In the following second set of experiments, yet additional patch clamp studies were performed to further confirm the utility of the inventive electrokinetically generated saline fluids (RNS-60 and Solas) to modulate whole-cell currents, using Calu-3 cells under basal conditions, with protocols stepping from either zero mV or −120 mV holding potentials.

The whole-cell conductance in each case was obtained from the current-to-voltage relationships obtained from cells incubated for 15 min with either saline. To determine whether there is a contribution of calcium permeable channels to the whole cell conductance, and whether this part of the whole cell conductance is affected by incubation with RNS-60 saline, cells were patched in normal saline after the incubation period (entails a high NaCl external solution, while the internal solution contains high KCl). The external saline was then replaced with a solution where NaCl was replaced by CsCl to determine whether there is a change in conductance by replacing the main external cation. Under these conditions, the same cell was then exposed to increasing concentrations of calcium, such that a calcium entry step is made more evident.

Results:

FIGS. 5 A-D show the results of a series of patch clamping experiments that assessed the effects of the electrokinetically generated fluid (e.g., Solas (panels A and B) and RNS-60 (panels C and D)) on epithelial cell membrane polarity and ion channel activity using different external salt solutions and at different voltage protocols (panels A and C show stepping from zero mV, whereas panels B and D show stepping from −120 mV). In these experiments one time-point of 15 minutes was used. For Solas (panels A and B) the results indicate that: 1) using CsCl (square symbols) instead of NaCl as the external solution, increased whole cell conductance with a linear behavior when compared to the control (diamond symbols); and 2) $CaCl_2$ at both 20 mM $CaCl_2$ (circle symbols) and 40 mM $CaCl_2$ (triangle symbols) increased whole cell conductance in a non-linear manner. For RNS-60 (panels C and D), the results indicate that: 1) using CsCl (square symbols) instead of NaCl as the external solution had little effect on whole cell conductance when compared to the control (diamond symbols); and 2) $CaCl_2$ at 40 mM (triangle symbols) increased whole cell conductance in a non-linear manner.

FIGS. 6 A-D show the graphs resulting from the subtraction of the CsCl current data (shown in FIG. 5) from the 20 mM $CaCl_2$ (diamond symbols) and 40 mM $CaCl_2$ (square symbols) current data at two voltage protocols (panels A and C, stepping from zero my; and B and D, stepping from −120 mV) for Solas (panels A and B) and RNS-60 (panels C and D). The results indicate that both Solas and RNS-60 solutions activated a calcium-induced non-linear whole cell conductance. The effect was greater with RNS-60 (indicating a dosage responsiveness), and with RNS-60 was only increased at higher calcium concentrations. Moreover, the non-linear calcium dependent conductance at higher calcium concentration was also increased by the voltage protocol.

The data of this second set of experiments further indicates an effect of RNS-60 saline and Solas saline for whole cell conductance data obtained in Calu-3 cells. The data indicate that 15-min incubation with either saline produces a distinct effect on the whole cell conductance, which is most evident with RNS-60, and when external calcium is increased, and further indicates that the RNS-60 saline increases a calcium-dependent non-linear component of the whole cell conductance.

The accumulated evidence suggests activation by Revalesio saline of ion channels, which make different contributions to the basal cell conductance.

Taken together with Applicants' other data (e.g., the data of Applicants other working Examples) particular aspects of the present invention provide compositions and methods for modulating intracellular signal transduction, including modulation of at least one of membrane structure, membrane potential or membrane conductivity, membrane proteins or receptors, ion channels, lipid components, or intracellular components with are exchangeable by the cell (e.g., signaling pathways, such as calcium dependant cellular signaling systems, comprising use of the inventive electrokinetically generated solutions to impart electrochemical and/or conformational changes in membranous structures (e.g., membrane and/or membrane proteins, receptors or other membrane components) including but not limited to GPCRs and/or g-proteins. According to additional aspects, these effects modulate gene expression, and may persist, dependant, for example, on the half lives of the individual messaging components, etc.

Example 7

The Inventive Electrokinetic Fluid was Shown to be Substantially Efficacious in a Dose-Responsive Manner in an Art-Recognized Acute Experimental Allergic (Autoimmune) Encephalomyelitis (EAE) Rat MBP Model of Multiple Sclerosis (MS)

Overview:

In this working EXAMPLE, the inventive electrokinetic fluid RNS-60 was evaluated at two doses, in both prophylactic and therapeutic administration regimens, in an art-recognized Myelin Basic Protein MBP induced acute Experimental Allergic Encephalomyelitis (EAE) rat model. The inventive electrokinetic fluid RNS-60 was shown to be substantially efficacious in a dose-responsive manner. Both the therapeutic (daily administration of RNS-60 beginning concomitant with MBP injection) and prophylactic (daily administration of RNS-60 beginning seven days prior to MBP injection) RNS-60 dosage regimens showed a marked decrease, as well as a delayed onset (in the high dose groups) of clinical score. According to particular aspects of the present invention, therefore, the inventive electrokinetic compositions have substantial utility for treating, including alleviating and preventing, the symptoms of EAE in an art-recognized rat model of human MS. According to further aspects of the present invention, therefore, the inventive electrokinetic compositions have substantial utility for treating, including alleviating and preventing, the symptoms of MS in afflicted mammals (preferably humans). In yet further aspects, the inventive electrokinetic compositions cross the Blood Brain Barrier (BBB), and thus provided a novel method for treating inflammatory conditions of the central nervous system.

Multiple Sclerosis (MS).

Multiple Sclerosis (MS) is a demyelinating disease of the central nervous system (CNS), and is one of the most common disabling neurological diseases in young adults. The main characteristics of this disease are focal areas of demyelination and inflammation. The disease course is unpredictable and life-long, and affects women more commonly than men. The etiology of the disease appears to be dependent on genetic and environmental factors. In the periphery, antigen is bound by antigen presenting cells (APC) via MCH II. Th0 cells bind to the antigen and undergo activation and differentiation. Adhesion molecules and matrix metalloproteases (MMPs) help the Th1 cells to bind and penetrate the Blood Brain Barrier (BBB). Upon crossing the BBB into the CNS, Th1 cells engage antigen-MHC complexes and produce pro-inflammatory cytokines leading to damage in the CNS. The autoimmune system recognizes myelin proteins as foreign and begins to attack. Historically, while Th1 cells are thought to play a predominant role in the pathology of the disease, recent evidence indicates that a proinflammatory cascade of Th17 cells, IL-6 and TGF-β plays a critical role in the pathogenesis of EAE and MS.

Experimental Autoimmune Encephalomyelitis (EAE).

Experimental Autoimmune Encephalomyelitis (EAE), also called Experimental Allergic Encephalomyelitis, is a non-human animal model of Multiple Sclerosis (MS). While not MS, the different forms and stages of EAE resemble the various forms and stages of MS very closely in a large number of ways. More specifically, EAE is an acute or chronic-relapsing, acquired, inflammatory and demyelinating autoimmune disease. The animals are injected with the whole or parts of various proteins (e.g., Myelin Basic Protein (MBP), Proteolipid Protein (PLP), and Myelin Oligodendrocyte Glycoprotein (MOG)) that make up myelin, the insulating sheath that surrounds nerve cells (neurons), to induce an autoimmune response against the animal's own myelin that closely resembles MS in humans. EAE has been induced in a number of different animal species including mice, rats, guinea pigs, rabbits, macaques, rhesus monkeys and marmosets. For various reasons including the number of immunological tools, the availability, lifespan and fecundity of the animals and the resemblance of the induced disease to MS, mice and rats are the most commonly used species. The acute rat EAE model has a strong inflammatory component and is therefore an appropriate model in which to investigate the therapeutic potential of an agent that targets immune events in MS.

MBP-Induced EAE.

MPB in Lewis rats following one dose will lead to relapse that is characterized mainly by hind paw paralysis. Lewis rats are subjected to MBP injection on day 0. Disease develops between day 12-16, with full disease recovery occurring between days 18-21. The model is self limiting and does not show demyelination.

Materials and Methods:

Production and Characterization of the test fluid (RNS-60). Filter sterilized RNS-60 was prepared by Applicants according to methods described in US2008/0219088 (published on 11 Sep. 2008), US2008/0281001 (published on 11 Nov. 2008) and WO2008/052143 (published on 2 May 2008), all of which are incorporated herein by reference in their entirety and particularly for all aspects relating to the apparatus and/or methods for preparing Applicants' inventive electrokinetic fluids. The dissolved oxygen (DO) content of the RNS-60 used was 59 ppm, as determined by the Winkler Titration assay (Y. C. Wong & C. T. Wong. New Way Chemistry for Hong Kong A-Level Volume 4, Page 248. Or Standard Methods for the Examination of Water and Wastewater—20th Edition ISBN 0-87553-235-7). RNS-60 fluid was labeled with a test item (TI) number, receipt date, storage conditions and expiry date. The storage conditions and handling of the RNS-60 was per Applicants' specification to ensure stability at the Testing Facility during testing. Fluid was kept refrigerated at 2-8° C. when not in use. Vials containing fluid were used as single use containers.

Vehicle Control Fluid.

Vehicle control fluid was Normal Saline for injection (0.9%) from Hospira.

Dexamethasone.

Dexamethasone was purchased from Sigma (Cat. No. D1756; Lot No. 096K1805). For administration, Dexamethasone (white powder) was diluted in ethanol to achieve a concentration of 1 mg/ml and then diluted again in distilled water to achieve a dose concentration of 0.1 mg/ml.

EAE Induction Items:

MBP Antigenic Agent.

MBP was Myelin Basic Protein from guinea pig (Des-Gly-77, Des-His-78)-MBP (68-84); Cat. No. H-6875; provided by MD Bioscience). MBP was dissolved in physiological saline at a concentration of 2 mg/ml;

CFA Sensitizing Agent.

Complete Freund's Adjuvant (CFA) was from MD Biosciences Division of Morwell Diagnostics GmbH (Cat. No. IMAD-4). CFA suspension, containing heat killed *Mycobacterium Tuberculosis* H37 Ra at a concentration of 4 mg/ml, was used as supplied; and MBP/CFA Emulsion (Antigenic/Sensitizing Agents).

Prior to the single inoculations carried out on study day 0, one volume of MBP solution was mixed with an equal volume of CFA 4 mg/ml by employing two syringes connected by a Luer fitting to thoroughly mix the emulsive mixture to equal a total dose volume of 100 μl/animal. The dose was delivered as 2×50 μl subcutaneous (SC) bilateral injections into the intraplantar paw regions.

Test Animals; Rats.

Sixty (60) female Lewis rats (6-7 weeks of age at study initiation) were obtained from Harlan Laboratories Israel, Ltd. Weight variation of animals at the time of treatment initiation should not exceed 20% of the mean weight. The health status of the animals used in this study is examined upon their arrival. Only animals in good health were acclimatized to laboratory conditions and used in the study. Prior to entry in the study, the animals were acclimated for at least 5 days. During acclimation and throughout the study duration, animals were housed within a limited access rodent facility and kept in groups of maximum 5 rats in polypropylene cages fitted with solid bottoms and filled with sterile wood shavings as bedding material. Animals were provided ad libitum with a commercial rodent diet and had free access to drinking water, which was supplied to each cage via polyethylene bottles with stainless steel sipper tubes. A feed lot analysis of the diet batch used in the study was included in the archives with the study data. Water was monitored periodically. Automatically controlled environmental conditions were set to maintain temperature at 20-24° C. with a relative humidity (RH) of 30-70%, a 12:12 hour light:dark cycle and 15-30 air changes/hr in the study room. Temperature and RH were monitored daily. The light cycle was monitored by the control clock. Animals were given a unique animal identification using tail marks. This number also appeared on a cage card, visible on the front of each cage. The cage card also contained the study and group numbers, route of administration, gender, strain and all other relevant details as to treatment group.

TABLE 6

Constitution of Test Groups and Dose Levels, listing the 6 experimental groups comprising the study:

| Group Number | Group Size | Test Material | Route | Dose Level (mg/kg/ admin) | Volume Dosage (ml/kg) | Regime |
|---|---|---|---|---|---|---|
| 1F | n = 10 | Vehicle Control | IV | 0 | 2 ml for 350 g rat | 7 days prior to disease induction until the end of the study |
| 2F | n = 10 | Dexamethasone | IP | 1 | 10 | Once daily beginning on study day 0 |
| 3F | n = 10 | RNS-60 | IV | | 1 ml for 350 g rat | 7 days prior to disease induction until the end of the study |
| 4F | n = 10 | RNS-60 | IV | | 2 ml for 350 g rat | 7 days prior to disease induction until the end of the study |
| 5F | n = 10 | RNS-60 | IV | | 1 ml for 350 g rat | Once daily beginning on study day 0 |
| 6F | n = 10 | RNS-60 | IV | | 2 ml for 350 g rat | Once daily beginning on study day 0 |

Test procedures and Principles of the Acute EAE Murine Model.

Experimental Allergic Encephalomyelitis (EAE) is a central nervous system (CNS) autoimmune demyelinating disease that mimics many of the clinical and pathologic features of Multiple Sclerosis (MS). The acute rat model consists of a sensitization period, induced by the single subcutaneous (SC) injection of Myelin basic protein (MBP) emulsified in Complete Freund's Adjuvant (CFA) on day 0 of the study.

Figure 8:
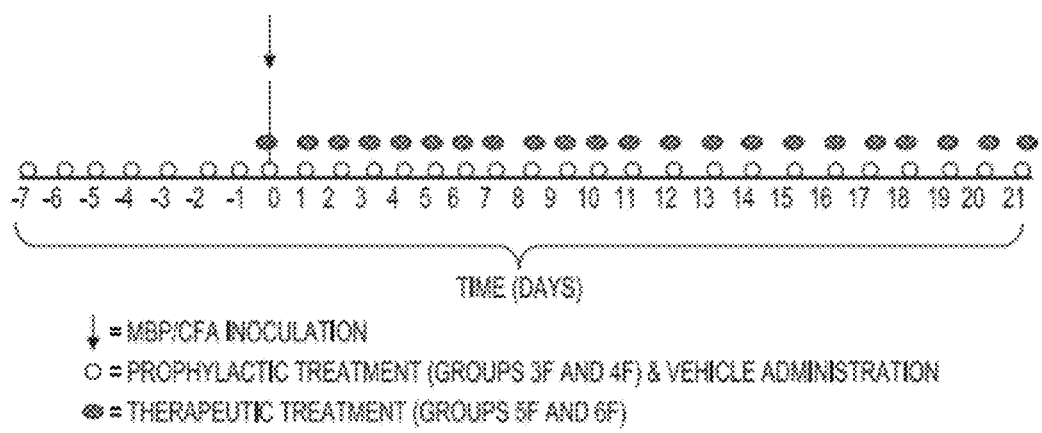
FIG. 8 shows a schematic depiction of the EAE induction and treatment regimens used in the experiment shown in FIG. 7.

A schematic depiction of EAE induction and treatment regimens is shown in FIG. 8).

EAE Induction:

MBP/CF A. As shown in the schematic description in FIG. 8), all animals were subjected on study day 0 (study commencement) to a single inoculum injection consisting of a homogenate emulsive mixture of MBP and CFA (MBP/CFA encephalitogenic emulsive inoculum (100 μg MBP/200 μg CFA) was injected at a total dose volume of 100 μl/animal and delivered as 2×50 μl subcutaneous (SC) bilateral injections into the intraplantar paw regions).

Treatment:

Treatment Regimen and Procedure.

All compounds were prepared fresh each day by a person different than the one scoring the animals. The person that scored the animals received vials marked only with group numbers and was unaware of the treatment.

Route of Administration:

(i) RNS-60 (IV); (ii) Vehicle Controls: (IV); and (iii) Positive Controls: (IP).

Dose Levels and Volume Dosages:

(i) RNS-60: Low dose 2 ml for 350 g; High dose 4 ml for 350 g; (ii) Vehicle Controls: 0; and (iii) Positive Control (Dexamethasone): 1 mg/kg.

Supportive Care.

Unless determined during the course of the study, once EAE experimental effects were expected and/or observed (approximately 8-12 days post the single encephalitogenic inoculation), or when the animals were showing a decrease is body weight greater than 15% from their previous determination or a decrease greater than 20% of their initial body weight measurement, appropriate supportive care was carried out on a case-by-case basis.

Feeding and Watering.

An additional water source consisting of chipped pellets or mealy rodent diet, soaked in drinking water is placed on the cage bottom and in front of the crawling/non-mobile animals.

Dehydration.

Animals may be subjected to subcutaneous (SC) supplemental fluid therapy with Dextrose 5% solution at least twice daily and up to 2 ml/animal/day until body weight returns to be within 10% of the initial determination.

Urination.

Palpation of the animals' abdomen is carried out in order to assist with voiding and to observe whether the animals can empty their bladder.

Other Special Care.

Animals' perianal areas and hind legs were cleaned as needed with a moistened gauze pad.

Observations and Examinations:

Clinical Signs.

Throughout the entire 21-day study, careful clinical examinations were carried out and recorded at least once daily in addition to the EAE clinical scoring and assessment (see below). Observations included changes in skin, fur, eyes, mucous membranes, occurrence of secretions and excretions (e.g. diarrhea) and autonomic activity (e.g., lacrimation, salivation, piloerection, pupil size, unusual respiratory pattern), gait, posture and response to handling, as well as the presence of unusual behavior, tremors, convulsions, sleep and coma.

Body Weights.

Body weight loss can be the first sign of disease initiation, while a sudden marked weight gain tends to accompany remission of EAE symptoms. Therefore, determination of individual body weights of animals was made shortly before EAE induction on study day 0 (study commencement) and thereafter on a daily basis throughout the entire 21-day observation period.

EAE Clinical Scoring and Assessments.

Initially, all animals were examined for signs of any neurological responses and symptoms prior to EAE induction (study day 0) and thereafter examined on a daily basis throughout the entire 21-day observation period. To avoid experimental bias, EAE reactions are determined in a blinded fashion, as much as possible, by a staff member unaware of the specific treatment applied. EAE reactions were scored and recorded according to a classical, art-recognized conventional 0-5 scale in ascending order of severity as shown below in Table 7:

TABLE 7

EAE reactions were scored and recorded according to a classical, art-recognized conventional 0-5 scale in ascending order of severity.

| Grade | Signs/Symptoms |
| --- | --- |
| 0 | No abnormalities |
| 0.5 | Tail weakness distal half |
| 1 | Tail weakness proximal half |
| 1.5 | Hind paw weakness one paw |
| 2 | Hind paw weakness two paws |
| 2.5 | Fore paw paralysis one paw |
| 3 | Fore paw paralysis two paws |
| 4 | Full paralysis |
| 5 | Death |

Blood Samples.

On the day of study termination (day 21), all animals were bled 1 hour post injection. Samples were collected on study days 0 (prophylactic groups only), 7, 14, and 21. Plasma was collected in heparinized vials and kept at −20° C. A volume of 300 μl was stored for the blood count analysis and 100 μl was stored and used for further cytokine analysis via Luminex Technology. Blood counts were analyzed for days 0, 7, 14, and 21.

Tissue Collection.

At study termination, the animals were perfused with 4% PFA. Brains and spinal cords were collected and kept in 4% PFA.

Humane Endpoints.

Animals found in a moribund condition and/or animals showing severe pain and enduring signs of severe distress were humanely euthanized.

Statistics/Data Evaluation:

Evaluation was primarily based on the relative recorded changes in both neurological symptoms and body weights, expressed as absolute values, percentage (%) change and mean group values obtained in all treated groups vs. those of the Vehicle Control. Analysis of the data by appropriate statistical methods was applied to determine significance of treatment effects.

Animal Care and Use Statement:

This study was performed following approval of an application form submitted to the appropriate Committee for Ethical Conduct in the Care and Use of Laboratory Animals that the study complied with the rules and regulations set forth.

Figure 7:
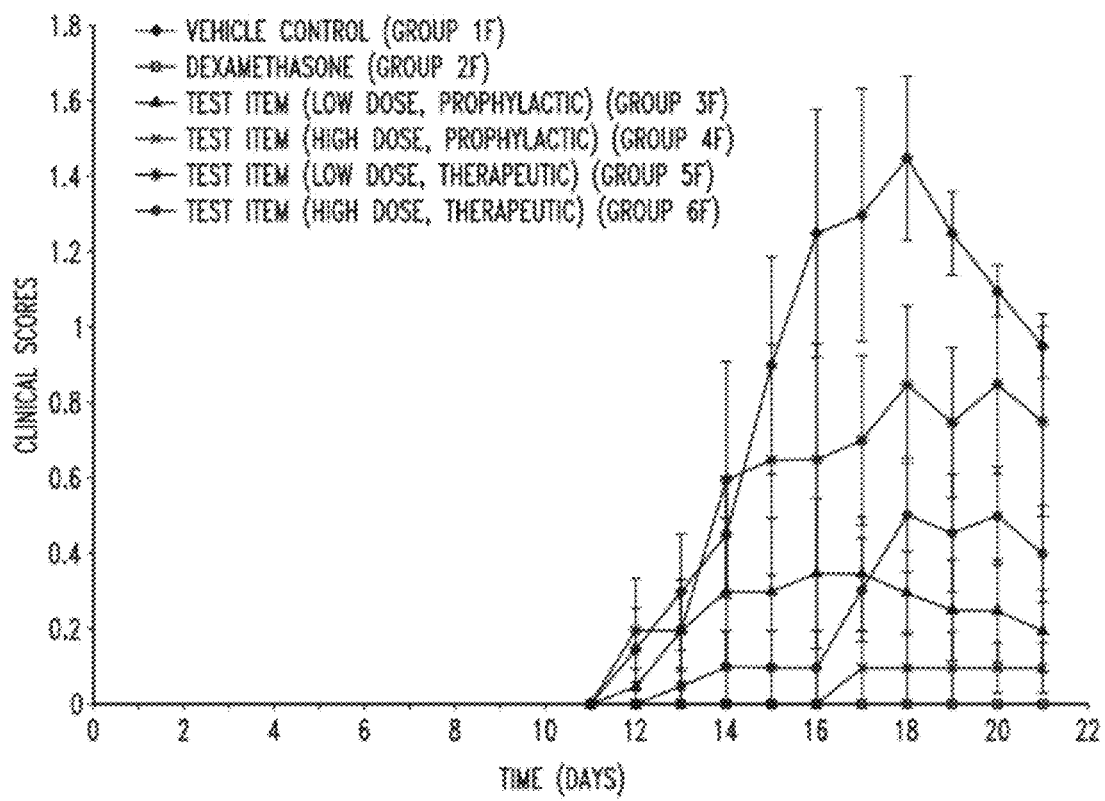
FIG. 7 shows that the inventive electrokinetic fluid (RNS-60) was substantially efficacious in an art-recognized Experimental Autoimmune Encephalomyelitis (EAE) rat model of Multiple Sclerosis (MS).

Results:

Results of the study are shown in FIG. 7, where time (days after MBP injection) is shown on the X-axis, and "Clinical scores" (see above under "Materials and Methods") are shown on the Y-axis.

FIG. 7 shows that the inventive electrokinetic fluid (RHS-60) was substantially efficacious in an art-recognized Experimental Autoimmune Encephalomyelitis (EAE) rat model of Multiple Sclerosis (MS) (see above under "Materials and Methods").

Specifically, compared to the vehicle control group (filled diamonds) over a 17 day period, both the therapeutic (daily administration of RNS-60 beginning concomitant with MBP injection) and prophylactic (daily administration of RNS-60 beginning seven days prior to MBP injection) RNS-60 dosage regimens showed a marked decrease, as well as a delayed onset (in the high dose groups) of clinical score.

The clinical score of the low dose (daily one cc injection) RNS-60 therapeutic group was approximately one-half (½) that of the vehicle control group, while the clinical score of the high dose (daily two cc injection) RNS-60 therapeutic group was not only approximately one-fifth (⅕) to one-tenth (1/10) that of the vehicle control group, but also displayed delayed onset.

The clinical score of the low dose (daily one cc injection) RNS-60 prophylactic group was approximately one-third (⅓) that of the vehicle control group, while the clinical score of the high dose (daily two cc injection) RNS-60 prophylactic group was not only zero (no detectable clinical score) through day 16, thereby displaying substantially delayed onset, but when observable at day 17 was less than one-tenth (1/10) that of the vehicle control group at the same time point.

According to particular aspects of the present invention, therefore, the inventive electrokinetic compositions have substantial utility for treating, including alleviating and preventing, the symptoms of EAE in art-recognized rat models of human. MS.

Example 8

The Inventive Electrokinetic Fluid was Shown to be Effective in Sustaining the Weight of Rats in an Art-Recognized Acute Experimental Allergic (Autoimmune) Encephalomyelitis (EAE) Rat MBP Model of Multiple Sclerosis (MS)

Overview:

This working EXAMPLE discloses the weight change of rats subjected to the experiment described in Example 7. Body weight loss can be the first sign of disease initiation, while a sudden marked weight gain tends to accompany remission of EAE symptoms. Therefore, determination of individual body weights of animals was made shortly before EAE induction on study day 0 (study commencement) and on a daily basis throughout the 21-day observation period. The effect of the inventive electrokinetic fluid RNS-60 on body weight was shown to be effective in sustaining the weight of rats subjected to the EAE rat model (FIG. 9).

Figure 9A:
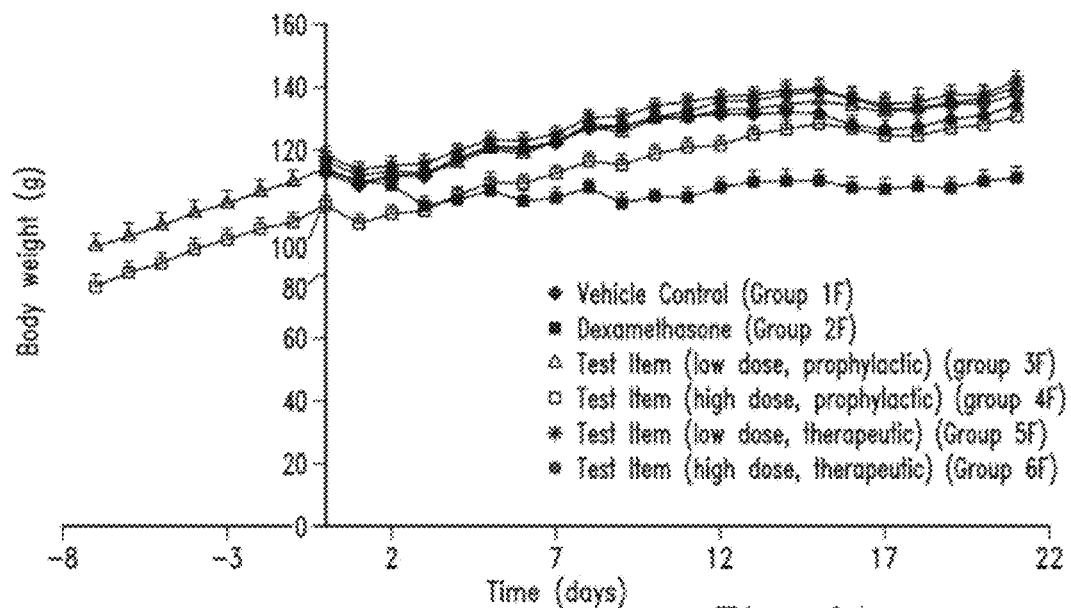
FIG. 9A is a graphical representation of the body weight (in grams) of the animals subjected to the EAE treatment regimen used in the experiment shown in FIGS. 7 and 8.
Figure 9B:
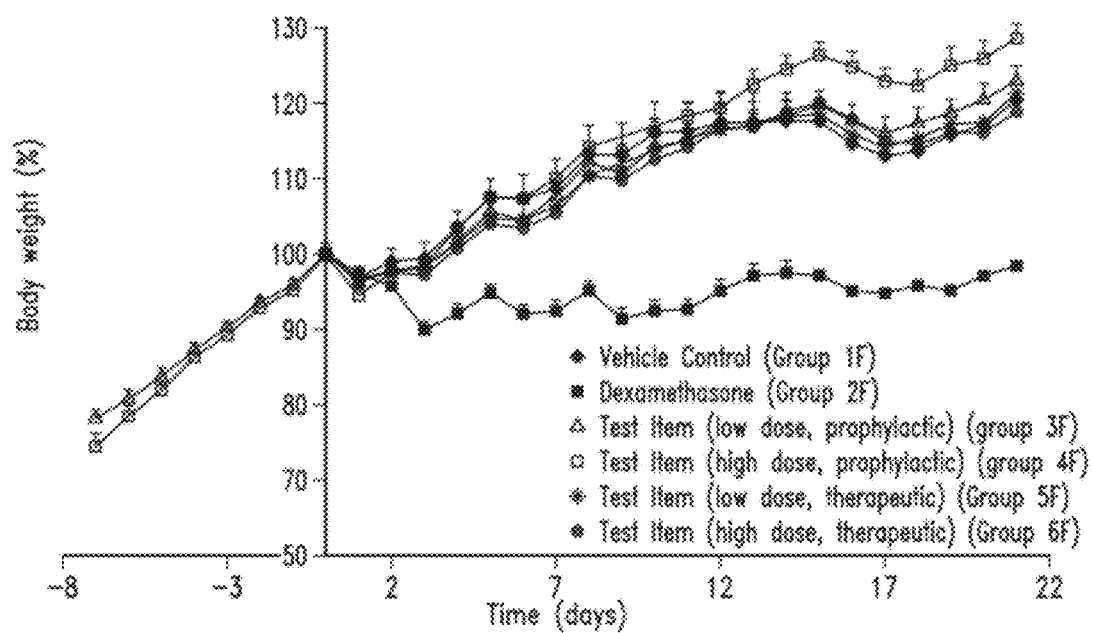
FIG. 9B shows the calculated change in body weight (in percentage) of the animals subjected to the EAE treatment regimen.
Figure 10A:
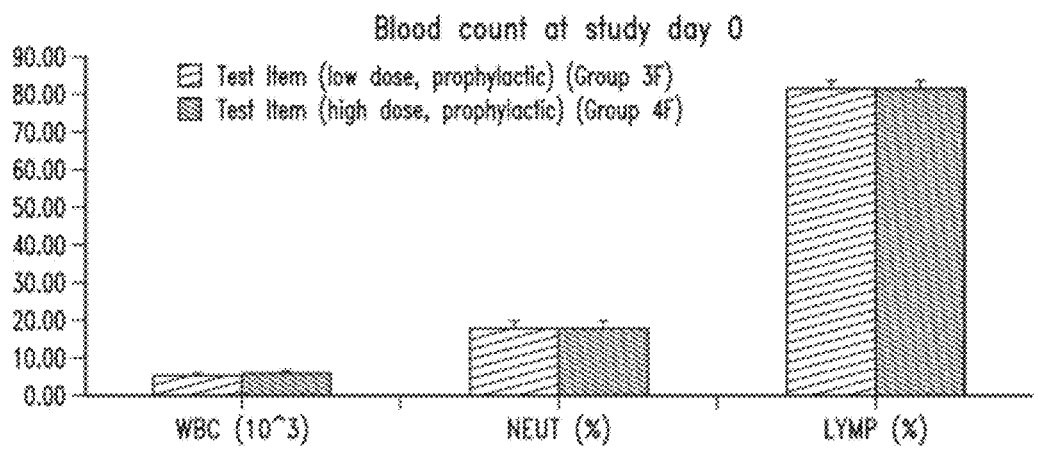
FIGS. 10 A-D show that the inventive electrokinetic fluid (RNS-60) had little affect on the level of total white blood cells (WBC), neutrophils, and lymphocytes when compared to the vehicle control during the EAE treatment regimen as used in the experiment shown in FIGS. 7 and 8. Panels A, B, C, and D show the results at study day 0, 7, 14, and 21, respectively.
Figure 10B:
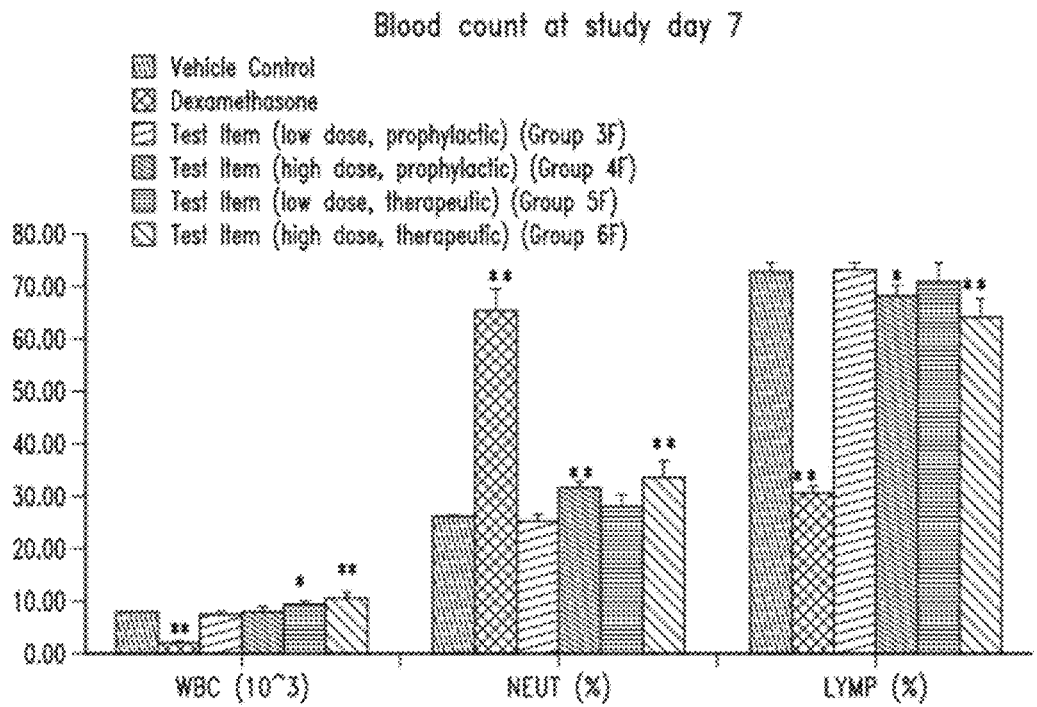
Figure 10C:
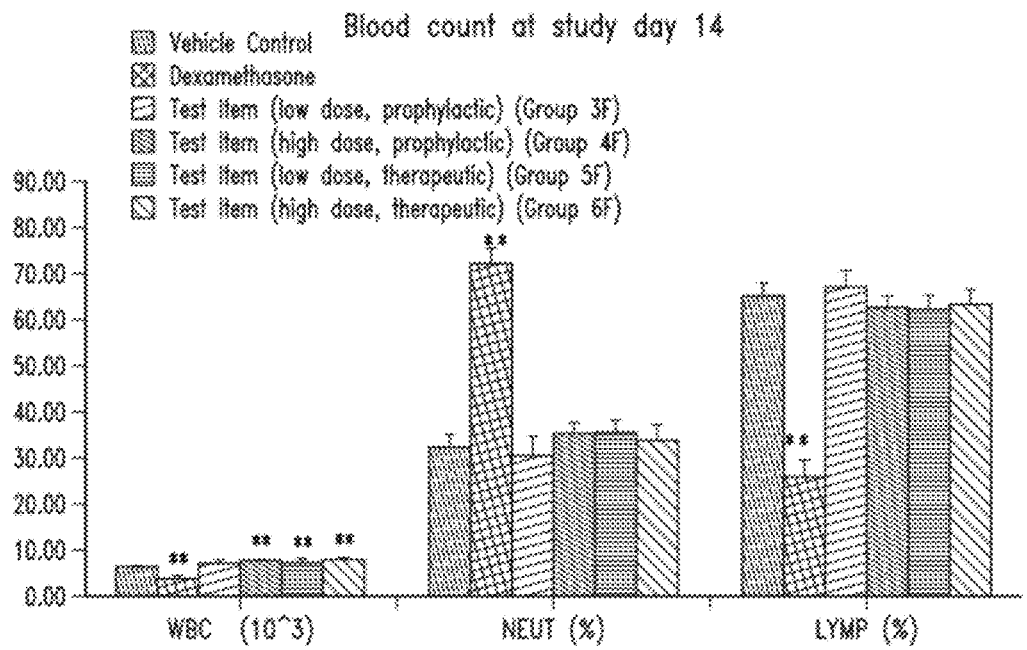
Figure 10D:
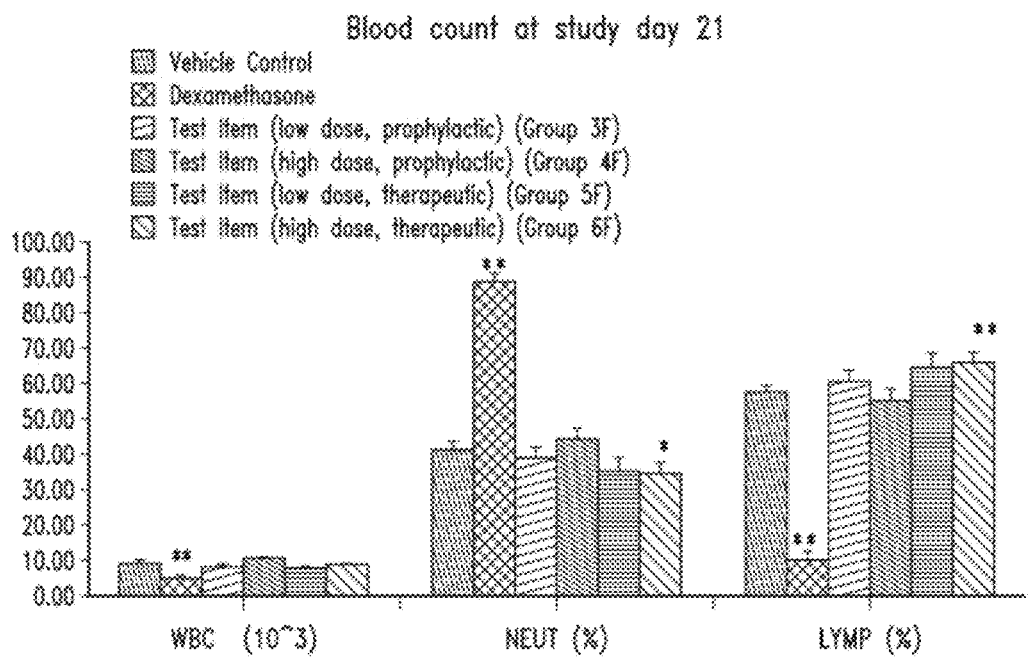
Figure 11A:
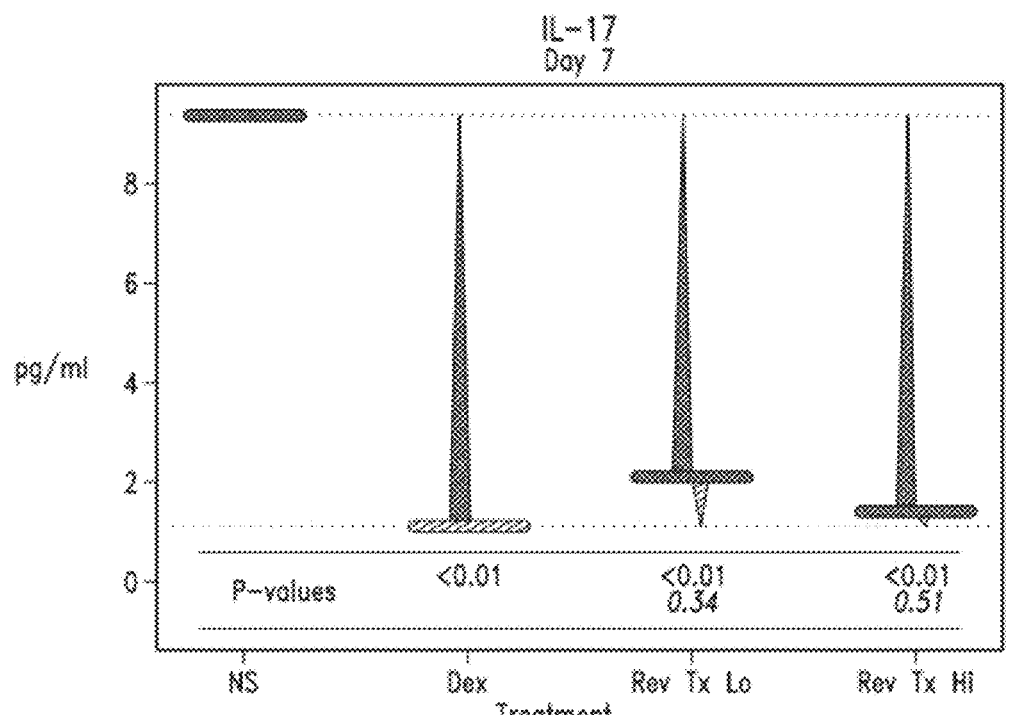
FIGS. 11A-H (A-D) show the effect that the inventive electrokinetic fluid (RNS-60) had on cytokine levels 7 days (A-D) and 18 days (E-H) after the EAE treatment regimen as used in experiment shown in FIGS. 7 and 8 was initiated. Panels A and E show the levels of IL-17 after treatment. Panels B and F show the levels of IL-1α after treatment. Panels C and G show the levels of IL-1β after treatment. Panels D and H show the levels of IL-4 after treatment.
Figure 11B:
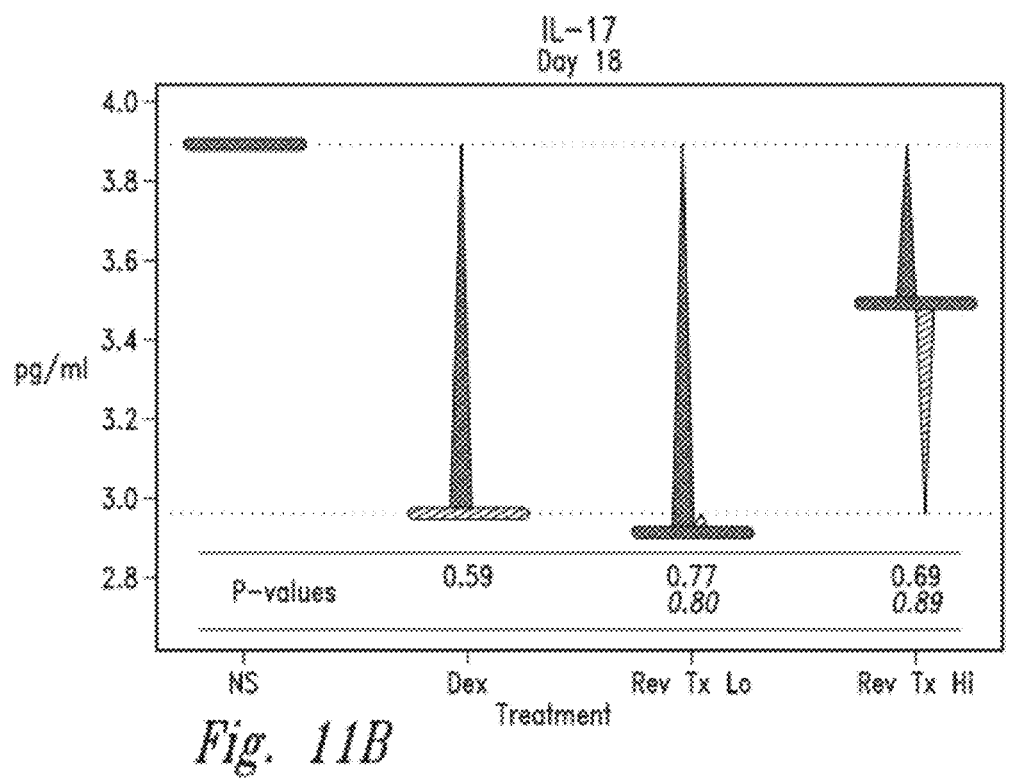
Figure 11C:
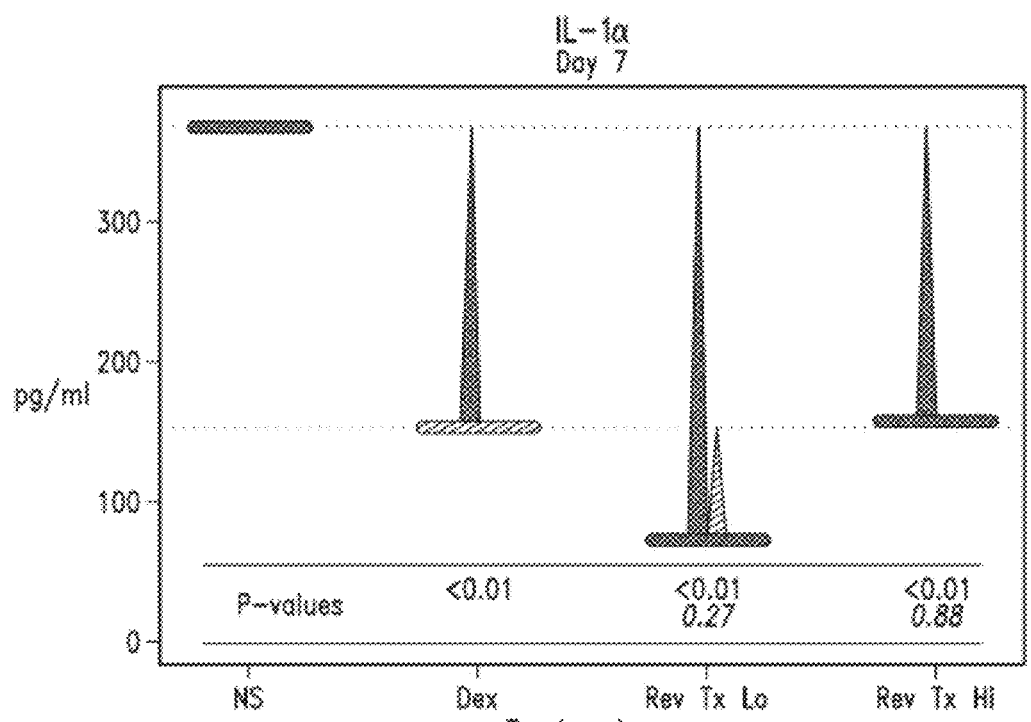
Figure 11D:
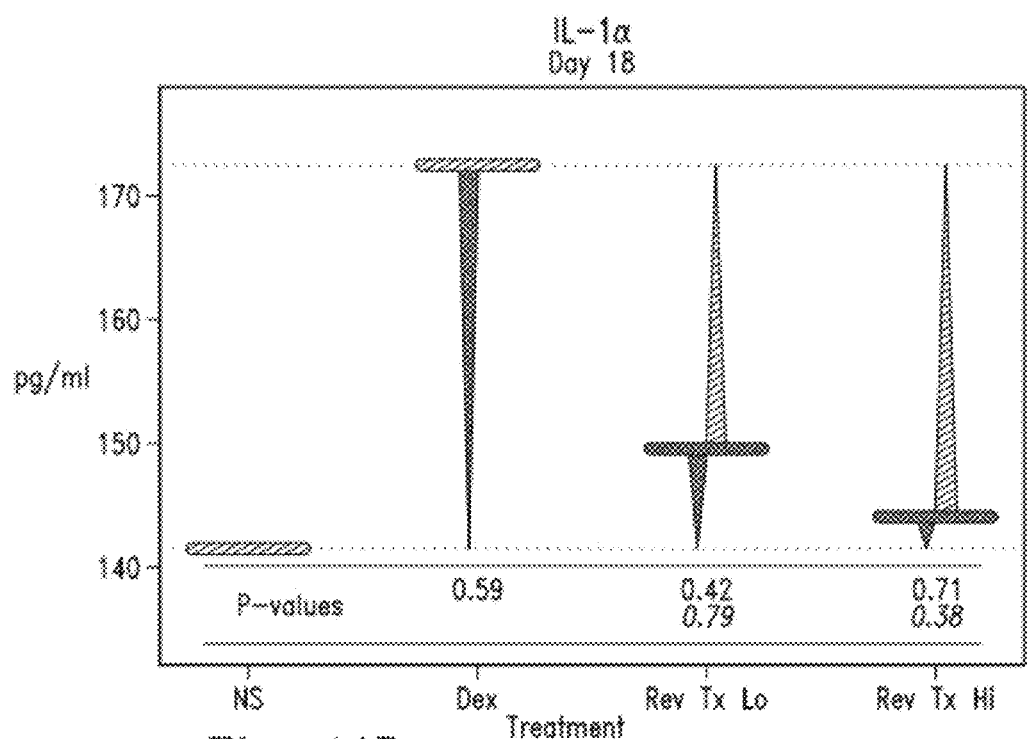
Figure 11E:
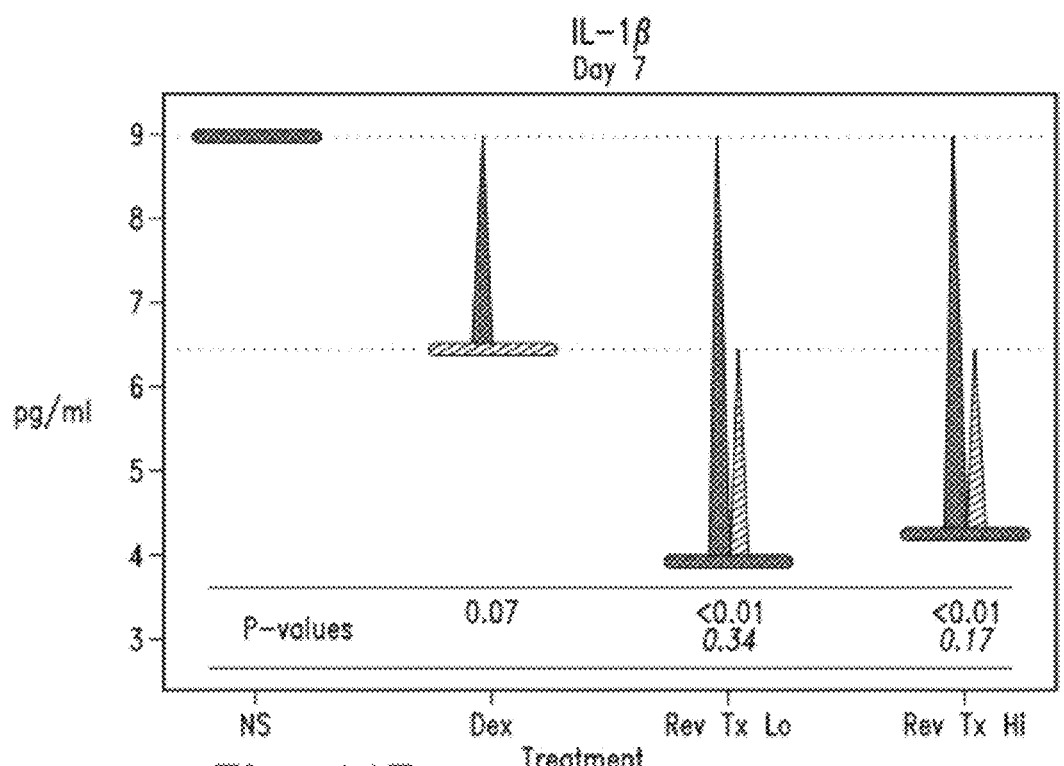
Figure 11F:
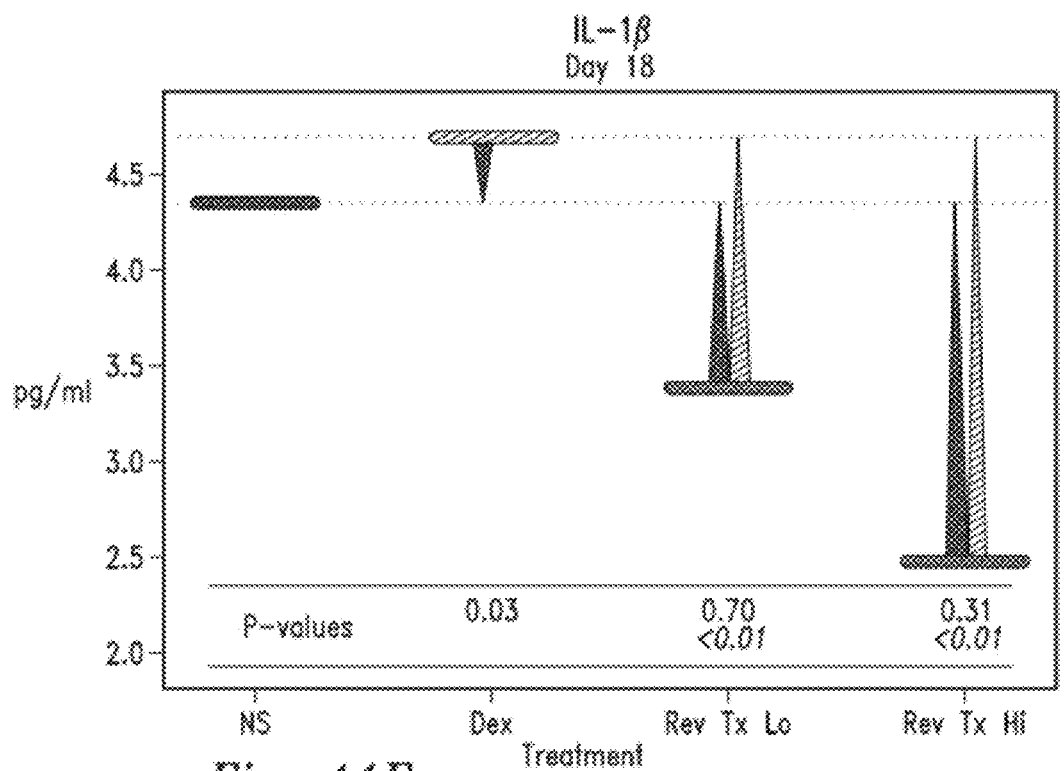
Figure 11G:
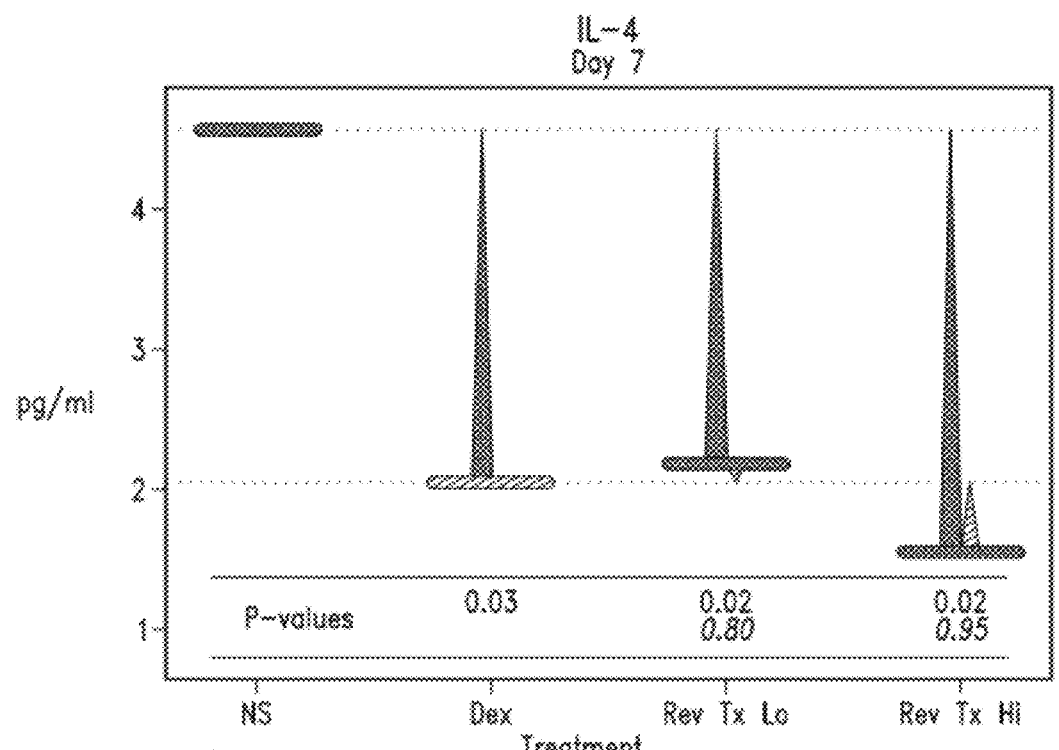
Figure 11H:
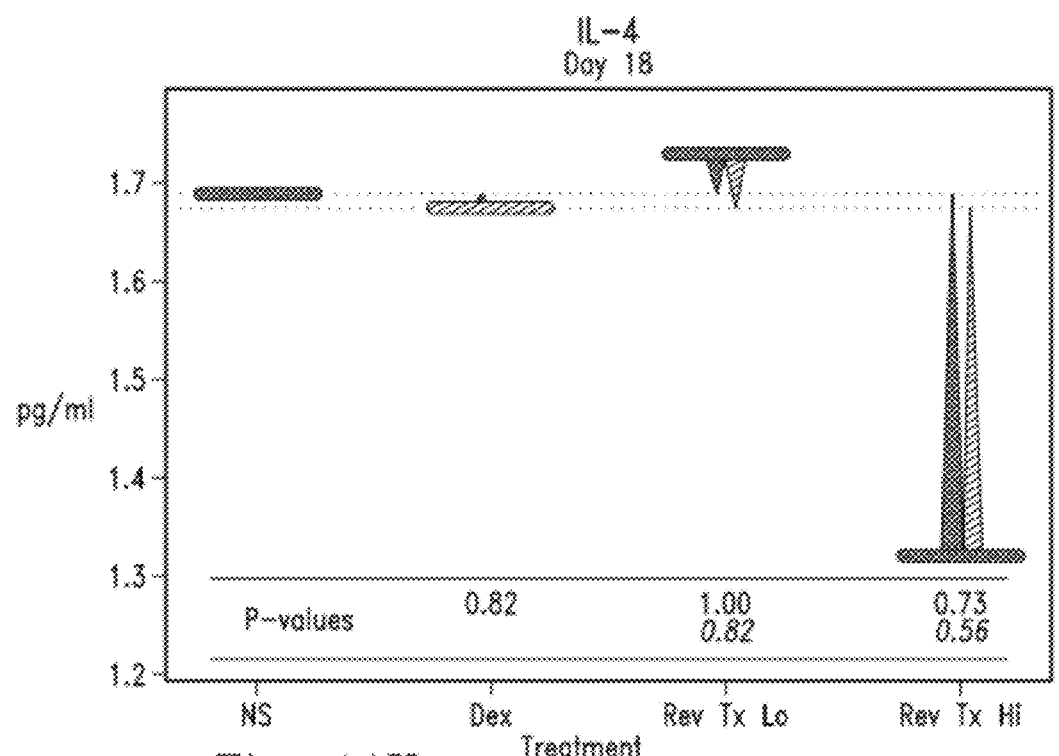

Body Weight Data:

FIG. 9 shows the body weight in grams (panel A) and as a percentage (panel B) based on 100 grams. After a slight reduction of the mean body weight of in the animals treated in this Example, the mean body weight began to increase until study termination. At study termination, the mean body weight gain was 20% in the Vehicle treated animals (Group 1F). Throughout the study, the Dexamethasone treatment group (Group 2F) which was administered starting on study day 0 had 10% mean body weight loss during the study. At study termination, the Dexamethasone treated animals lost 2% of mean body weight. The prophylactic, low dose treated group (Group 3F) showed up to 4% mean body weight loss on study days 1-3, and then gained 23% of the mean body weight by the day of study termination. The prophylactic, high dose treated group (Group 4F) showed up to 5% mean body weight loss on study days 1-3, and then gained 28% of the mean body weight by the day of study termination. The therapeutic, low dosed treated group (Group 5F) showed up to 4% mean body weight loss on study days 1-3, and then gained 21% of the mean body weight by the day of study termination. The therapeutic, high dose treated group (Group 6F) showed up to 4% mean body weight loss on Study Days 1-3, then gained 19% of the mean body weight by the day of study termination.

Thus the inventive electrokinetic fluid RNS-60 was found to be effective in sustaining the weight of rats subjected to the EAE rat model.

According to particular aspects of the present invention, therefore, the inventive electrokinetic compositions have substantial utility for treating, including alleviating and preventing, the symptoms of EAE in art-recognized rat models of human MS.

Example 9

The Inventive Electrokinetic Fluid was Shown to have Little Effect on the Level of White Blood Cells, Neutrophils, and Lymphocytes in Blood Samples Taken from Rat Subjected to the Art-Recognized Acute Experimental Allergic (Autoimmune) Encephalomyelitis (EAE) Rat MBP Model of Multiple Sclerosis (MS)

Overview:

This working EXAMPLE discloses the level of white blood cells, neutrophils, and lymphocytes in blood samples taken from rats during the experiment as described in Example 7. To determine whether the change in cytokine levels was due to an overall change in white blood cells, Applicants' took blood samples, throughout the experiment, from rats subjected to the EAE experiment.

Level of White Blood Cells, Neutrophils, and Lymphocytes:

FIGS. 10 A-D show the levels of white blood cells, neutrophils, and lymphocytes in blood samples that were collected throughout the EAE experiment.

White blood cells (WBC), neutrophils and lymphocytes were counted one hour after the Test Item was administered on study days 0 (panel A), 7 (panel B), 14 (panel C) and 21 (panel D). The maximum WBC count one hour after the animals were treated with Vehicle on Study Day 7 was 8.23±0.36 points. Treatment with Dexamethasone significantly reduced the average WBC count vs. Vehicle to 2.46±0.38 points ($p<0.05$). Therapeutic treatment with the Test Item at a low dose (Group 5F) significantly increased the average WBC count vs. Vehicle to 9.59±0.46 points ($p<0.1$). Therapeutic treatment with the Test Item at a high dose (Group 6F) significantly increased the average WBC count vs. Vehicle to 10.84±0.88 points ($p<0.05$).

The maximum WBC count one hour after animals were treated with Vehicle on study day 14 was 6.34±0.28 points. Treatment with Dexamethasone significantly reduced the average WBC count vs. Vehicle to 3.79±0.69 points ($p<0.05$). Prophylactic treatment with the Test Item at the high dose (Group 4F) significantly increased the average WBC count vs. Vehicle to 7.83±0.51 points ($p<0.05$). Therapeutic treatment with the Test Item at the low dose (Group 5F) significantly increased the average WBC count vs. Vehicle to 7.65±0.52 points ($p<0.05$). Therapeutic treatment with the Test Item at the high dose (Group 6F) significantly increased the average WBC count vs. Vehicle to 8.05±0.43 points ($p<0.05$). The maximum WBC count one hour after animals were treated with Vehicle on study day 21 was 9.09±0.75 points. Treatment with Dexamethasone significantly reduced the average WBC count vs. Vehicle to 5.12±0.57 points ($p<0.05$).

The maximum neutrophils count one hour after animals were treated with the Vehicle on study day 7 was 26.20±1.62 points. Treatment with Dexamethasone significantly increased the average neutrophils count versus vehicle to 65.38±4.62 points ($p<0.05$). Prophylactic treatment with the Test Item at the high dose (Group 4F) significantly increased the average neutrophils count versus vehicle to 31.90±0.96 points ($p<0.05$). Therapeutic treatment with the Test Item at the high dose (Group 6F) significantly increased the average neutrophils count versus vehicle to 33.90±2.79 points ($p<0.05$).

The maximum Neutrophils count one hour after animals were treated with Vehicle on study day 14 was 33.00±2.58 points. Treatment with Dexamethasone significantly increased the average neutrophils count vs. Vehicle to 73.10±3.15 points ($p<0.05$).

The maximum neutrophils count one hour after animals were treated with Vehicle on study day 21 was 41.40±2.32 points. Treatment with Dexamethasone significantly increased the average neutrophils count vs. Vehicle to 89.33±1.97 points ($p<0.05$). Therapeutic treatment with the Test Item at the high dose (Group 6F) significantly decreased the average neutrophils count vs. Vehicle to 34.60±3.08 points ($p<0.1$).

The maximum lymphocytes count one hour after treated with Vehicle on study day 7 was 73.20±1.95 points. Treatment with Dexamethasone significantly reduced the average lymphocytes count vs. Vehicle to 30.63±1.31 points ($p<0.05$). Prophylactic treatment with the Test Item at the high dose (Group 4F) significantly reduced the mean lymphocytes count vs. Vehicle to 68.30±1.42 points ($p<0.1$). Therapeutic treatment with the Test Item at the high dose (Group 6F) significantly reduced the average lymphocytes count vs. Vehicle to 64.80.±3.00 points ($p<0.05$).

The maximum lymphocytes count one hour after treated with Vehicle on study day 14 was 66.10±2.53 points. Treatment with Dexamethasone significantly reduced the average lymphocytes count vs. Vehicle to 26.80±3.23 points ($p<0.05$).

The maximum lymphocytes count one hour after treated with Vehicle on study day 21 was 57.50±2.09 points. Treatment with Dexamethasone significantly reduced the average lymphocytes count vs. Vehicle to 10.11±2.08 points ($p<0.05$). Therapeutic treatment with the Test Item at the high dose (Group 6F) significantly increased the average lymphocytes count vs. Vehicle to 66.20±2.74 points ($p<0.05$).

Thus the inventive electrokinetic fluid RNS-60 administered prophylactically and therapeutically at the high dose significantly increased the neutrophils count and significantly decreased the lymphocytes count versus the Vehicle at study day 7. The inventive electrokinetic fluid RNS-60 administered prophylactically at the high dose, and therapeutically at both doses, significantly increased the WBC count versus the Vehicle at study day 14. The Test Item RNS60 administered therapeutically at the high dose, significantly decreased the neutrophils count and increased the Lymphocytes count versus the Vehicle at study day 21. Thus the inventive electrokinetic fluid RNS-60 was found to have little effect on the overall levels of WBC, neutrophils, and lymphocytes.

Example 10

The Inventive Electrokinetic Fluid was Shown to Effect the Level of Certain Cytokines in Blood Samples Taken from Rat Subjected to the Art-Recognized Acute Experimental Allergic (Autoimmune) Encephalomyelitis (EAE) Rat MBP Model of Multiple Sclerosis (MS)

Overview:

This working EXAMPLE discloses the level of cytokines as discovered in blood samples taken from rats during the experiment as described in Example 7. The inventive electrokinetic fluid RNS-60 was evaluated in the therapeutic administration regimens, as described in Example 7. The inventive electrokinetic fluid RNS-60 was shown to affect the level of certain cytokines in blood samples taken from rat subjected to the EAE rat model.

Certain cytokines have been shown to have a role in Multiple Sclerosis. In particular interleukin 17 (IL-17), also known as CTLA-8 or IL-17A, has been demonstrated to have elevated levels in the central nervous system in acute and chronic EAE (Hofstetter, H. H., et al., *Cellular Immunology* (2005), 237:123-130). IL-17 is a pro-inflammatory cytokine which stimulates the secretion of a wide range of other cytokines from various non-immune cells. IL-17 is capable of inducing the secretion of IL-6, IL-8, PGE2, MCP-1 and G-CSF by adherent cells like fibroblasts, keratinocytes, epithelial and endothelial cells and is also able to induce ICAM-1 surface expression, proliferation of T cells, and growth and differentiation of CD34+ human progenitors into neutrophils when cocultured in presence of irradiated fibroblasts (Fossiez et al., 1998, *Int. Rev. Immunol.* 16, 541-551). IL-17 is predominantly produced by activated memory T cells and acts by binding to a ubiquitously distributed cell surface receptor (IL-17R) (Yao et al., 1997, Cytokine, 9, 794-800). A number of homologues of IL-17 have been identified which have both similar and distinct roles in regulating inflammatory responses. For a review of IL-17 cytokine/receptor families see Dumont, 2003, Expert Opin. Ther. Patents, 13, 287-303.

IL-17 may contribute to a number of diseases mediated by abnormal immune responses, such as rheumatoid arthritis and air-way inflammation, as well as organ transplant rejection and antitumour immunity. Inhibitors of IL-17 activity are well known in the art, for example an IL-17R:Fc fusion protein was used to demonstrate the role of IL-17 in collagen-induced arthritis (Lubberts et al., J. Immunol. 2001, 167, 1004-1013) and neutralising polyclonal antibodies have been used to reduce peritoneal adhesion formation (Chung et al., 2002, J. Exp. Med., 195, 1471-1478). Neutralising monoclonal antibodies are commercially available (R&D Systems UK).

Thus based on the role IL-17 plays in the pathogenesis of MS, Applicants' examined the effect that inventive electrokinetic fluid RNS-60 had on levels of IL-17 in blood samples taken from rats in the EAE study.

Cytokine Data:

Levels of various cytokines in the blood were analyzed during the study. In brief, all animals were bled 1-hour post injection and plasma was collected in heparinized vials. 100 μl samples were analyzed for various inflammatory cytokines by Luminex technology (using Procarta rat cytokine assay kit PC4127 from Panomics) which enables measurement of multiple cytokines from the same sample, simultaneously. Due the non-Gaussian distributed data and occasional results below the assay detection threshold, the nonparametric Cox regression model for censored data was adapted to compare the different fluids. As show in FIGS. 11A-H, levels of IL1a, IL1b, and IL17 were most notably reduced by both therapeutic treatment doses (high and low) of RNS60. Clinical manifestation of MBP induced EAE starts around day 10 and peaks around day 18. Hence, we considered the day 7 (just prior to disease manifestation) and day 18 (around the peak of the disease) to be the most important time points for cytokine analysis. Systemic levels of IL1a, IL1b and IL17 on days 7 and 18, from 10 animals/group are presented in FIGS. 11A-H . . . .

IL-1 is one of the major pro-inflammatory cytokines and is an upstream mediator of the innate immune responses. IL-1 induces the production of various growth and trophic factors, inflammatory mediators, adhesion molecules and other cytokines directly and indirectly, as well as using a positive feedback loop (A. Basu at al., The type 1 interleukin-1 receptor is essential for the efficient activation of microglia and the induction of multiple proinflammatory mediators in response to brain injury, *J. Neurosci.* 22 (2002), pp. 6071-6082; P. N. Moynagh, The interleukin-1 signaling pathway in astrocytes: a key contributor to inflammation in the brain, *J. Anat.* 207 (2005), pp. 265-269). These include important modulators such as NGF, ICAM 1, IL6, TNFa, CSF etc. The progression of MS involves the activation of auto-antigen-reactive T cells in the periphery, followed by invasion into the CNS. IL-1 is crucial in the development of MS as they participate not only in myelin-specific T cell activation but also represent the main mediator of macrophage activation in the periphery [R. Furlan et al., HSV-1-mediated IL-1 receptor antagonist gene therapy ameliorates MOG(35-55)-induced experimental autoimmune encephalomyelitis in C57BL/6 mice, *Gene Ther.* 14 (2007), pp. 93-98)). In EAE models for MS, both IL-1α and IL-1β have been shown to be mediators of the inflammatory process. Peripheral levels of IL-1β correlate with the clinical course and IL-1β reactivity has been shown during EAE in CNS-infiltrating macrophages and in resident microglial cells ((C. A. Jacobs et al., Experimental autoimmune encephalomyelitis is exacerbated by IL-1 alpha and suppressed by soluble IL-1 receptor, *J. Immunol.* 146 (1991), pp. 2983-2989)). Therefore, IL-1 is a suitable therapeutic target in EAE and MS. A non-selective inhibitory mechanism of IL-1 has been shown in existing therapeutic agents for MS; that is interferon beta, anti-inflammatory glucocorticoids, immunosuppressants, atorvastatin and omega-3 polyunsaturated fatty acids [F. L. Sciacca et al., Induction of IL-1 receptor antagonist by interferon beta: implication for the treatment of multiple sclerosis, *J. Neurovirol.* 6 (Suppl. 2) (2000), pp. S33-S37.; R. Pannu et al., Attenuation of acute inflammatory response by atorvastatin after spinal cord injury in rats, *J. Neurosci. Res.* 79 (2005), pp. 340-350; A. P. Simopoulos, Omega-3 fatty acids in inflammation and autoimmune diseases, *J. Am. Coll. Nutr.* 21 (2002), pp. 495-505)). As demonstrated in FIG. 11 C-F, IV administration of RNS60 effectively lowers the systemic levels of both IL1α and IL1β. For IL1α, RNS60 treatment lowered the blood level significantly compared to the vehicle treated group, and was as effective as dexamethasone at this time point. However at the 18 day time point, the treatment has no significant effect on the IL1α systemic level. Systemic levels of IL1β were also reduced significantly after 7 days of IV treatment of RNS60, to the levels comparable to the dexamethasone treatment groups, without any sign of toxic side effects. Although the same trend was noted at the 18 day time point, the differences were not statistically significant when compared to the control group. IL-17 is a also crucial effector cytokine with potent proinflammatory effects. It induces the expression of other proinflammatory cytokines such as tumor necrosis factor-α and chemokines, attracts neutrophilic leukocytes, and enhances the maturation of dendritic cells (Kolls J K, Lindén A. Interleukin-17 family members and inflammation. *Immunity.* 2004 October; 21(4):467-76). IL-17-producing cells are thought to be essential inflammatory mediators in autoimmune diseases such as collagen-induced arthritis, colitis, psoriasis, and EAE. T helper17 cells in EAE are CD4+ cells and they are present both in the immune periphery and in the inflamed central nervous system in EAE. Moreover, neutralization of IL-17 ameliorates clinical disease, a finding that is paralleled by reduced EAE severity in IL-17-deficient animals ((from Gold and Lühder, Interleukin-17—Extended Features of a Key Player in Multiple Sclerosis Am J. Pathol. 2008 January; 172(1): 8-10). 7 day IV treatment with RNS60 caused a significant reduction in IL17 levels in blood, once again to a level similar to dexamethasone treated animals. The same was followed even after 18 days of treatment although the results were not statistically significant. It is important to note that RNS60 is effective not only in lowering the IL1 levels but the combination of the two key cytokines in EAE, IL1 and IL17 with no notable toxic side effects even after 21 days of IV injections.

In addition to IL1 and IL17, a number of other molecules that play critical role in inflammation of the nervous system are also modulated by RIS60. These include Rantes, KC, NGF and ICAM (data not shown).

Thus the inventive electrokinetic fluid RNS-60 had a significant effect on levels of IL-17 in blood samples taken from rats in the EAE study. In addition, since IL-17 stimulates the secretion of IL-6, IL-8, PGE2, MCP-1 and G-CSF, it seems likely that the inventive electrokinetic fluid RNS-60 would have a significant effect on the level of these cytokines in blood. According to particular aspects of the present invention, therefore, the inventive electrokinetic compositions have substantial utility for treating, including alleviating and preventing, the symptoms of EAE in art-recognized rat models of human MS.

Example 11

RNS-60 was Shown by Fluorescence-Activated Cell Sorting (FACS) Analysis to have a Pronounced Effect on Expression of Cell Surface Receptors: CD193 (CCR3); CD154 (CD40L); CD11B; and CD3

Overview.

Applicants used Fluorescence-Activated Cell Sorting (FACS) analysis to compare the levels of expression of cell surface receptors, CD193 (CCR3); CD154 (CD40L); CD11B; and CD3, on white blood cells incubated with either the inventive electrokinetic fluid (RNS-60) or normal saline control fluid.

Methods:

Ficoll-hypaque separated PBMC (apheresis—All Cells) preincubated approximately 1 hour in 30% solutions of RNS60 or Normal Saline (NS);

PBMC activated with 2 µg/ml of PHA-L for 24 or 40 hours;

Cells collected and washed into blocking/staining buffer, stained and fixed; and Cells were analyzed by flow cytometry.

Results:

With respect to CD193 (CCR3) the receptor is substantially down-regulated in the presence of RNS-60 when compared to the level of the receptor expression in the normal saline control. This down regulation affects the phosphorylation of MAPK p38 (data not shown) which in turn down-regulates eotaxin (e.g., see Example 13 and FIG. 57 of Applicants' published patent application WO2009/055729, published on Apr. 30, 2009) which in turn down regulates IL 5 and as well alters eosinophil counts, which is one of the factors that, that example, alters the bronchoconstrictive response.

As discussed in Example 13 of Applicants' published patent application WO2009/055729, published on Apr. 30, 2009 in the context of the ovalbumin challenge model, RNS-60 decreased the serum eotaxin levels in the OVA challenged groups when compared to the effect of normal saline. Therefore, according to particular aspects, RNS-60 has the potential to decrease both the ligand eotaxin and its receptor CCR3.

With respect to CD154 (CD40L), the receptor is down-regulated in the presence of RNS-60 when compared to the level of the receptor expression in normal saline.

With respect to CD11B the receptor is down-regulated in the presence of RNS-60 when compared to the level of the receptor expression in normal saline.

With respect to CD3 the receptor is down-regulated in the presence of RNS-60 when compared to the level of the receptor expression in normal saline.

According to particular aspects, and as described elsewhere in the working Examples herein, the inventive electrokinetic compositions have substantial utility for reducing inflammation. Without being bound by mechanism, for example, and as discussed elsewhere herein, IL7R dimerizes with the cytokine receptor-like factor 2 gene (CRLF2) to form the TSLP receptor (Al Shami et al. (2004) J. Exp. Med. 200:159-168). TSLP is an IL7-like cytokine that drives immature B cell development in vitro and, in myeloid dendritic cells, can promote naive CD4+ T cells to differentiate into a T helper type 2 (Th2) phenotype and promote the expansion of CD4+ Th2 memory cells (Huston et al. (2006) Curr. Allergy Asthma Rep. 6:372-376). TSLP is thought to trigger dendritic cell-mediated Th2-type inflammatory responses and is considered as a master switch for allergic inflammation (Koyama et al. (2007) Biochem. Biophys. Res. Commun. 357:99-104), which is relevant to the etiology of MS (see, e.g., Gregory et al. *Nature Genetics,* 39:1083-1091; published online 29 Jul. 2007 incorporated by reference herein; association of IL7Rα allele with M.S.). In further aspects, the inventive electrokinetic compositions have substantial utility for modulating (e.g., lowering) Matrix MetalloProteinase 9 (MMP-9). In Multiple Sclerosis (MS), Matrix MetalloProteinase (MMP) activity in tissues is the result of a balance between MMPs and their Tissue Inhibitors (TIMPs). MMP-9 predominates in acute MS lesions and is inhibited by TIMP-1, while MMP-2 likely participate in the remodeling of the ExtraCellular Matrix (ECM) such as in chronic disease and is inhibited by TIMP-2 (see e.g., Avolio et al., *J NeuroImmunol,* 136:46-53, 2003, incorporated by reference herein).

According to further aspects of the present invention, therefore, the inventive electrokinetic compositions have substantial utility for treating, including alleviating and preventing, the symptoms of MS in afflicted mammals (preferably humans).

According to yet further aspects, the inventive electrokinetic compositions can be administered along with at least one additional M.S. therapeutic agent as described elsewhere herein According to further aspects of the present invention, therefore, the inventive electrokinetic compositions have substantial utility for treating, including alleviating and preventing, the symptoms of inflammatory neurodegenerative diseases (e.g., Alzheimer's, Parkinson's, Amyloidosis type disorders, as defined elsewhere herein) in afflicted mammals (preferably humans).

Example 12

The Inventive Electrokinetic Fluid (e.g., RNS60) was Shown to Inhibit the Expression of Both iNOS and IL-1β in a Dose-Dependent Manner in Microglial Cells Overview:

According to particular aspects as described herein, the inventive electrokinetic fluids have substantial utility for treating Parkinson's disease (PD).

Parkinson's disease (PD) is one of the most devastating neurodegenerative disorders in humans. PD may appear at any age, but it is uncommon in people younger than 30. Clinically, PD is characterized by tremor, bradykinesia, rigidity and postural instability. Pathologically, it is indicated by gliosis and progressive degeneration of the dopaminergic neurons associated with the presence of intracytoplasmic inclusions (Lewy bodies) in the substantia nigra pars compacta (SNpc). In postmortem PD brain, dying neurons have been reported to display morphological characteristics of apoptosis, including cell shrinkage, chromatin condensation, and DNA fragmentation. Therefore, development of effective neuroprotective therapeutic approaches halt the disease progression is of paramount importance. The MPTP mouse model has substantial utility for testing and validating therapeutic approaches against PD.

Microglial activation plays an important role in the pathogenesis of Parkinson's disease (PD) as well as other neurodegenerative disorders. Particular features of PD are modeled in 1-methyl-4-phenyl-1,2,3,6-tetrahydropyridine (MPTP)-intoxicated animals. The neurotoxic effect of MPTP depends on its conversion into MPP$^+$. In glial cells, monoamine oxidase B (MAO-B) converts MPTP to MPP$^+$, which then activates glial cells, and recently, it has been shown that MPP$^+$ induces the expression of proinflammatory molecules in microglia.

In this working EXAMPLE, the ability of RNS60 to modulate the expression of proinflammatory molecules in MPP$^+$-stimulated microglial cells was confirmed.

Materials and Methods:

Briefly, mouse BV-2 microglial cells were incubated with different concentrations of RNS60 and normal saline (NS) for 1 h followed by stimulation with 2 μM MPP$^+$ under serum-free conditions.

Figure 12:
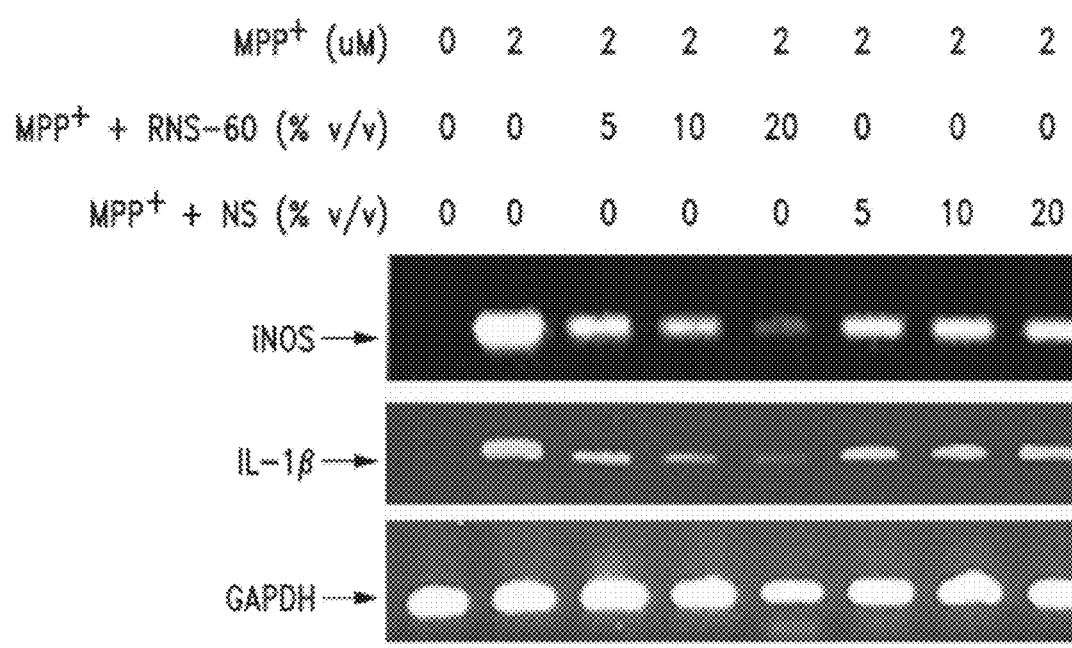
FIG. 12 shows that the inventive electrokinetic fluid (RNS-60), but not control normal saline (NS), attenuates MPP$^+$-induced expression of inducible nitric oxide synthase (iNOS) and interleukin-1β (IL-1β) in mouse microglial cells (BV-2 microglial cells).

Results:

As evidenced by semi-quantitative RT-PCR analysis in FIG. 12, MPP$^+$ alone induced the expression of inducible nitric oxide synthase (iNOS) and interleukin-1β (IL-1β) mRNAs in mouse BV-2 microglial cells. Significantly, RNS60 inhibited the expression of both iNOS and IL-1β in a dose-dependent manner in microglial cells (FIG. 12). By contrast, under similar experimental condition, the normal saline control (NS) had no effect on the expression of these two proinflammatory genes (FIG. 12) indicating the specificity of the effect.

Specifically, FIG. 12 shows that the inventive electrokinetic fluid (RNS-60), but not control normal saline (NS), attenuates MPP$^+$-induced expression of inducible nitric oxide synthase (iNOS) and interleukin-1β (IL-1β) in mouse microglial cells. BV-2 microglial cells preincubated with different concentrations of RNS60 and normal saline (NS) in serum-free media for 1 h were stimulated with MPP+ (a Parkinsonian toxin). After 6 h of stimulation, total RNA was isolated and the mRNA expression of iNOS and IL-1β was analyzed by semi-quantitative RT-PCR. Results represent three independent experiments.

According to particular aspects therefore, because MPP$^+$ is a Parkinsonian toxin, these results indicate that RNS60 has a protective effect in an art-recognized MPTP-induced mouse model of Parkinson's disease.

According to particular aspects, the inventive electrokinetic fluids have substantial utility for treating Parkinson's disease (PD).

Example 13

The Inventive Electrokinetic Fluid (e.g., RNS60) was Shown to Protect Neurons from Amyloid-β Toxicity Overview:

According to particular aspects as described herein, the inventive electrokinetic fluids have substantial utility for treating Alzheimer's disease (AD).

Alzheimer's disease (AD) is a neurodegenerative disorder resulting in progressive neuronal death and memory loss. Increased TUNEL staining in postmortem AD brains indicates that neurons in the brains of AD patients die through apoptosis. Fibrillar amyloid-β peptides participate in the pathophysiology of AD. Neuropathologically, the disease is characterized by neurofibrillary tangles and neuritic plaques composed of aggregates of β-amyloid (Aβ) protein, a 40-43 amino acid proteolytic fragment derived from the amyloid precursor protein, and phosphorylated tau. It has been found that over-expression of the Aβ peptides intracellularly in transgenic mice causes chromatin segmentation, condensation, and increased TUNEL staining. Cell culture studies have also shown that Aβ peptides are apoptotic and cytotoxic to neuronal cells, and It has been shown that fibrillar Aβ1-42 peptides are capable of inducing apoptosis in neuronal cells.

Additionally, studies are increasingly being directed at characterizing the link between inflammation and AD, and widespread glial activation has been found around plaques and tangles.

In this EXAMPLE, the effect of RNS60 in blocking Aβ(1-42)-induced apoptosis in human SHSY5Y nerve cells was confirmed.

Materials and Methods:

Fragmented DNA of SHS5Y human neuronal cells was detected in situ by the terminal deoxynucleotidyltransferase (TdT)-mediated binding of 3'-OH ends of DNA fragments generated in response to fibrillar Aβ1-42, using a commercially available kit (TdT FragEL™) from Calbiochem. Briefly, cover slips were treated with 20 μg/ml proteinase K for 15 min at room temperature and washed prior to TdT staining.

Figure 13:
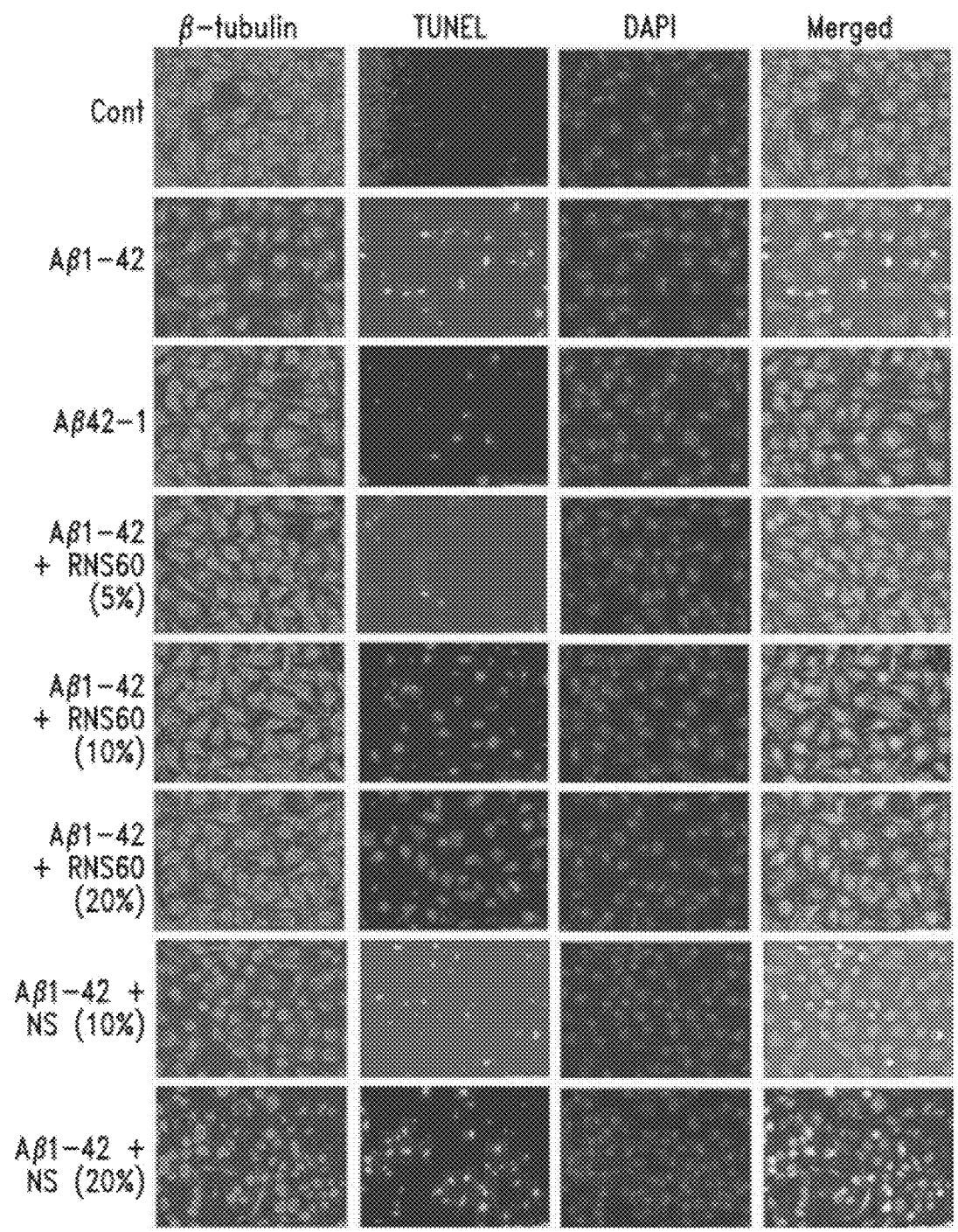
FIG. 13 shows that RNS60, but not normal saline control (NS), suppresses fibrillar Aβ(1-42)-mediated apoptosis of human SHSY5Y neuronal cells. After differentiation, SHSY5Y cells were incubated with different concentrations of either RNS60 or NS for 1 h followed by insult with 1 μM fibrillar Aβ(1-42) peptides. After 18 h of treatment, apoptosis was monitored by TUNEL (Calbiochem). Aβ(42-1) peptides were also incubated as control. Results represent three independent experiments.

Results:

As demonstrated in FIG. 13, fibrillar Aβ1-42 peptides markedly induced the formation of apoptotic bodies in neuronal cells. We also observed loss of neuronal processing after Aβ1-42 treatment ($2^{nd}$ row; FIG. 13). In contrast, reverse peptides Aβ42-1 were unable to induce neuronal apoptosis and loss of processes ($3^{rd}$ row; FIG. 13). Significantly, RNS60 at different doses tested markedly blocked Aβ(1-42)-induced apoptosis and preserved processes in neuronal cells ($4^{th}$, $5^{th}$ & $6^{th}$ rows; FIG. 13). By contrast, normal saline control fluid (NS) had no effect on Aβ(1-42)-induced apoptosis and loss of processes ($7^{th}$ & $8^{th}$ rows; FIG. 13).

Specifically, FIG. 13 shows that RNS60, but not normal saline control (NS), suppresses fibrillar Aβ(1-42)-mediated apoptosis of human SHSY5Y neuronal cells. After differentiation, SHSY5Y cells were incubated with different concentrations of either RNS60 or NS for 1 h followed by insult with 1 μM fibrillar Aβ(1-42) peptides. After 18 h of treatment, apoptosis was monitored by TUNEL (Calbiochem). Aβ(42-1) peptides were also incubated as control. Results represent three independent experiments.

These results indicate that the etiological reagent of AD (fibrillar Aβ1-42) induces apoptosis in neurons via an RNS60-sensitive pathway.

According to particular aspects, the inventive electrokinetic fluids have substantial utility for treating Alzheimer's disease (AD).

Example 14

The Inventive Electrokinetic Fluid was Shown to be Substantially Efficacious in Suppressing Clinical Score in a Dose-Responsive Manner in an Art-Recognized Mouse MOG Model of Multiple Sclerosis (MS)

Overview:

In this working EXAMPLE, the inventive electrokinetic fluid RNS-60 was evaluated at two doses, in therapeutic administration regimens, in an art-recognized experimental allergic encephalomyelitis (EAE) mouse MOG model of Multiple Sclerosis (MS).

Materials and Methods:

Experimental allergic encephalomyelitis (EAE) is a central nervous system (CNS) autoimmune demyelinating disease that mimics many of the clinical and pathologic features of multiple sclerosis (MS). The MOG murine model consists of a sensitization period, induced by the single subcutaneous (SC) injection of MOG emulsified in complete Freund's adjuvant (CFA) on study day 0 (200 μg MOG/300 μg CFA injected at a total dose volume of 200 μl/animal delivered as 2×100 μl subcutaneous bilateral injections over the paralumbar region); followed by intraperitoneal (IP) supplemental immunostimulation with pertussis toxin (PT) at 20 μg/kg (approximately 400 ng/mouse) via intraperitoneal (IP) injection once at the time of EAE induction on study day 0 and again, 48 hours later on study day 2 (Gilgun-Sherki Y. et al., *Neurosciences Research* 47:201-207, 2003). Animals were then treated with RNS60 IV infusion at indicated in FIG. 14. Animals used were Female C57BL/6J mice from Harlan Laboratories Israel, Ltd. (10 animals/group); young adults; 8-9 weeks old at study initiation.

All the animals were examined for signs of neurological responses and symptoms prior to EAE induction (study day 0) and thereafter examined on a daily basis throughout the 35-day observation period. EAE reactions were scored and recorded according to the art-recognized 0-15 scale in ascending order of severity. The clinical score was determined by summing the score of each section (see, e.g., Weaver et al., *FASEB* 2005; *The FASEB Journal* express article 10.1096/fj.04-2030fje. Published online Aug. 4, 2005).

Figure 14:
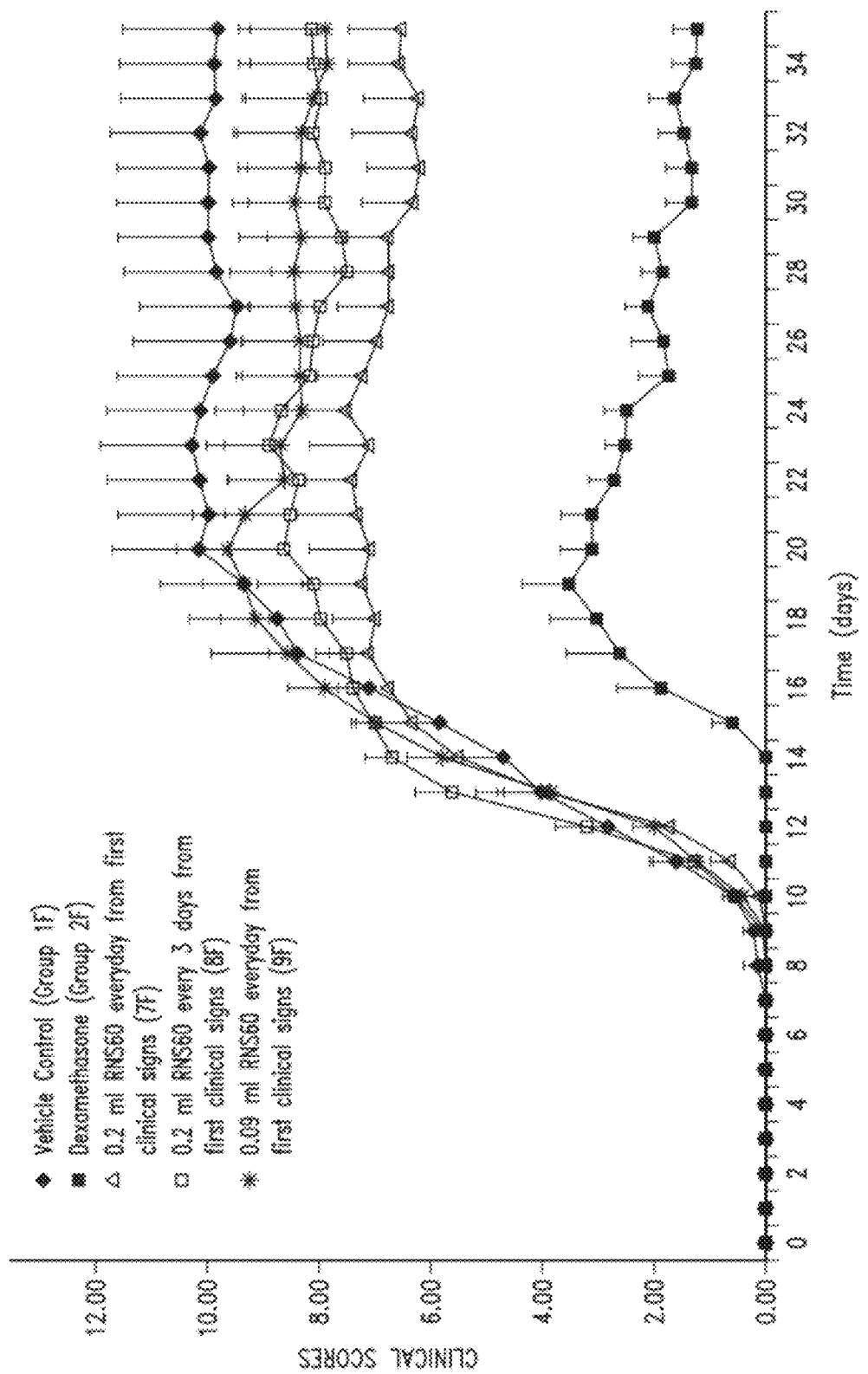
FIG. 14 shows that RNS60, but not Vehicle control (Vehicle), is substantially efficacious in suppressing clinical score in a dose-responsive manner in an art-recognized experimental allergic encephalomyelitis (EAE) mouse MOG model of Multiple Sclerosis (MS). Both high and low dose therapeutic daily administration of RNS-60, as well as the high dose administration of RNS-60 every three days (administration or RNS-60 in all instances beginning concomitant with first clinical signs), showed a marked decrease of clinical score (open diamonds=Vehicle control; open squares=dexamethasone positive control; light "x"s=low dose (0.09 ml RNS60) daily administration from onset of clinical signs; dark "x"s=high dose (0.2 ml RNS60) administration every three days from onset of clinical signs; and open triangles=high dose (0.2 ml RNS60) daily administration from onset of clinical signs).

Results:

FIG. 14 shows that RNS60, but not Vehicle control (Vehicle), is substantially efficacious in suppressing clinical score in a dose-responsive manner in an art-recognized mouse MOG model of Multiple Sclerosis (MS). Both high and low dose therapeutic daily administration of RNS-60, as well as the high dose administration of RNS-60 every three days (administration or RNS-60 in all instances beginning concomitant with first clinical signs), showed a marked decrease of clinical score (open diamonds=Vehicle control; open squares=dexamethasone positive control; light "x"s=low dose (0.09 ml RNS60) daily administration from onset of clinical signs; dark "x"s=high dose (0.2 ml RNS60) administration every three days from onset of clinical signs; and open triangles=high dose (0.2 ml RNS60) daily administration from onset of clinical signs).

In comparison with the MBP model of Example herein above, this mouse MOG model is known in the art for its ability to mimic the characteristic axonal damage of MS which the MBP model does not show, and extends the observed therapeutic efficacy over longer periods (28-30 days compared to 21 days with the MBP model). According to further aspects, RNS60, but not Vehicle control (Vehicle), is substantially efficacious in reducing axonal damage in this mouse MOG model.

According to particular aspects of the present invention, the inventive electrokinetic compositions have substantial utility for treating, including alleviating and preventing, symptoms in an art-recognized mouse model of human MS. According to further aspects of the present invention, the inventive electrokinetic compositions have substantial utility for treating, including alleviating and preventing, the symptoms of MS in afflicted mammals (preferably humans).

In yet further aspects, the inventive electrokinetic compositions cross the Blood Brain Barrier (BBB), and thus provide a novel method for treating inflammatory conditions of the central nervous system.

Example 15

RNS-60 was Shown by Fluorescence Activated Cell Sorting (FACS) Analysis to have a Pronounced Effect on Expression of Cell Surface Receptors: CD193 (CCR3); CD154 (CD40L); CD11B; and CD3)

Overview.

Applicants used Fluorescence-Activated Cell Sorting (FACS) analysis to compare the levels of expression of cell surface receptors, CD193 (CCR3); CD154 (CD40L); CD11B; and CD3, on white blood cells incubated with either the inventive electrokinetic fluid (RNS-60) or normal saline control fluid.

Methods:

Ficoll-hypaque separated PBMC (apheresis—All Cells) preincubated approximately 1 hour in 30% solutions of RNS60 or Normal Saline (NS);

PBMC activated with 2 μg/ml of PHA-L for 24 or 40 hours;

Cells collected and washed into blocking/staining buffer, stained and fixed; and Cells were analyzed by flow cytometry.

Figure 15A:
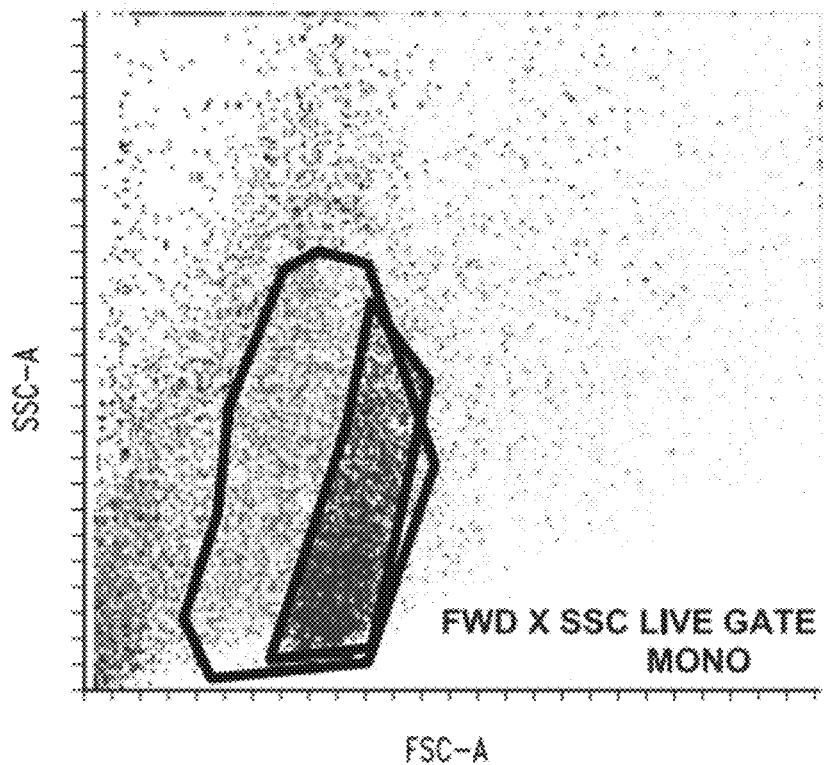
FIGS. 15 A-B demonstrate the results of Fluorescence-Activated Cell Sorting (FACS) analysis wherein the levels of expression of the cell surface receptor, CD193 (CCR3), on white blood cells was compared using either normal saline or RNS-60. The X-axis represents the log fluorescence of the sample and the Y-axis represents the events of fluorescence that occur in the sample.
Figure 15B:
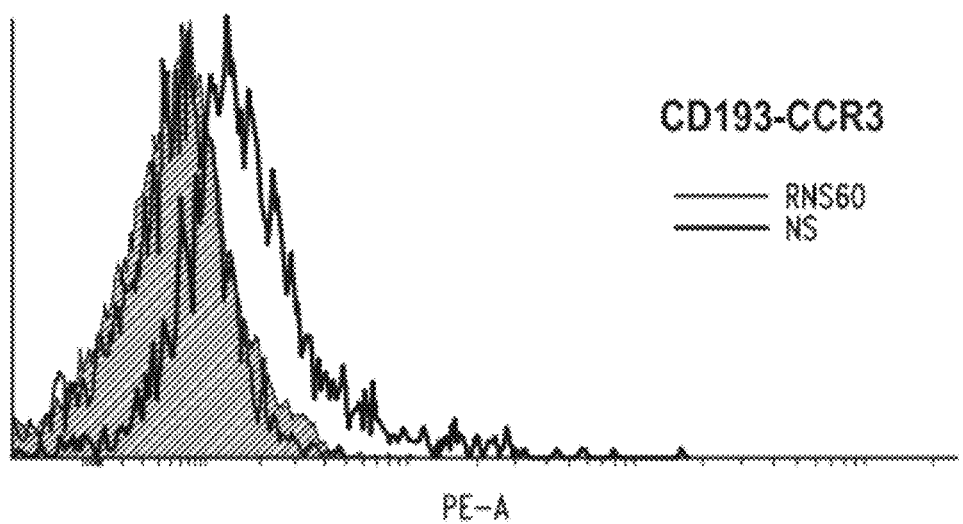

Results:

With respect to CD193 (CCR3), as shown in FIG. 15 B, the receptor is substantially down-regulated in the presence of RNS-60 when compared to the level of the receptor expression in the normal saline control. This down regulation affects the phosphorylation of MAPK p38 (data not shown) which in turn down-regulates eotaxin (e.g., see Example 4) which in turn down regulates IL 5 (data not shown) and as well alters eosinophil counts (e.g., see Example 4), which is one of the factors that, that example, alters the bronchoconstrictive response.

As discussed above in Example 4 in the context of the ovalbumin challenge model, RNS-60 decreased the serum eotaxin levels in the OVA challenged groups when compared to the effect of normal saline. Therefore, according to particular aspects, RNS-60 has the potential to decrease both the ligand eotaxin and its receptor CCR3.

Figure 16A:
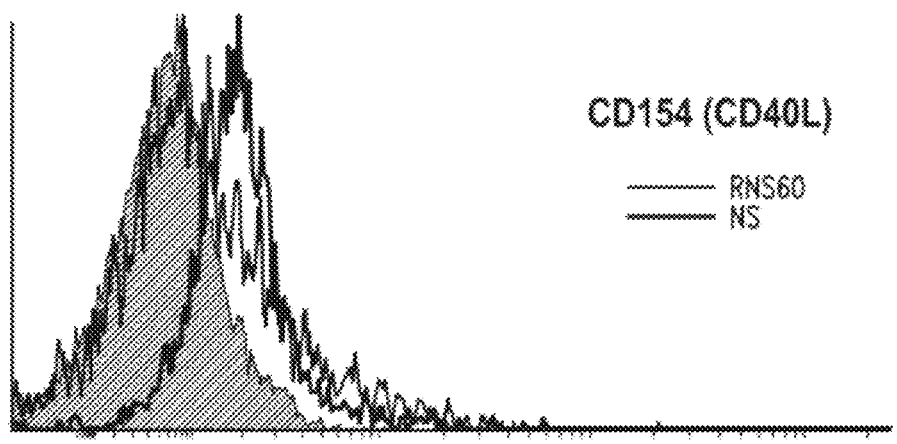
FIGS. 16 A-C demonstrate the results of Fluorescence-Activated Cell Sorting (FACS) analysis wherein the levels of expression of cell surface receptors, CD154 (CD40L) (panel A); CD11B (panel B); and CD3 (panel C), on white blood cells was compared using either normal saline or RNS-60. The X-axis represents the log fluorescence of the sample and the Y-axis represents the events of fluorescence that occur in the sample.
Figure 16B:
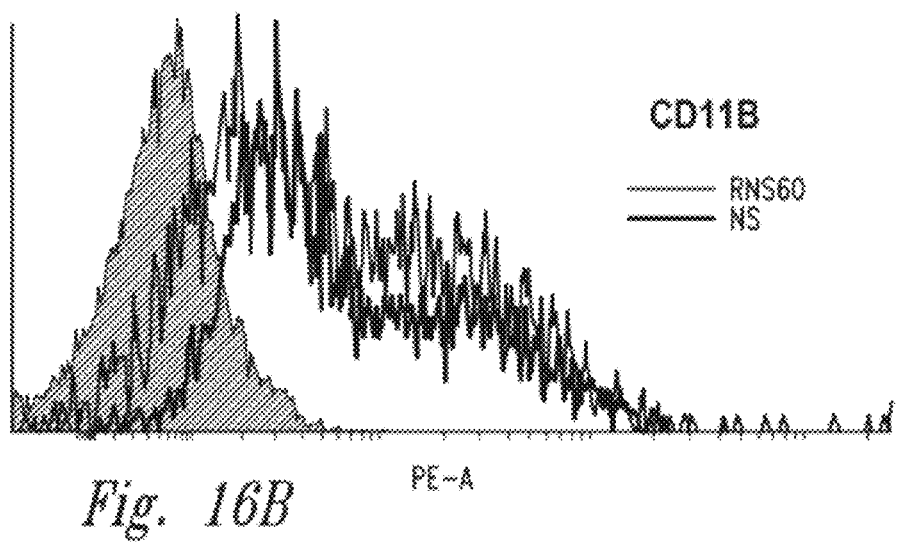
Figure 16C:
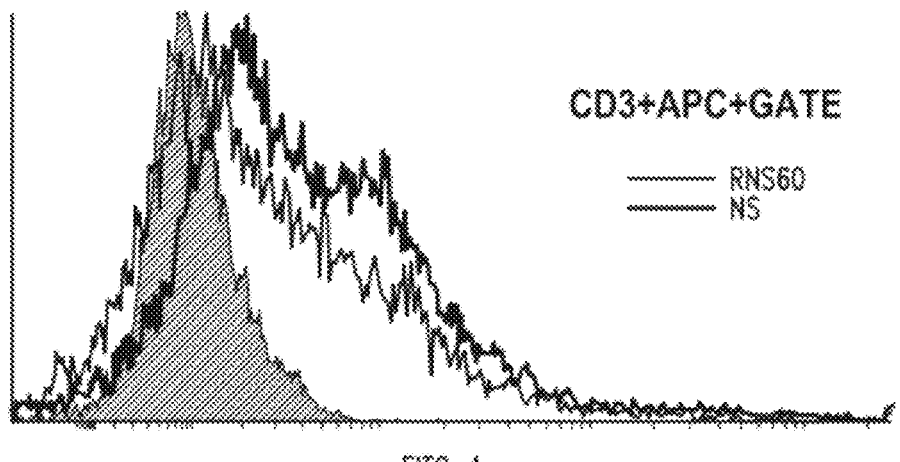
Figure 17A:
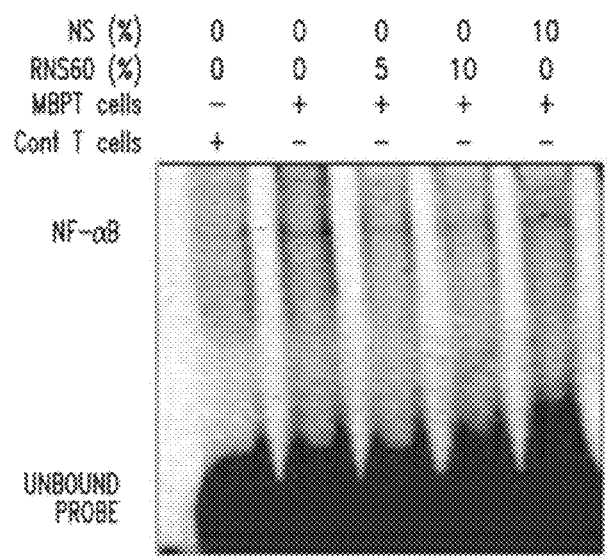
FIGS. 17 A-C show the results from two gel shift experiments (panels A and B) and a luciferase activity (reporter gene) assay (panel C) that examined the effects of RNS60 on the activation of NFκB in MBP-primed T cells.
Figure 17B:
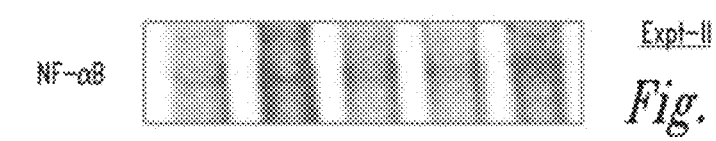
Figure 17C:
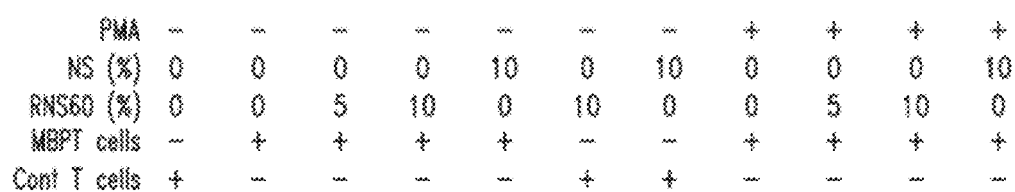
Figure 17C:
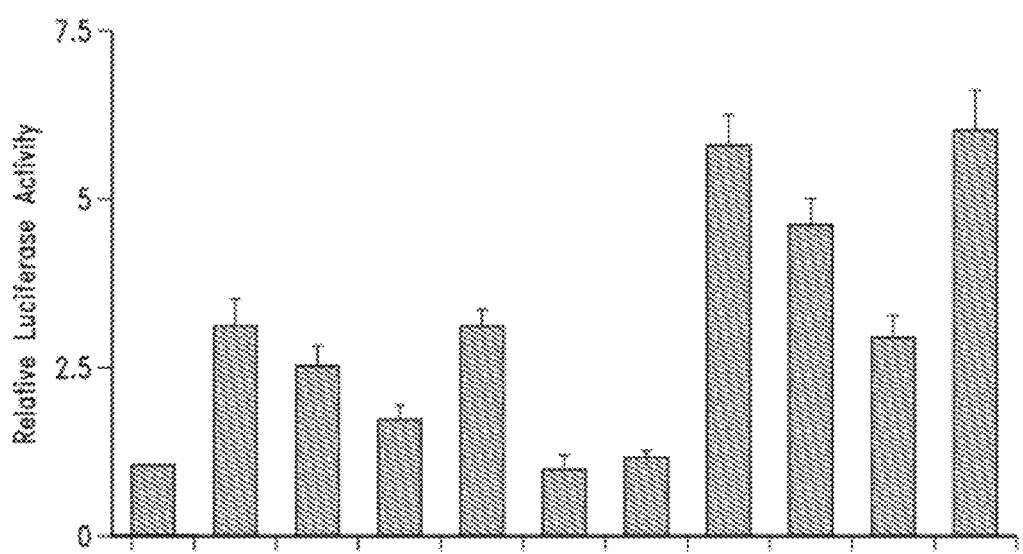

With respect to CD154 (CD40L), as shown in FIG. 16 A, the receptor is down-regulated in the presence of RNS-60 when compared to the level of the receptor expression in normal saline.

With respect to CD11B, as shown in FIG. 16 B, the receptor is down-regulated in the presence of RNS-60 when compared to the level of the receptor expression in normal saline.

With respect to CD3, as shown in FIG. 16 C, the receptor is down-regulated in the presence of RNS-60 when compared to the level of the receptor expression in normal saline.

Example 16

RNS60, but not Normal Saline (NS), Attenuated the Activation of NFκB in MBP-Primed T Cells Overview.

NF-κB kinase is a kinase widely recognized in the art as mediating inflammatory responses in inflammation-mediated conditions and diseases.

This Example shows that RNS60, but not normal saline (NS), attenuated the activation of NFκB in MBP-primed T cells. According to particular aspects, therefore, the present electrokinetically-generated fluids have substantial utility for treating inflammation and inflammation-mediated conditions and diseases, including but not limited to, diabetes and related metabolic disorders, insulin resistance, neurodegenerative diseases (e.g., M.S., Parkinson's, Alzheimer's, etc), asthma, cystic fibrosis, vascular/coronary disease, retinal and/or macular degeneration, digestive disorders (e.g., inflammatory bowel disease, ulcerative colitis, Crohn's, etc.).

Methods.

For the experiments shown in FIGS. 17 A and 17 B, T cells isolated from MBP-immunized mice were re-primed with MBP and after 24 h, cells received different concentrations of RNS60 and NS. After 2 h of treatment, DNA-binding activity of NF-κB was monitored in nuclear extracts by electrophoretic mobility shift assay (EMSA).

For experiments shown in FIG. 17 C, T cells isolated from MBP-immunized mice were transfected with PBIIX-Luc, an NF-κB dependent reporter construct, followed by repriming with MBP. After 24 h of MBP priming, cells were treated with different concentrations of RNS60 and NS for 2 h followed by assay of luciferase activity in total cell extracts by a luciferase assay kit (Promega). In other cases, MBP-primed T cells were also stimulated with 30 nM PMA for 1 h. In these cases, PMA was added after 1 h of pretreatment with RNS60 and NS. Results are mean±SD of three different experiments.

Results.

FIGS. 17 A-C show that RNS60, but not normal saline (NS), attenuated the activation of NF-κB in MBP-primed T cells. Specifically, FIGS. 17 A and 17 B show that RNS60 (see middle three lanes of FIGS. 17 A and 124 B), but not NS (see right-most lane of FIGS. 17 A and 17 B), attenuated the activation of NF-κB in MBP-primed T cells in a dose-responsive manner.

Likewise, the bar graph of FIG. 17 C shows that that RNS60 (see second, third and fourth bars of FIGS. 17 A and 17 B), but not NS (see fifth bar of FIGS. 17 A and 17 B), attenuated the activation of NF-κB in MBP-primed T cells, and hence also attenuated luciferase activity from the transfected NF-κB-dependent reporter construct (PBIIX-Luc) in total cell extracts, in a dose-responsive manner.

According to particular aspects, therefore, the disclosed electrokinetically-generated fluids have substantial utility for treating inflammation and inflammation-mediated conditions and diseases, including but not limited to, diabetes and related metabolic disorders, insulin resistance, neurodegenerative diseases (e.g., M.S., Parkinson's, Alzheimer's, etc), asthma, cystic fibrosis, vascular/coronary disease, retinal and/or macular degeneration, digestive disorders (e.g., inflammatory bowel disease, ulcerative colitis, Crohn's, etc.).

Example 17

RNS60, but not Normal Saline (NS), Attenuated Fibrillar Aβ1-42 Peptide Induced Tau Phosphorylation in Primary Neurons Overview.

Taupathies, as recognized in the art, are characterized by exhibiting increased phosphorylation of tau protein (e.g., in neurons of a subject). Taupathies include, but are not limited to Alzheimer's disease, argyorphilic grain disease, frontotemporal dementia, progressive supranuclear palsy, corticobasal degeneration, frontotemporal lobar degeneration (Pick's disease), and Dementia pugilistica (DP) (a.k.a., boxer's dementia, chronic boxer's encephalopathy).

Particular aspects of the present invention provide methods for treating a taupathy or at least one symptom thereof, comprising administering to a subject in need thereof a therapeutically effective amount of an electrokinetically altered aqueous fluid comprising an ionic aqueous solution of charge-stabilized oxygen-containing nanostructures substantially having an average diameter of less than about 100 nanometers and stably configured in the ionic aqueous fluid in an amount sufficient for modulation of tau phosphorylation to provide for treating a taupathy or at least one symptom thereof in the subject. In certain aspects, the charge-stabilized oxygen-containing nanostructures are stably configured in the ionic aqueous fluid in an amount sufficient to provide, upon contact of a living cell by the fluid, modulation of at least one of cellular membrane potential and cellular membrane conductivity.

Figure 18A:
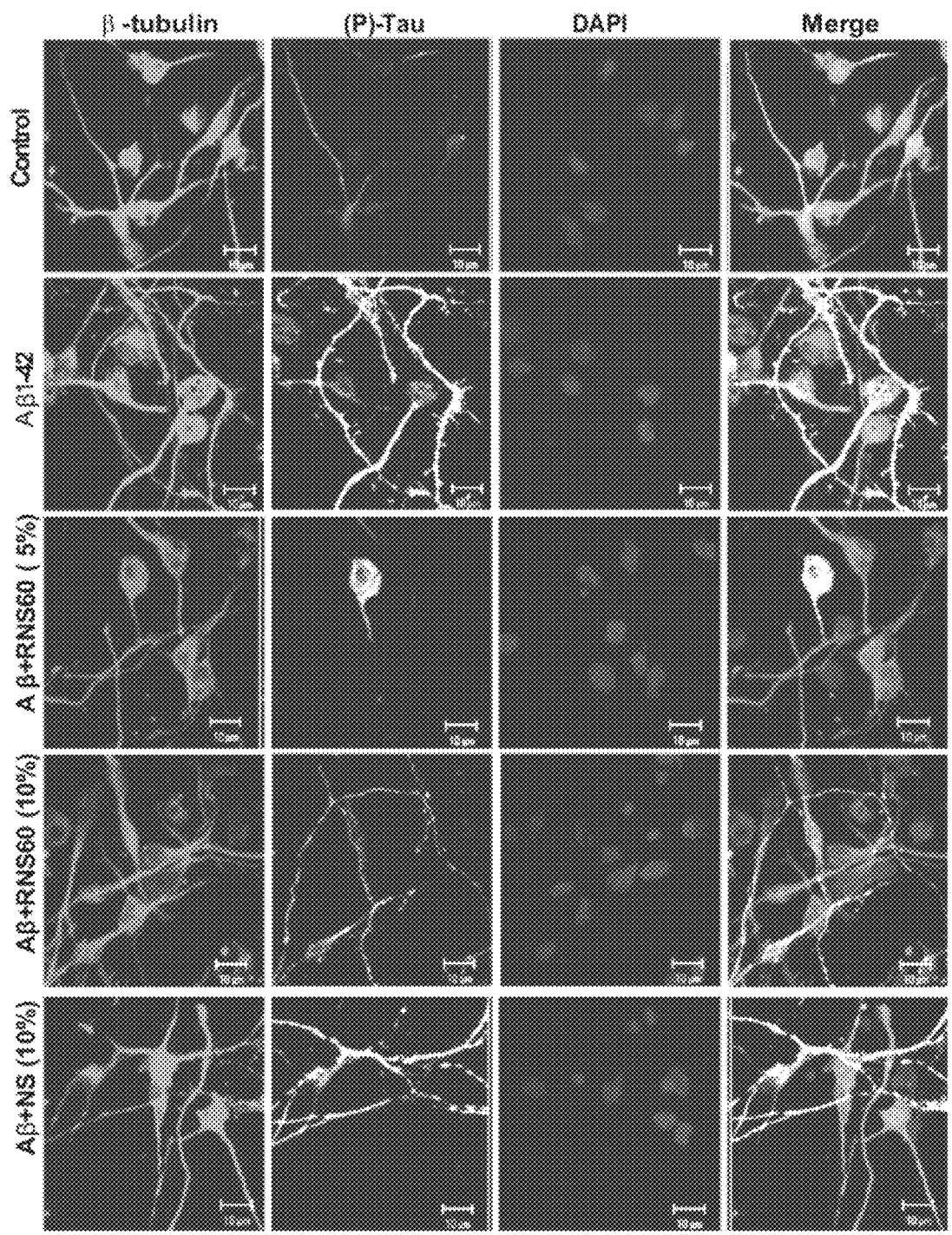
FIGS. 18 A-B show the results from an experiment examining the effects of RNS60 on fibrillar Aβ(1-42)-mediated tau phosphorylation in primary neurons. Tau phosphorylation was monitored by double-label immunofluorescence using antibodies against β-tubulin and phospho-tau. Beta-tubulin was used as a marker for neurons and DAPI staining was used to visualize the nucleus of cells.
Figure 18B:
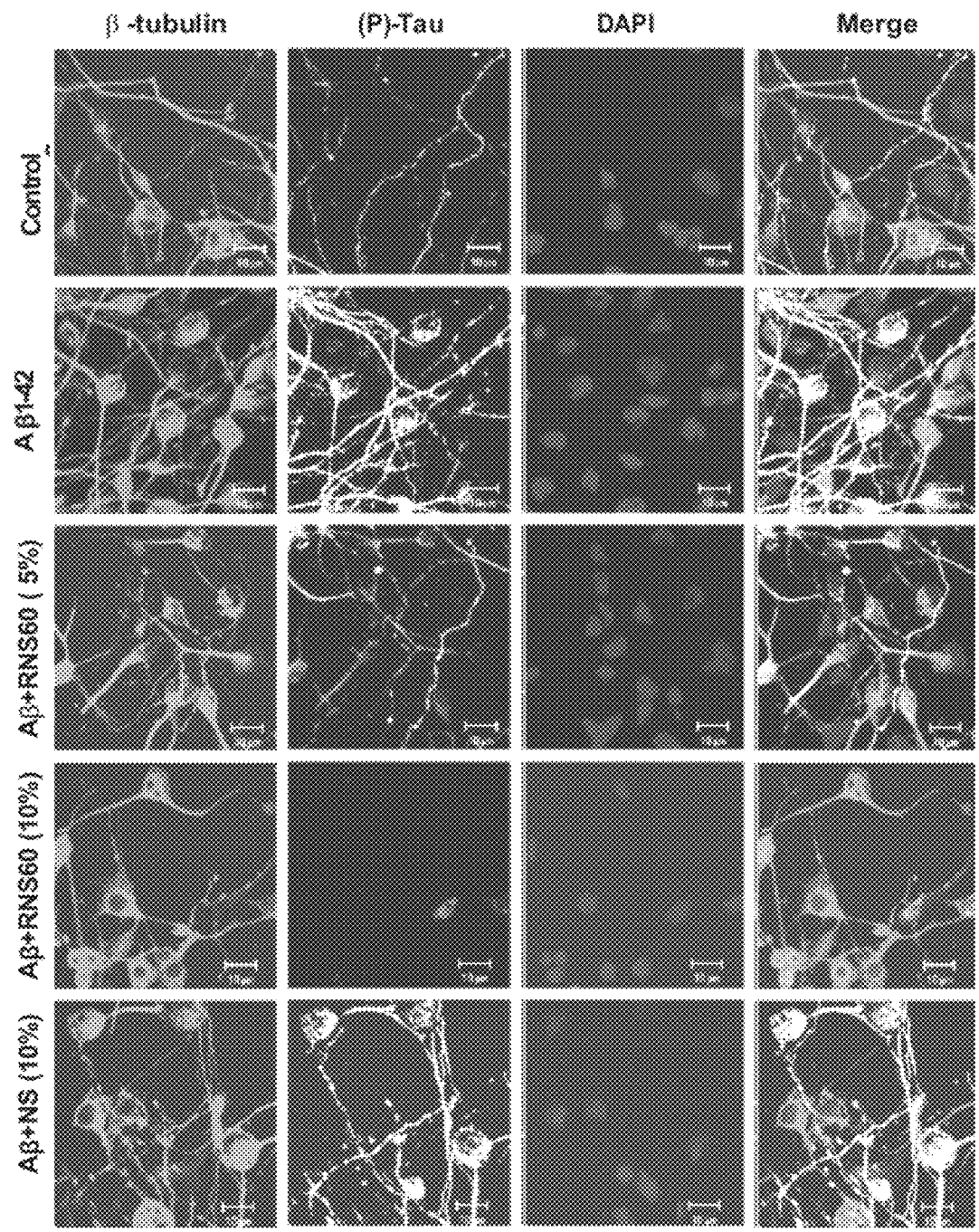

FIGS. 18 A-B show the results from an experiment examining the effects of RNS60, compared with normal saline (NS) control, on fibrillar Aβ(1-42)-mediated tau phosphorylation in primary neurons. Tau phosphorylation was monitored by double-label immunofluorescence using antibodies against β-tubulin and phospho-tau. Beta-tubulin was used as a marker for neurons and DAPI staining was used to visualize the nucleus of cells. The third and fourth panels from the top in the column labeled "(p)-Tau", shows that Tau phosphorylation was inhibited by RNS60 in a dose-dependent manner, whereas control normal saline ("NS") had no effect, even at the high dose of 10% (see bottom panel the column labeled "(p)-Tau".

Example 18

RNS60, but not Normal Saline (NS), Inhibited the Expression of Proinflammatory Molecules in Glial Cells Via Type 1A Phosphatidylinositol-3 Kinase (PI-3K)-Mediated Upregulation of IκBα and Inhibition of NF-κB Activation Overview.

Neuroinflammation underlies the pathogenesis of various neurodegenerative disorders including taupathies. Despite intense investigations, no effective therapy is available to stop its onset or halt its progression. As discussed herein, RNS60 is a 0.9% saline solution containing charge-stabilized nanostructures, which has been generated by subjecting normal saline to Taylor-Couette-Poiseuille flow under elevated oxygen pressure. This Example shows that RNS60 inhibits the expression of proinflammatory molecules in glial cells via type 1A phosphatidylinositol-3 kinase (PI-3K)-mediated upregulation of IκBα and inhibition of NF-κB activation. Consistently, RNS60 treatment increased the level of IκBα, inhibited the activation of NF-κB and attenuated the expression of inducible nitric oxide synthase (iNOS) in vivo in the substancia nigra pars compacta (SNpc) of 1-methyl-4-phenyl-1,2,3,6-tetrahydropyridine (MPTP)-intoxicated mice. These findings paralleled dopaminergic neuronal protection, normalized striatal neurotransmitters, and improved motor functions in MPTP-intoxicated mice. These results, taken together, delineate a novel anti-inflammatory property of RNS60 and suggest a therapeutic role of this compound in human taupathies and other neurodegenerative disorders (e.g., Parkinsonism).

Methods:

Isolation of Primary Mouse Microglia and Astroglia.

Microglia were isolated from mixed glial cultures according to the procedure of Giulian and Baker (Giulian and Baker, 1986) with modifications as previously described by us (Roy et al., 2006; Jana et al., 2007). Briefly, on day 9, the mixed glial cultures were washed three times with Dulbecco's modified Eagle's medium/F-12 and subjected to shaking at 240 rpm for 2 h at 37° C. on a rotary shaker. The floating cells were washed, seeded on to plastic tissue culture flasks and incubated at 37° C. for 1 h. The attached cells were seeded onto new plates for further studies. Ninety to ninety-five percent of cells were found to be positive for Mac-1. On day 11, mixed glial cultures were washed and shaken again on a rotary shaker at 180 rpm for 18 h. Floating cells were removed and remaining cells were trypsinized and seeded onto new plates for experiments. More than ninety-six percent of cells were positive for GFAP. Mouse BV-2 microglial cells (kind gift from Virginia Bocchini of University of Perugia) were also maintained and induced as indicated above.

Animals and MPTP Intoxication.

Six- to eight-week old C57BL/6 mice were purchased from Harlan, Indianapolis, Ind. Animal maintenance and experiments were in accordance with National Institute of Health guidelines and were approved by the Institutional Animal Care and Use committee (IACUC) of the Rush University of Medical Center, Chicago, Ill. For acute MPTP intoxication, mice received four intraperitoneal (i.p.) injections of MPTP-HCl (18 mg/kg of free base; Sigma Chemical Co., St. Louis, Mo.) in saline at 2-hr intervals (Ghosh et al., 2007; Ghosh et al., 2009). Control animals received only saline.

RNS60 Treatment.

Mice were treated with RNS60 and NS (300 ml/mouse/d) from 2 d prior to MPTP intoxication via intraperitoneal (i.p.) injection.

Assay for NO Synthesis.

Synthesis of NO was determined by assay of culture supernatant for nitrite, a stable reaction product of NO with molecular oxygen, using Griess reagent as described earlier.

Assay of p85a-Associated (Type 1A) and p101-Associated (Type 18) PI 3-Kinases.

After stimulation, cells were lysed with ice-cold lysis buffer containing 1% v/v Nonidet P-40, 100 mM NaCl, 20 mM Tris (pH 7.4), 10 mM iodoacetamide, 10 mM NaF, 1 mM sodium orthovanadate, 1 mM phenylmethylsulfonyl chloride, 1 µg/ml leupeptin, 1 µg/ml antipain, 1 µg/ml aprotinin, and 1 µg/ml pepstatin A. Lysates were incubated at 4° C. for 15 min followed by centrifugation at 13,000×g for 15 min. The supernatant was precleared with protein G-Sepharose beads (Biorad) for 1 h at 4° C. followed by the addition of 1 µg/ml p85a or p101 monoclonal antibodies. After 2-h incubation at 4° C., protein G-Sepharose beads were added, and the resulting mixture was further incubated for 1 h at 4° C. The immunoprecipitates were washed twice with lysis buffer, once with phosphate-buffered saline, once with 0.5 M LiCl and 100 mM Tris (pH 7.6), once in water, and once in kinase buffer (5 mM $MgCl_2$, 0.25 mM EDTA, 20 mM HEPES (pH 7.4)). PI 3-kinase activity was determined as described earlier using a lipid mixture of 100 µl of 0.1 mg/ml PI and 0.1 mg/ml phosphatidylserine dispersed by sonication in 20 mM HEPES (pH 7.0) and 1 mM EDTA. The reaction was initiated by the addition of 20 µCi of [g-$^{32}$P] ATP (3,000 Ci/mmol; NEN) and 100 µM ATP and terminated after 15 min by the addition of 80 µl of 1 N HCl and 200 µl of chloroform:methanol (1:1). Phospholipids were separated by TLC and visualized by exposure to iodine vapor and autoradiography (REF). Similarly to monitor p110a- and p110b-associated PI-3 kinase activity, supernatants were immunoprecipitated with antibodies against p110a and p110b followed by immunocomplex lipid kinase assay as described above.

Expression of Different Mutant Constructs of PI-3 Kinase.

Class IA PI 3-kinase consists of a catalytic subunit (p110) of 110 kDa and a regulatory subunit (p85) of 85 kDa. In the dominant-negative form of p85a, 35 amino acids in the inter-SH2 region from residues 479-513 of wild type p85a, important for binding the p110a/b subunit of PI 3-kinase, are deleted, and two other amino acids (Ser-Arg) are inserted in this deleted position. The engineering of the construct and description of the vector driving the expression of the proteins have been published previously. On the other hand, in the constitutively active mutant of p110a/b (p110*), the inter-SH2 domain of p85 is ligated to the $NH_2$-terminus of p110 whereas in the kinase-deficient mutant of p110a/b (p110-kd), the ATP binding site is mutated. Microglial cells plated in 12-well plates were transfected with 0.2 to 0.25 mg of different plasmids using Lipofectamine-Plus (Invitrogen) using manufacturer's protocol as described previously.

Electrophoretic Mobility Shift Assay (EMSA).

Nuclear extracts were prepared and EMSA was carried out as previously described (Ghosh et al., 2007; Saha et al., 2007; Brahmachari et al., 2009). Briefly, IRDye™ infrared dye end-labeled oligonucleotides containing the consensus binding sequence for NF-κB were purchased from LI-COR Biosciences (Lincoln, Nebr.). Six-micrograms of nuclear extract were incubated with binding buffer and with IR-labeled probe for 20 min. Subsequently, samples were separated on a 6% polyacrylamide gel in 0.25×TBE buffer (Tris borate-EDTA) and analyzed by Odyssey Infrared Imaging System (LI-COR Biosciences).

Transcriptional Activity of NF-kB.

Transcriptional activity of NF-kB was assayed as previously described (Ghosh et al., 2007; Saha et al., 2007; Brahmachari et al., 2009).

Semi-Quantitative RT-PCR Analysis.

Total RNA was isolated from ventral midbrain using Ultraspec-II RNA reagent (Biotex Laboratories, Inc., Houston, Tex.) following the manufacturer's protocol. To remove any contaminating genomic DNA, total RNA was digested with DNase. RT-PCR was carried out as described earlier (Ghosh et al., 2007; Brahmachari et al., 2009; Ghosh et al., 2009) using a RT-PCR kit (Clontech, Mountain View, Calif.).

Real-Time PCR Analysis.

It was performed in the ABI-Prism7700 sequence detection system (Applied Biosystems, Foster City, Calif.) as described earlier (Ghosh et al., 2007; Brahmachari et al., 2009; Ghosh et al., 2009) using TaqMan Universal Master mix and optimized concentrations of FAM-labeled probes and primers. Data were processed using the ABI Sequence Detection System 1.6 software.

Immunohistochemistry and Quantitative Morphology.

Seven days after MPTP intoxication, mice were sacrificed and their brains fixed, embedded, and processed for tyrosine hydroxylase (TH) and thionin staining as previously described (Benner et al., 2004; Ghosh et al., 2007; Ghosh et al., 2009). Total numbers of TH-positive neurons in SNpc were counted stereologically with STEREO INVESTIGATOR software (MicroBrightfield, Williston, Vt.) by using an optical fractionator. Quantitation of striatal TH immunostaining was performed as described (Benner et al., 2004; Ghosh et al., 2007; Ghosh et al., 2009). Optical density measurements were obtained by digital image analysis (Scion, Frederick, Md.). Striatal TH optical density reflected dopaminergic fiber innervation. For immunofluorescence staining on fresh frozen sections, rat anti-mouse CD11b (1:100), goat anti-mouse GFAP (1:100), rabbit anti NF-κB p65 (1:100), goat anti-NF-κB p65 (1:100), rabbit anti phospho-p65 (1:100), and rabbit anti-mouse iNOS (1:250) were used. The samples were mounted and observed under a Bio-Rad MRC1024ES confocal laser scanning microscope.

HPLC Analyses.

Striatal levels of dopamine, DOPAC (3,4-dihydroxyphenylacetic acid) and HVA (homovanillic acid) were quantified as described earlier (Ghosh et al., 2007; Ghosh et al., 2009; Roy et al., 2010). Briefly, mice were sacrificed by cervical dislocation after 7 days of MPTP intoxication and their striata were collected and immediately frozen in dry ice and stored at −80 C until analysis. On the day of the analysis, tissues were sonicated in 0.2M perchloric acid containing isoproterenol and resulting homogenates were centrifuged at 20,000×g for 15 min at 4 C. After pH adjustment and filtration, 10 μl of supernatant was injected onto an Eicompak SC-3ODS column (Complete Stand-Alone HPLC-ECD System EiCOMHTEC-500 from JM Science Inc., Grand Island, N.Y.) and analyzed following the manufacturer's protocol.

$MPP^+$ was measured as described earlier. Briefly, nigra collected from mice after 3 h of the last injection of MPTP were homogenized in 0.2 M perchloric acid and processed as above. Supernatants were then analyzed in Waters 2695 separation module HPLC system using the Phenomenex Luna C18 separation column (250×4.6 mm; 280-nm UV wavelength) with an isocratic gradient consisting of mobile phase A (18 mΩ water with 0.01 M $H_3PO_4$) and mobile phase B (acetonitrile with 0.01 M $H_3PO_4$) (1:4) at the flow rate of 0.15 ml/min.

Behavioral Analyses.

Two types of behavioral experiments were conducted. This included open field experiment for locomotor activity and rotorod experiment for feet movement as described earlier (Ghosh et al., 2007; Ghosh et al., 2009; Roy et al., 2010). Locomotor activity was measured after 7 d of the last dose of MPTP injection in a Digiscan Monitor (Omnitech Electronics, Inc., Columbus, Ohio). This Digiscan Monitor records stereotypy and rearing, behaviors that are directly controlled by striatum, as well as other basic locomotion parameters, such as horizontal activity, total distance traveled, number of movements, movement time, rest time, mean distance, mean time, and center time. Before any insult or treatment, mice were placed inside the Digiscan Infra-red Activity Monitor for 10 min daily and on rotorod for 10 min daily for 3 consecutive days to train them and record their baseline values. Briefly, animals were removed directly from their cages and gently placed nose first into a specified corner of the open-field apparatus and after release, data acquisition began at every 5 min interval. DIGISCAN software was used to analyze and store horizontal and vertical activity data, which were monitored automatically by infra-red beams. In rotorod, the feet movement of the mice was observed at different speeds. To eliminate stress and fatigues, mice were given a 5-min rest interval. Then 7 d after the last dose of MPTP, open field assays and rotorod tests were carried out twice at 6 h intervals on each mouse separately (Ghosh et al., 2007; Ghosh et al., 2009; Roy et al., 2010). Locomotor activity measures were assessed after baseline value comparison.

Statistics.

All values are expressed as means±SEM. One way ANOVA was performed while analyzing dose-dependent effect of RNS60 on mRNA expression of iNOS, IL-1b and IkBa in activated microglial cells. In other cases, Student's t-test was used to compare outcome between two groups (e.g. control vs MPTP, MPTP vs RNS60 etc).

Results:

RNS60 attenuates the expression of proinflammatory molecules in activated mouse microglia and astroglia: Activated microglia and astroglia are known to produce excessive amount of NO and proinflammatory cytokines having the potential of damaging dopaminergic neurons. The neurotoxic effect of MPTP depends on its conversion into $MPP^+$. In glial cells, monoamine oxidase B converts MPTP to $MPP^+$, which then leads to glial activation (REF). Therefore, we first investigated whether RNS60 could suppress MPP+-induced expression of iNOS and IL-1β in microglia. RNS60 dose-dependently inhibited the mRNA expression of iNOS and IL-1β in BV-2 microglial cells. This effect was specific to RNS60 as unprocessed NS from the same batch had no such inhibitory effect. In addition to MPP+, many other stimuli are capable of activating glial cells, including LPS, which is a prototype inducer of various proinflammatory molecules in different cell types including mouse microglia. Primary mouse microglia preincubated with RNS60 and NS for 2 h were stimulated with LPS, As expected, LPS induced the expression of iNOS protein in primary microglia. RNS60, but not NS, markedly suppressed LPS-induced expression of iNOS in microglia.

In addition to microglia, there are other glial cells in the CNS. For example, astroglia are the major glial cells in the CNS and astroglial activation participates in the pathogenesis of several neurodegenerative diseases. Earlier we have demonstrated that IL-1β is a potent inducer of iNOS in astroglia. Therefore, we examined the effect of RNS60 on the expression of iNOS in IL-1β-stimulated primary astroglia. Similar to microglia, RNS60, in this instance as well, markedly inhibited IL-1β-stimulated iNOS in primary mouse astroglia while NS had no such effect. (3-(4,5-dimethylthiazol-2-yl)-2,5-diphenyltetrazolium bromide (MTT) results show that RNS60 was not toxic to microglia or astroglia at any of the concentrations tested suggesting that the inhibitory effect of RNS60 on glial expression of iNOS was not due to any change in cell viability.

RNS60 inhibits microglial activation of NF-κB: LPS and other inflammatory stimuli including MPP+ are known to induce iNOS expression via activation of NF-κB. Because RNS60 attenuated the expression of iNOS in glial cells, we examined the effect of RNS60 on the activation of NF-κB. Activation of NF-κB was monitored by both DNA binding and transcriptional activity of NF-κB. Stimulation of BV-2 microglial cells with LPS resulted in the induction of DNA binding activity of NF-κB. However, RNS60 inhibited LPS-induced DNA-binding activity of NF-κB in microglial cells. We then tested the effect of RNS60 on the transcriptional activity of NF-κB. As expected, LPS induced NF-κB-dependent transcription of luciferase. Consistent with the effect of RNS60 on the DNA binding activity of NE-KB, RNS60 also suppressed the transcriptional activity of NE-KB in LPS-stimulated microglia. These results were specific as NS had no such inhibitory effect. These results indicate that RNS60 attenuates the expression of iNOS by suppressing the activation of NF-κB.

RNS60 Upregulates IκBα in Glial Cells.

Although there are multiple mechanisms by which an anti-inflammatory molecule may suppress the activation of NF-κB, in resting cells, the classical p65:p50 heterodimer is arrested in the cytoplasm as an inactive complex by IκBα. It has been also demonstrated that newly synthesized IκBα proteins accumulate in cytoplasm as well as in nucleus, where it reduces NE-KB binding. Therefore, we hypothesized that RNS60 might upregulate IκBα in order to suppress the activation of classical NF-κB heterodimer. Interestingly, RNS60, but not NS, markedly upregulated IκBα protein in microglial cells in a time-dependent fashion. Significant increase in IκBα protein was observed within only 30 min of RNS60 treatment. This effect was specific as RNS60 did not upregulate the expression of RelA p65. Real-time PCR data also show marked time-dependent increase in IκBα mRNA by RNS60, but not NS. Similarly, RNS60 also dose-dependently increased the expression of IκBα, but not p65 and p50. To confirm this IκBα upregulation from another angle, we also performed double-label immunofluorescence. RNS60, but not NS, markedly increased the expression of IκBα in CD11b-positive primary microglia. To investigate whether the IκBα upregulation by RNS60 is cell-type specific, we then treated primary astrocytes with RNS60. Similar to its effect in microglia, RNS60 also upregulated IκBα in GFAP-positive astroglia.

Activation of Phosphatidylinositol-3 (PI-3) Kinase in Microglia by RNS60.

Next we investigated mechanisms by which RNS60 may transduce signals for the upregulation of IκBα. RNS60 contains charge-stabilized nanostructures that have the potential to interact with the cell membrane. As activation of PI-3 kinase, a dual protein and lipid kinase, occurs in close association with the cell membrane, we investigated the effect of RNS60 on the activation of PI-3 kinase. Class IA PI-3 kinase, which is regulated by receptor tyrosine kinases, consists of a heterodimer of a regulatory 85-kDa subunit and a catalytic 110-kDa subunit (p85:p110α/β). Class IB PI-3 kinase, on the other hand, consists of a dimer of a 101-kDa regulatory subunit and a p110γ catalytic subunit (p101/p110γ). Interestingly, we observed that RNS60, but not NS, markedly induced the activation of p85α-associated PI-3 kinase within 15 min of treatment as evidenced by lipid kinase activity, suggesting that RNS60 induces the activation of class IA PI-3 kinase. RNS60 did not, however, activate p101-associated PI-3 kinase activity, suggesting that it is unable to activate class IB PI-3 kinase. Next we tried to identify the catalytic subunit of class IA PI-3 kinase that is involved in this lipid kinase activity. The regulatory subunit p85α can associate itself with both p110α and/or p110β. By immunocomplex lipid kinase assay, we observed that RNS60-induced activation of PI-3 kinase was due to both p110α and p110β.

Activation of Akt in Microglia by RNS60.

PI 3-kinases have been linked to a diverse group of cellular functions and many of these functions are related to the ability of class I PI 3-kinases to activate protein kinase B (PKB, aka Akt). Therefore, we examined if RNS60 could activate Akt in microglia. Similar to the activation of PI-3 kinase, RNS60 markedly induced the activation of Akt at 30 and 60 min of stimulation as evident from immunoblot analysis of phospho-Akt, without increasing the level of total Akt. NS had no such effect on Akt phosphorylation. Immunofluorescence analysis of phospho-Akt and total Akt in RNS60-treated microglia also confirms the finding that RNS60, but not NS, induces the activation of Akt in microglia.

Because RNS60 induced the activation of PI-3 kinase-Akt signaling pathway, we investigated the possibility if RNS60 was utilizing this pathway to exhibit its anti-inflammatory activity. We examined the effect of LY294002, an inhibitor of PI-3 kinase, and AktI, an inhibitor of Akt, on RNS60-mediated anti-inflammatory effect. As expected, bacterial LPS induced the production of NO and the expression of iNOS protein in microglia. RNS60 also markedly inhibited the production of NO and the expression of iNOS protein in LPS-stimulated microglial cells. However, both LY294002 and AktI abrogated the inhibitory effect of RNS60 on the induction of iNOS in LPS-stimulated microglial cells indicating the involvement of the PI-3 kinase-Akt pathway in RNS60-mediated suppression of iNOS. Next we investigated if RNS60 also required the PI-3 kinase-Akt pathway for upregulating the expression of IκBα and suppressing the activation of NF-κB. Similar to the regulation of iNOS, both LY and AktI also abolished the RNS60-mediated upregulation of IκBα protein and mRNA and eliminated the RNS60-mediated inhibition on NF-κB activation in LPS-stimulated microglial cells.

To confirm this observation further, we transfected BV-2 microglial cells with a dominant-negative mutant of p85α. Expression of a dominant-negative mutant of p85α, in which the inter-SH2 region required for binding of p110α/β subunit is disrupted, results in the inhibition of PI 3-kinase activity in different cell types including C6 glial cells and BV-2 glial cells, indicating that the over-expressed dominant-negative mutant protein of p85α did not associate with the catalytic subunit of PI 3-kinase. As evidenced by Western blot analysis and real-time PCR, RNS60 induced the expression of IκBα protein and mRNA in empty vector-transfected, but not p85α-transfected, microglial cells. These results suggest that RNS60 upregulates IκBα and exerts its anti-inflammatory effect in microglial cells via the PI-3 kinase-Akt signaling pathway.

Next we investigated if the activation of PI-3 kinase alone was sufficient to induce the expression of IκBα in microglia. It has been reported that expression of p110* (a constitutively-active mutant of p110α/β), but not p110-kd (a kinase dead mutant), is sufficient to promote Glut 4 translocation in adipocytes. Therefore, to increase the activity of p110α/β, mouse microglial cells were transfected with p110*. Earlier we have demonstrated that expression of p110*, but not p110-kd, increases the lipid kinase activity of PI 3-kinase in human astroglial cells. Over-expression of p110*, but not an empty vector, was capable of increasing mRNA and protein expression of IκBα. On the other hand, p110-kd had no effect on the expression of IκBα. These results indicate that activation of PI-3 kinase is sufficient to induce microglial expression of IκBα.

As RNS60 increased the level of the anti-inflammatory molecule IκBα in microglia and astroglia in vitro, we examined whether RNS60 was capable of augmenting the level of IκBα in vivo in the nigra of MPTP-insulted mice. Although MPTP intoxication markedly induced astrogliosis and microgliosis in vivo in the SNpc as evident from increased GFAP and CD11b, we observed a marginal decrease in IκBα expression after MPTP insult. However, similar to its effect in cultured astrocytes and microglia, RNS60 treatment significantly increased the level of IκBα in both GFAP-positive astroglia and CD11b-positive microglia in vivo in the SNpc of MPTP-intoxicated mice.

As RNS60 treatment upregulated IκBα, a specific inhibitor of NF-κB, we examined if RNS60 treatment could suppress the activation of NF-κB in vivo in the SNpc of MPTP-insulted mice. NF-κB was monitored in the SNpc seven days after the last injection of MPTP. MPTP intoxication led to marked induction of RelA p65 in the SNpc as compared to saline treatment. Double-label immunofluorescence analysis indicated that p65 was principally expressed in GFAP-positive astroglia and CD11b-positive microglia. In addition to stimulus-induced nuclear translocation of NF-κB, it has been shown that stimulus-induced phosphorylation of the p65 plays a key role in the transcriptional activation after the nuclear translocation. Accordingly, the level of phospho-p65 was also markedly higher in the SNpc of MPTP-intoxicated mice as compared to saline treated mice confirming NF-κB activation in vivo in the SNpc of MPTP-lesioned mice. However, RNS60 strongly inhibited the induction of total p65 as well as phospho-p65 in vivo in the SNpc of MPTP-intoxicated mice. Under similar conditions, NS did not inhibit the induction of p65 and phosphorylation of p65.

Inflammation plays a role in the loss of dopaminergic neurons in PD and its animal model. As RNS60 inhibited the expression of iNOS in glial cells and suppressed the activation of NF-κB in vivo in the nigra of MPTP-intoxicated mice, we examined if RNS60 was able to suppress the expression of iNOS in vivo in the SNpc of MPTP-insulted mice. Immunofluorescence analysis for iNOS in ventral midbrain sections showed that MPTP intoxication led to marked increase in nigral iNOS protein expression and that iNOS co-localized with GFAP-positive astroglia and CD11b-positive microglia. However, treatment of mice with RNS60, but not NS, led to marked suppression of iNOS in vivo in the nigra.

RNS60 protected against MPTP-induced neurodegeneration.

Mice were treated daily with RNS60 and NS via i.p. injection from 2 d prior to MPTP injection and seven days after the last injection of MPTP, animals were processed for quantification of dopaminergic cell bodies in the SNpc and of projecting dopaminergic fibers in the striatum using TH immunostaining. MPTP-intoxication led to approximately 70% loss of SNpc TH-positive neurons and 75% reduction of striatal TH ODs compared with saline-injected controls. However, in MPTP-injected mice treated with RNS60, less reduction in SNpc TH-positive neurons and striatal TH ODs was observed. On the other hand, no such protective effects were seen in MPTP-intoxicated mice that were treated with NS. Next to determine whether RNS60 protects against biochemical deficits caused by MPTP, we quantified the level of dopamine (DA) in the striata 7 days after the MPTP treatment. MPTP intoxication led to about 80% decrease in striatal DA compared to striata of saline-injected mice. In contrast, MPTP-intoxicated animals that received RNS60 Showed 50% Decrease in Striatal Dopamine, Whereas Such Protection was not seen in case of NS treatment.

RNS60 Improved Locomotor Functions in MPTP-Intoxicated Mice.

The ultimate therapeutic goal of neuroprotection is to decrease functional impairment. Therefore, to examine whether RNS60 protects not only against structural and neurotransmitter damage but also against functional deficits caused by MPTP, we monitored locomotor and open-field activities. MPTP injection caused a marked decrease in rotorod performance, movement time, number of movements, horizontal activity, total distance, rearing, and stereotypy. On the other hand, MPTP increased the rest time. However, RNS60, but not NS, significantly improved MPTP-induced hypolocomotion.

The neuroprotection seen by RNS60 could also be due to inhibition of MPTP to MPP+ conversion by glia. To address this possibility, we measured the level of MPP+ in nigra 3 h after the final MPTP injection. Although NS had no effect on nigral level of MPP+, surprisingly, RNS60 increased the availability of MPP+ in the nigra by six fold. Together, these results show that despite markedly increasing the availability of MPP+ in the nigra, RNS60 protects the nigrostriatum in MPTP-insulted mice.

In summary, we have demonstrated that RNS60 exhibits anti-inflammatory effects via (class IA PI-3K-Akt)-mediated upregulation of IκBα and inhibition of NF-κB activation. We also demonstrate that RNS60 upregulates IκBα and blocks the activation of NF-κB in the SNpc, inhibits nigral expression of iNOS, protects the loss of nigral dopaminergic neurons, saves striatal TH fibers and neurotransmitters, and improves the behavioral functions in MPTP-intoxicated mice. These results highlight the novel biological properties of RNS60 and indicate that RNS60 may be used for therapeutic intervention in taupathies and other neurodegenerative disorders as primary or adjunct therapy.

INCORPORATION BY REFERENCE

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

It should be understood that the drawings and detailed description herein are to be regarded in an illustrative rather than a restrictive manner, and are not intended to limit the invention to the particular forms and examples disclosed. On the contrary, the invention includes any further modifications, changes, rearrangements, substitutions, alternatives, design choices, and embodiments apparent to those of ordinary skill in the art, without departing from the spirit and scope of this invention, as defined by the following claims. Thus, it is intended that the following claims be interpreted to embrace all such further modifications, changes, rearrangements, substitutions, alternatives, design choices, and embodiments.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Accordingly, the invention is not limited except as by the appended claims.

The invention claimed is:

1. A method for decreasing of tau phosphorylation and/or aggregation in a subject, comprising administering to a subject in need thereof having a tauopathy a therapeutically effective amount of an oxygenated ionic aqueous solution of charge-stabilized oxygen-containing nanobubbles having an average diameter of less than 100 nanometers and stably configured in the ionic aqueous fluid in an amount sufficient for decreasing of tau phosphorylation and/or aggregation in the subject, and wherein the tauopathy is at least one selected from the group consisting of argyrophilic grain disease, frontotemporal dementia, progressive supranuclear palsy, corticobasal degeneration, frontotemporal lobar degeneration (Pick's disease), and Dementia pugilistica (DP), and wherein the oxygen in the fluid is present in an amount of at least 15 ppm at atmospheric pressure.

2. The method of claim 1, wherein the charge-stabilized oxygen-containing nanobubbles are the major charge-stabilized gas-containing nanostructure species in the ionic aqueous solution.

3. The method of claim 1, wherein the percentage of dissolved oxygen molecules present in the ionic aqueous solution as the charge-stabilized oxygen-containing nanobubbles is a percentage greater than 0.01%.

4. The method of claim 1, wherein the total dissolved oxygen is substantially present in the charge-stabilized oxygen-containing nanobubbles.

5. The method of claim 1, wherein the charge-stabilized oxygen-containing nanobubbles predominantly have an average diameter of less than 90 nm.

6. The method of claim 1, wherein the ionic aqueous solution comprises a saline solution.

7. The method of claim 1, wherein the tauopathy comprises at least one of argyorphilic grain disease, frontotemporal dementia, progressive supranuclear palsy, corticobasal degeneration, and frontotemporal lobar degeneration (Pick's disease).

8. The method of claim 7, wherein the tauopathy comprises frontotemporal dementia.

9. The method of claim 1, wherein the oxygen in the ionic aqueous solution is present in an amount of at least 25 ppm at atmospheric pressure.

10. The method of claim 1, wherein treating a taupathy, or at least one symptom thereof, comprises decreasing NF-κB expression and/or activity.

11. The method of claim 1, wherein treating comprises administration by at least one of topical, inhalation, intranasal, oral, intravenous (IV) and intraperitoneal (IP).

12. The method of claim 1, wherein the electrokinetically-altered fluid comprises at least one positively-charged ion selected from the group consisting of alkali metal based salts including Li+, Na+, K+, Rb+, and Cs+, alkaline earth based salts including Mg++ and Ca++, and transition metal-based positive ions including Cr, Fe, Co, Ni, Cu, and Zn, in each case along with any suitable counterionic components.

13. The method of claim 1, wherein the subject is a mammal, preferably a human.

* * * * *

```
SEQUENCE LISTING

<160> NUMBER OF SEQ ID NOS: 1

<210> SEQ ID NO 1
<211> LENGTH: 21
<212> TYPE: PRT
<213> ORGANISM: Artificial Sequence
<220> FEATURE:
<223> OTHER INFORMATION: MOG 35-55
<220> FEATURE:
<221> NAME/KEY: VARIANT
<222> LOCATION: (13)..(13)
<223> OTHER INFORMATION: Xaa = ornithine

<400> SEQUENCE: 1

Met Glu Val Gly Trp Tyr Arg Ser Pro Phe Ser Arg Xaa Val His Leu
1               5                   10                  15

Tyr Arg Asn Gly Lys
            20
```